(12) United States Patent
Condra et al.

(10) Patent No.: US 8,697,070 B2
(45) Date of Patent: Apr. 15, 2014

(54) 1D05 PCSK9 ANTAGONISTS

(75) Inventors: Jon H. Condra, Doylestown, PA (US); Rose M. Cubbon, Fanwood, NJ (US); Holly A. Hammond, Telford, PA (US); Laura Orsatti, Ponezia (IT); Shilpa Pandit, Edison, NJ (US); Laurence B. Peterson, Westfield, NJ (US); Joseph C. Santoro, Belle Mead, NJ (US); Ayesha Sitlani, Metuchen, MA (US); Dana D. Wood, Collegeville, PA (US); Henryk Mach, Amber, PA (US); Heidi Pixley, Glenside, PA (US); Sonia M. Gregory, Charlottesville, VA (US); Jeffrey T. Blue, Telford, PA (US); Kevin Wang, Lansdale, PA (US); Peizhi (Peter) Luo, Lansdale, PA (US); Denise K. Nawrocki, Annandale, NJ (US); Pingyu Zhong, Blue Bell, PA (US); Feng Dong, Lansdale, PA (US); Yan Li, San Jose, CA (US)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

(21) Appl. No.: 13/466,439

(22) Filed: May 8, 2012

(65) Prior Publication Data

US 2012/0301461 A1 Nov. 29, 2012

Related U.S. Application Data

(62) Division of application No. 12/322,867, filed on Feb. 6, 2009, now Pat. No. 8,188,234.

(60) Provisional application No. 61/063,949, filed on Feb. 7, 2008, provisional application No. 61/066,577, filed on Feb. 21, 2008.

(51) Int. Cl.
*A61K 38/00* (2006.01)

(52) U.S. Cl.
USPC .......... 424/130.1; 424/133.1; 424/141.1; 435/327; 530/387.1

(58) Field of Classification Search
None
See application file for complete search history.

(56) References Cited

U.S. PATENT DOCUMENTS

| | | | |
|---|---|---|---|
| 2002/0045571 A1 | 4/2002 | Liu et al. | |
| 2003/0059811 A1 | 3/2003 | Djaballah et al. | |
| 2003/0119038 A1 | 6/2003 | Bingham et al. | |
| 2004/0009553 A1 | 1/2004 | Glucksmann et al. | |
| 2004/0248177 A1 | 12/2004 | Abi Fadel et al. | |
| 2005/0147612 A1 | 7/2005 | Yayon et al. | |
| 2006/0234242 A1 | 10/2006 | Cheatham et al. | |
| 2009/0232795 A1 | 9/2009 | Condra et al. | |
| 2010/0040610 A1 | 2/2010 | Sitlani et al. | |
| 2010/0040611 A1 | 2/2010 | Sparrow et al. | |
| 2010/0041102 A1 | 2/2010 | Sitlani et al. | |

FOREIGN PATENT DOCUMENTS

| | | |
|---|---|---|
| EP | 1 067 182 | 1/2001 |
| EP | 1 440 981 | 7/2004 |
| EP | 1 471 152 | 10/2004 |
| WO | WO 01/31007 | 5/2001 |
| WO | WO 01/34768 | 5/2001 |
| WO | WO 01/57081 | 8/2001 |
| WO | WO 01/77137 | 10/2001 |
| WO | WO 01/98468 | 12/2001 |
| WO | WO 02/14358 | 2/2002 |
| WO | WO 02/46383 | 6/2002 |
| WO | WO 02/090526 | 11/2002 |
| WO | WO 02/102993 | 12/2002 |
| WO | WO 02/102994 | 12/2002 |
| WO | WO 2004/018649 | 3/2004 |
| WO | WO 2004/097047 | 11/2004 |
| WO | WO 2007/134161 | 11/2007 |
| WO | WO 2008/057457 | 5/2008 |
| WO | WO 2008/057458 | 5/2008 |
| WO | WO 2008/057459 | 5/2008 |
| WO | WO 2008/063382 | 5/2008 |
| WO | WO 2008/086395 | 7/2008 |
| WO | WO 2008/118386 | 10/2008 |
| WO | WO 2008/125623 | 10/2008 |
| WO | WO 2008/133647 | 11/2008 |
| WO | WO 2009/026558 | 2/2009 |
| WO | WO 2009/055783 | 4/2009 |
| WO | WO 2009/100318 | 8/2009 |
| WO | WO 2010/029513 | 3/2010 |

OTHER PUBLICATIONS

Padlan et al, 1995, FASEB J, vol. 9, p. 133-139.*
Burgess et al (J Cell Biol, 1990, 111:2129-2138).*
Lazar et al (Mol Cell Biol, 1998, 8:1247-1252).*
Akers et al., 2002 Pharm Biotech 14:47-127.
Alborn et al., 2007 Clinical Chemistry, 53:1814-1819.
Benjannet et al., 2006 J. Biol. Chern. 281(41):30561-72. Epub Aug. 15, 2006.
Benjannet et al. (2004) *J Biol Chem.* 279(47):48865-75 "NARC-1/PCSK9 and its natural mutants: zymogen cleavage and effects on the low density lipoprotein (LDL) receptor and LDL cholesterol".
Bottomley et al., 2009 J Biol Chern 284(2): 1313-23, Epub Nov. 10, 2008.

(Continued)

*Primary Examiner* — Sean Aeder
*Assistant Examiner* — Julie Wu
(74) *Attorney, Agent, or Firm* — Sheela Mohan-Peterson

(57) ABSTRACT

Antagonists of human proprotein convertase subtilisin-kexin type 9 ("PCSK9") are disclosed. The disclosed antagonists are effective in the inhibition of PCSK9 function and, accordingly, present desirable antagonists for use in the treatment of conditions associated with PCSK9 activity. The present invention also discloses nucleic acid encoding said antagonists, vectors, host cells, and compositions comprising the antagonists. Methods of making PCSK9-specific antagonists as well as methods of using the antagonists for inhibiting or antagonizing PCSK9 function are also disclosed and form important additional aspects of the present disclosure.

6 Claims, 16 Drawing Sheets

(56) References Cited

OTHER PUBLICATIONS

Chen et al. Selection and analysis of an optimized anti-VEGF antibody: crystal structure of an affinity matured Fab in complex with antigen. Journal of Molecular Biology, 1999. vol. 293, pp. 865-881.
Chen et al., 2003 Pharm Res 20: 1952-1960.
Cohen et al. (2006) *N. Engl. J. Med.* 354(12):1264-1272 "Sequence variations in PCSK9, low LDL, and protection against coronary heart disease".
Cohen et al., 2005 Nat. Genet, 37:161-165, Epub Jan. 16, 2005 Erratum in: Nat Genet. Mar. 2005;37(3):328.
Colman (1994) *Res Immunol.* 145(1):33-36 "Effects of amino acid sequence changes on antibody-antigen interactions".
De Pascalis et al. (2002) *Journal of Immunology* 169:3076-3084 "Grafting of abbreviated complementarity determining regions containing specificity determining residues essential for ligand contact to engineer a less immunogenic humanized monoclonal anfibody".
Fisher et al., 2007 J Biol Chem. 282(28):20502-12. Epub May 10, 2007.
GenomeNet—Database: PIR, Entry: TI8240, Barrell et al., LinkDB: TI8240(Sep. 7, 2004).
GenomeNet—Database: UniProt, Entry: AOE922_PARTE, Amy et al., LinkDB: AOE922_PARTE (Mar. 2006).
Grozdanov et al., 2006 Biochem Cell Biol 84:80-92.
Holm, et al. Functional mapping and single chain construction of the anti-cytokeratin 8 monoclonal antibody TS1. Molecular Immunology, 2007. vol. 44, pp. 1075-1084.
Horton et al., 2007 Trends Biochem Sciences 32:71-77.
Knappik et al., 2000 J. Mol. Biol. 296:57-86.
Kwon et al., 2008 PNAS 105:1820-1825.
Lagace et al., 2006 J Clin Invest 116:2995-3005.
Lalanne et al. (2005) *J. Lipid Res.* 46:1312-1319 "Wild-type PCSK9 inhibits LDL clearance but does not affect apoB-containing lipoprotein production in mouse and cultured cells".
Lopez et al., 2008 Biochim Biophy Acta 1781: 184-191.
Lopez, 2008 Drug News & Perspectives 21 :323-330.
Mac Callum et al. Antibody-antigen interactions: contact analysis and binding site topography. Journal of Molecular Biology, 1996. vol. 262, pp. 732-745.
Maxwell et al. (2003) *J Lipid Res.* 44(11):2109-19 "Novel putative SREBP and LXR target genes identified by microarray analysis in liver of cholesterol-fed mice".
Maxwell & Breslow, 2004 PNAS 101: 7100-7105.
Molloy et al., 1994 EMBO J. 13: 18-33.
Naureckiene et al., 2003 Archives Biochemistry Biophysics 420:55-67.
Ni et al., 2010 J Biol Chem. 285(17):12882-91. Feb. 19, 2010 [Epub ahead of print].
Ni et al., vol. 120, No. 18, Suppl. 2, 2009, p. S477, XP008121212, ISSN: 0009-7322.
Pandit et al., 2008 J Lipid Res. 49(6):1333-43. Epub Mar. 19, 2008.
Park et al. (2004) *J. Biol. Chem.* 279(48):50630-50638 Post-transcriptional regulation of low density lipoprotein receptor "protein by proprotein convertase subtilisin/kexin type 9a in mouse liver".
Paul, Fundamental Immunology, 3$^{rd}$ Edition, 1993, pp. 292-295.
Peterson et al., 2008 J Lipid Res. 49(7): 1595-9.
Rashid et al. (2005) *Proc Natl Acad Sci U S A.* 102(15):5374-9 "Decreased plasma cholesterol and hypersensitivity to statins in mice lacking Pcsk9".
Rudikoff et al. Single amino acid substitution altering antigen-binding specificity. Proceedings of the National Academy of Sciences, 1982. vol. 79, pp. 1979-1982.
Seidah, et al. (2003) *Proc Natl Acad Sci U S A.* 100(3):928-33 "The secretory proprotein convertase neural apoptosis-regulated convertase 1 (NARC-1): liver regeneration and neuronal differentiation".
Skolnick and Fetrow. From genes to protein structure and function: novel applications of computational approaches in the genomic era. Trends in Biotechnology, 2000. vol. 18, pp. 34-39.
Vajdos, et al. Comprehensive functional maps of the antigen binding site of an anti-ErbB2 antibody obtained with shotgun scanning mutagenesis. Journal of Molecular Biology, 2002. vol. 320, pp. 415-428.
Wu et al. Humanization of a murine monoclonal antibody by simultaneous optimization of framework and CDR residues. Journal of Molecular Biology, 1999. vol. 294, pp. 151-162.
Zhang et al., 2007 J. Biol. Chem. 282:18602-18612.
Zhao et al., 2006 Am J Hum Genet. Sep. 2006; 79(3): 514-523.
Goat Anti-PCSKO Polyclonal Antibody, Unconjugated from Novus Biologicals, Catalog No. NB-300-959 (Date: 2006).
Rabbit Anti-PCSK9 Polychlonal Antibody, Unconjugated from Cayman Chemical Catalog No. 10007185-1 (Date: 2006).

* cited by examiner

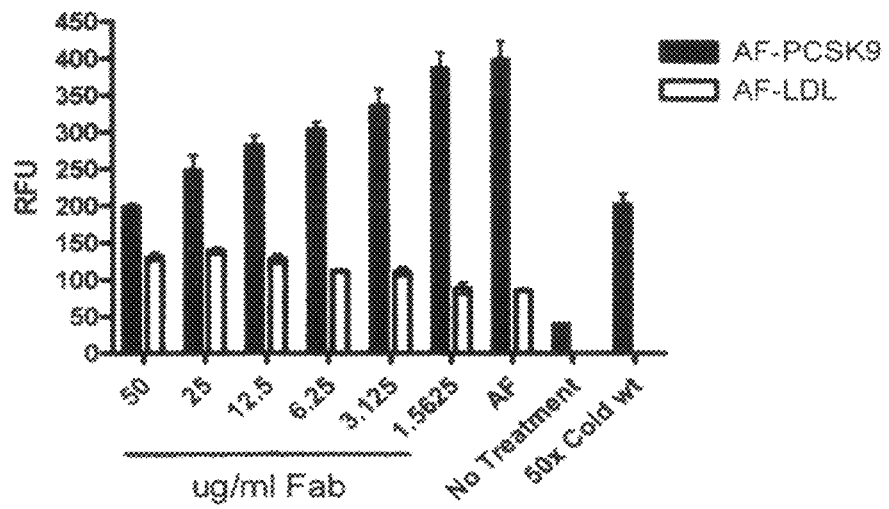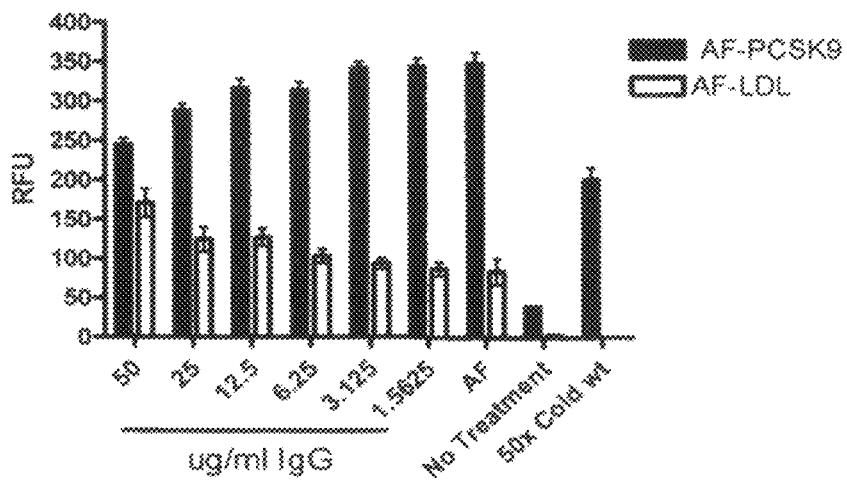
FIG. 4

|------CH1 →
IGG1         ASTK GPSVFPLAPS SKSTSGGTAA LGCLVKDYFP
IGG2         ASTK GPSVFPLAPC SRSTSESTAA LGCLVKDYFP
IGG4         ASTK GPSVFPLAPC SRSTSESTAA LGCLVKDYFP
IGG2M4       ASTK GPSVFPLAPC SRSTSESTAA LGCLVKDYFP

C200
IGG1     EPVTVSWNSG ALTSGVHTFP AVLQSSGLYS LSSVVTVPSS SLGTQTYICN VNHKPSNTKV
IGG2     EPVTVSWNSG ALTSGVHTFP AVLQSSGLYS LSSVVTVTSS NFGTQTYTCN VDHKPSNTKV
IGG4     EPVTVSWNSG ALTSGVHTFP AVLQSSGLYS LSSVVTVPSS SLGTKTYTCN VDHKPSNTKV
IGG2M4   EPVTVSWNSG ALTSGVHTFP AVLQSSGLYS LSSVVTVTSS NFGTQTYTCN VDHKPSNTKV

------Hinge region----||--------CH2 →   P238              M252    C261 D265 D270
IGG1     DKKAEPKSCD KTHTCPPCPA PELLGGPSVF LFPPKPKDTL MISRTPEVTC VVVDVSHEDP
IGG2     DKTVERKCC- --VECPPCPA PP-VAGPSVF LFPPKPKDTL MISRTPEVTC VVVDVSHEDP
IGG4     DKRVESKYGP ---PCPSCPA PEFLGGPSVF LFPPKPKDTL MISRTPEVTC VVVDVSQEDP
IGG2M4   DKTVERKCC- --VECPPCPA PP-VAGPSVF LFPPKPKDTL MISRTPEVTC VVVDVSQEDP
                              (Lower hinge)              FcRn-bind       B/C loop N297*         T307              C321        P329
IGG1     EVKFNWYVDG VEVHNAKTKP REEQYNSTYR VVSVLTVLHQ DWLNGKEYKC KVSNKALPAPI
IGG2     EVQFNWYVDG VEVHNAKTKP REEQFNSTFR VVSVLTVVHQ DWLNGKEYKC KVSNKGLPAPI
IGG4     EVQFNWYVDG VEVHNAKTKP REEQFNSTYR VVSVLTVLHQ DWLNGKEYKC KVSNKGLPSSI
IGG2M4   EVQFNWYVDG VEVHNAKTKP REEQFNSTFR VVSVLTVLHQ DWLNGKEYKC KVSNKGLPSSI
                    C'E loop            FcRn-bind                F/G loop

|----CH3 →
IGG1     EKTISKAKG QPREPQVYTL PPSRDELTKN QVSLTCLVKG FYPSDIAVEW ESNGQPENNY
IGG2     EKTISKTKG QPREPQVYTL PPSREEMTKN QVSLTCLVKG FYPSDIAVEW ESNGQPENNY
IGG4     EKTISKAKG QPREPQVYTL PPSQEEMTKN QVSLTCLVKG FYPSDIAVEW ESNGQPENNY
IGG2M4   EKTISKTKG QPREPQVYTL PPSREEMTKN QVSLTCLVKG FYPSDIAVEW ESNGQPENNY

H433
IGG1     KTTPPVLDSD GSFFLYSKLT VDKSRWQQGN VFSCSVMHEA LHNHYTQKSL SLSPGK*
         (SEQ ID NO: 21)
IGG2     KTTPPMLDSD GSFFLYSKLT VDKSRWQQGN VFSCSVMHEA LHNHYTQKSL SLSPGK*
         (SEQ ID NO: 22)
IGG4     KTTPPVLDSD GSFFLYSRLT VDKSRWQEGN VFSCSVMHEA LHNHYTQKSL SLSLGK*
         (SEQ ID NO: 23)
IGG2M4   KTTPPMLDSD GSFFLYSKLT VDKSRWQQGN VFSCSVMHEA LHNHYTQKSL SLSPGK*
         (SEQ ID NO: 24)
                                                    FcRn-bind

FIG. 6

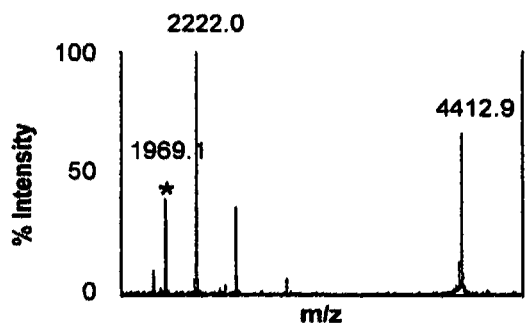
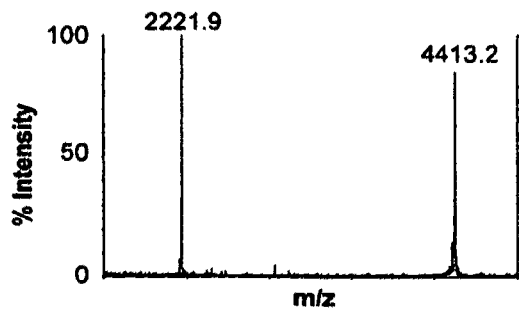
FIG. 7

¹⁵³SIPWNLERITP$^{165}$RY$^{167}$RAD$^{170}$EYQPPDGGSLV$^{181}$EVYLLDTSIQSDH$^{194}$R$^{195}$EI$^{197}$EG$^{199}$RY
MVTDFENVPEEDGT$^{216}$RFH$^{218}$RQASKCDSHGTHLAGVVSGRDAGVAKGASMRSLRVLNCQ
GKGTVSGTLIGLEFIRKSQLVQPVGPLVVLLPLAGGYSRVLNAACQRLARAGVVLVTAAGNFR
DDACLYSPASAPEVITVGATNAQDQPVTLGTLGTNFGRCVDLFAPGEDIIGASSDCSTCFVSQ
SGTSQAAAHVAGIAAMMLSAEPELTLAELRQRLIHFSAKDVINEAWFPEDQRVLTPNLVAALP
PSTHGAGWQLFCRTVWSAHSGPTRMATAIARCAPDEELLSCSSFSRSGKRRGERMEAQGG
KLVCRAHNAFGGEGVYAIARCCLLPQANCSVHTAPPAEASMGTRVHCHQQGHVLTGCSSH
WEVEDLGTHKPPVLRPRGQPNQCVGHREASIHASCCHAPGLECKVKEHGIPAPQEQVTVAC
EEGWTLTGCSALPGTSHVLGAYAVDNTCVVRSRDVSTTGSTSEEAVTAVAICCRSRHLAQAS
QELQKGNSADIQHSGGRSSLEGPRFEGKPIPNPLLGLDST RTGHHHHHH (SEQ ID NO: 38)

¹⁵³SIPWNLERITPPRYRADEYQPPDGGSLVEVYLLDTSIQSDHREIEGRVMVTDF (SEQ ID NO: 39)
¹⁵³SIPWNLERI P   ++  +E +  PDG S VEVYLLDTSIQ   HREIEGRV +TDF (SEQ ID NO: 40)

B

¹⁵³SIPWNLERII PAWHQTEEDRSPDGSSQVEVYLLDTSIQGAHREIEGRVTITDF (SEQ ID NO: 41

FIG. 12

A
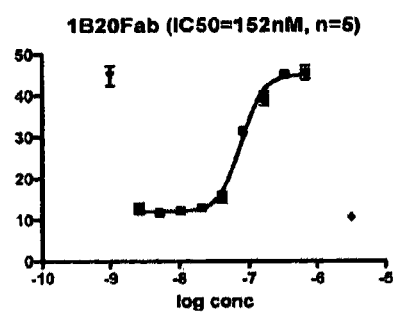
B
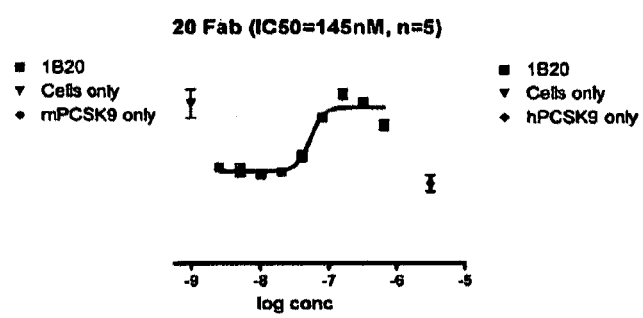
C
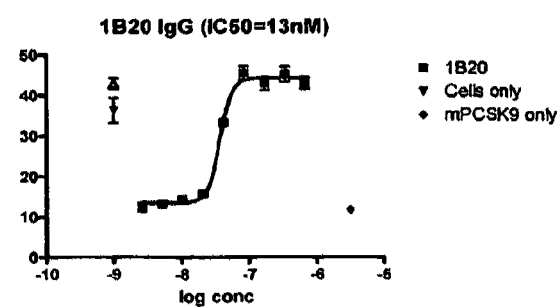
D
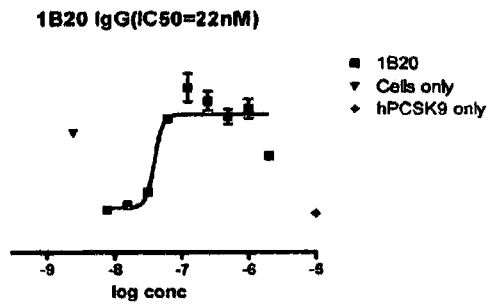
FIG. 14

SEQUENCE LISTING

```
<160> NUMBER OF SEQ ID NOS: 60

<210> SEQ ID NO 1
<211> LENGTH: 213
<212> TYPE: PRT
<213> ORGANISM: Artificial Sequence
<220> FEATURE:
<223> OTHER INFORMATION: LC; m2CX1D05

<400> SEQUENCE: 1

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Ser Ala
            20                  25                  30

Leu Asn Trp Tyr Gln Gln Lys Pro Gly Lys Ala Pro Lys Leu Leu Ile
        35                  40                  45

Tyr Asn Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Phe Asp Gly Asp Pro Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Ala
    210

<210> SEQ ID NO 2
<211> LENGTH: 639
<212> TYPE: DNA
<213> ORGANISM: Artificial Sequence
<220> FEATURE:
<223> OTHER INFORMATION: LC; m2CX1D05
```

-continued

```
<400> SEQUENCE: 2
gatatccaga tgacccagag cccgtctagc ctgagcgcga gcgtgggtga tcgtgtgacc     60
attacctgca gagcgagcca gggtattcgt tctgctctga attggtacca gcagaaacca    120
ggtaaagcac cgaaactatt aatttataat ggttctactt tgcaaagcgg ggtcccgtcc    180
cgttttagcg gctctggatc cggcactgat tttaccctga ccattagcag cctgcaacct    240
gaagactttg cggtttatta ttgccagcag tttgatggtg atcctacctt tggccagggt    300
acgaaagttg aaattaaacg tacggtggct gctccgagcg tgtttatttt tccgccgagc    360
gatgaacaac tgaaaagcgg cacggcgagc gtggtgtgcc tgctgaacaa ctttgatccg    420
cgtgaagcga agttcagtg gaaagtagac aacgcgctgc aaagcggcaa cagccaggaa     480
agcgtgaccg aacaggatag caaagatagc acctattctc tgagcagcac cctgaccctg    540
agcaaagcgg attatgaaaa acataaagtg tatgcgtgcg aagtgaccca tcaaggtctg    600
agcagcccgg tgactaaatc ttttaatcgt ggcgaggcc                           639

<210> SEQ ID NO 3
<211> LENGTH: 11
<212> TYPE: PRT
<213> ORGANISM: Artificial Sequence
<220> FEATURE:
<223> OTHER INFORMATION: VL CDR 1; m2CX1D05

<400> SEQUENCE: 3

Arg Ala Ser Gln Gly Ile Arg Ser Ala Leu Asn
 1               5                  10

<210> SEQ ID NO 4
<211> LENGTH: 33
<212> TYPE: DNA
<213> ORGANISM: Artificial Sequence
<220> FEATURE:
<223> OTHER INFORMATION: VL CDR 1; m2CX1D05

<400> SEQUENCE: 4
agagcgagcc agggtattcg ttctgctctg aat                                  33

<210> SEQ ID NO 5
<211> LENGTH: 11
<212> TYPE: PRT
<213> ORGANISM: Artificial Sequence
<220> FEATURE:
<223> OTHER INFORMATION: VL CDR2; m2CX1D05

<400> SEQUENCE: 5

Leu Leu Ile Tyr Asn Gly Ser Thr Leu Gln Ser
 1               5                  10

<210> SEQ ID NO 6
<211> LENGTH: 33
<212> TYPE: DNA
<213> ORGANISM: Artificial Sequence
<220> FEATURE:
<223> OTHER INFORMATION: VL CDR2; m2CX1D05

<400> SEQUENCE: 6
ctattaattt ataatggttc tactttgcaa agc                                  33

<210> SEQ ID NO 7
<211> LENGTH: 7
<212> TYPE: PRT
<213> ORGANISM: Artificial Sequence
```

-continued

```
<220> FEATURE:
<223> OTHER INFORMATION: VL CDR3; m2CX1D05

<400> SEQUENCE: 7

Gln Gln Phe Asp Gly Asp Pro
 1               5

<210> SEQ ID NO 8
<211> LENGTH: 21
<212> TYPE: DNA
<213> ORGANISM: Artificial Sequence
<220> FEATURE:
<223> OTHER INFORMATION: VL CDR3; m2CX1D05

<400> SEQUENCE: 8
cagcagtttg atggtgatcc t                                            21

<210> SEQ ID NO 9
<211> LENGTH: 255
<212> TYPE: PRT
<213> ORGANISM: Artificial Sequence
<220> FEATURE:
<223> OTHER INFORMATION: Fd CHAIN; m2CX1D05

<400> SEQUENCE: 9

Gln Val Gln Leu Val Gln Ser Gly Ala Glu Val Lys Lys Pro Gly Ser
 1               5                  10                  15

Ser Val Lys Val Ser Cys Lys Ala Ser Gly Thr Phe Asn Ser His
             20                  25                  30

Ala Ile Ser Trp Val Arg Gln Ala Pro Gly Gln Gly Leu Glu Trp Met
         35                  40                  45

Gly Gly Ile Asn Pro Ile Leu Gly Ile Ala Asn Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg His Tyr Glu Ile Gln Ile Gly Arg Tyr Gly Met Asn Val Tyr
            100                 105                 110

Tyr Leu Met Tyr Arg Phe Ala Ser Trp Gly Gln Gly Thr Leu Val Thr
        115                 120                 125

Val Ser Ser Ala Ser Thr Lys Gly Pro Ser Val Phe Pro Leu Ala Pro
    130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220

Val Asp Lys Lys Val Glu Pro Lys Ser Glu Phe Glu Gln Lys Leu Ile
225                 230                 235                 240

Ser Glu Glu Asp Leu Asn Gly Ala Pro His His His His His
                245                 250                 255
```

```
<210> SEQ ID NO 10
<211> LENGTH: 765
<212> TYPE: DNA
<213> ORGANISM: Artificial Sequence
<220> FEATURE:
<223> OTHER INFORMATION: Fd CHAIN; m2CX1D05

<400> SEQUENCE: 10
caggtgcaat tggttcagtc tggcgcggaa gtgaaaaaac cgggcagcag cgtgaaagtg      60
agctgcaaag cctccggagg cactttaat tctcatgcta tttcttgggt gcgccaagcc     120
cctgggcagg gtctcgagtg gatgggcggt atcaatccga ttcttggcat tgcgaattac     180
gcgcagaagt ttcagggccg ggtgaccatt accgcgatg aaagcaccag caccgcgtat     240
atggaactga gcagcctgcg tagcgaagat acggccgtgt attattgcgc gcgtcattat     300
gagattcaga ttggtcgtta tggtatgaat gtttattatc ttatgtatcg ttttgcttct     360
tggggccaag gcaccctggt gacggttagc tcagcgtcga ccaaaggtcc aagcgtgttt     420
ccgctggctc cgagcagcaa aagcaccagc ggcggcacgg ctgccctggg ctgcctggtt     480
aaagattatt cccggaacc agtcaccgtg agctggaaca gcggggcgct gaccagcggc     540 gtgcataccet ttccggcggt gctgcaaagc agcggcctgt atagcctgag cagcgttgtg     600
accgtgccga gcagcagctt aggcactcag acctatattt gcaacgtgaa ccataaaccg     660
agcaacacca aagtggataa aaagtggaa ccgaaaagcg aattcgagca gaagctgatc     720
tctgaggagg atctgaacgg cgcgccgcac catcatcacc atcac                      765

<210> SEQ ID NO 11
<211> LENGTH: 131
<212> TYPE: PRT
<213> ORGANISM: Artifical Sequence
<220> FEATURE:
<223> OTHER INFORMATION: VH; m2CX1D05

<400> SEQUENCE: 11

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser His
            20                  25                  30

Ala Ile Ser Trp Val Arg Gln Ala Pro Gly Gln Gly Leu Glu Trp Met
        35                  40                  45

Gly Gly Ile Asn Pro Ile Leu Gly Ile Ala Asn Tyr Ala Gln Lys Phe
    50                  55                  60

Gln Gly Arg Val Thr Ile Thr Ala Asp Glu Ser Thr Thr Ala Tyr
65                  70                  75                  80

Met Glu Leu Ser Ser Leu Arg Ser Glu Asp Thr Ala Val Tyr Tyr Cys
                85                  90                  95

Ala Arg His Tyr Glu Ile Gln Ile Gly Arg Tyr Gly Met Asn Val Tyr
            100                 105                 110

Tyr Leu Met Tyr Arg Phe Ala Ser Trp Gly Gln Gly Thr Leu Val Thr
        115                 120                 125

Val Ser Ser
    130

<210> SEQ ID NO 12
<211> LENGTH: 393
<212> TYPE: DNA
<213> ORGANISM: Artificial Sequence
<220> FEATURE:
<223> OTHER INFORMATION: VH; m2CX1D05
```

```
<400> SEQUENCE: 12
caggtgcaat tggttcagtc tggcgcggaa gtgaaaaaac cgggcagcag cgtgaaagtg      60
agctgcaaag cctccggagg cacttttaat tctcatgcta tttcttgggt gcgccaagcc     120
cctgggcagg gtctcgagtg gatgggcggt atcaatccga ttcttggcat tgcgaattac     180
gcgcagaagt tcagggccgg ggtgaccatt accgcggatg aaagcaccag caccgcgtat     240
atggaactga gcagcctgcg tagcgaagat acggccgtgt attattgcgc gcgtcattat     300
gagattcaga ttggtcgtta tggtatgaat gtttattatc ttatgtatcg ttttgcttct     360
tggggccaag gcaccctggt gacggttagc tca                                  393

<210> SEQ ID NO 13
<211> LENGTH: 10
<212> TYPE: PRT
<213> ORGANISM: Artificial Sequence
<220> FEATURE:
<223> OTHER INFORMATION: VH CDR1; m2CX1D05

<400> SEQUENCE: 13

Gly Gly Thr Phe Asn Ser His Ala Ile Ser
 1               5                  10

<210> SEQ ID NO 14
<211> LENGTH: 30
<212> TYPE: DNA
<213> ORGANISM: Artificial Sequence
<220> FEATURE:
<223> OTHER INFORMATION: VH CDR1; m2CX1D05

<400> SEQUENCE: 14
ggaggcactt ttaattctca tgctatttct                                       30

<210> SEQ ID NO 15
<211> LENGTH: 20
<212> TYPE: PRT
<213> ORGANISM: Artificial Sequence
<220> FEATURE:
<223> OTHER INFORMATION: VH CDR2; m2CX1D05

<400> SEQUENCE: 15

Trp Met Gly Gly Ile Asn Pro Ile Leu Gly Ile Ala Asn Tyr Ala Gln
 1               5                  10                  15

Lys Phe Gln Gly
            20

<210> SEQ ID NO 16
<211> LENGTH: 60
<212> TYPE: DNA
<213> ORGANISM: Artificial Sequence
<220> FEATURE:
<223> OTHER INFORMATION: VH CDR2; m2CX1D05

<400> SEQUENCE: 16
tggatgggcg gtatcaatcc gattcttggc attgcgaatt acgcgcagaa gtttcagggc      60

<210> SEQ ID NO 17
<211> LENGTH: 22
<212> TYPE: PRT
<213> ORGANISM: Artificial Sequence
<220> FEATURE:
<223> OTHER INFORMATION: VH CDR3; m2CX1D05
```

<400> SEQUENCE: 17

His Tyr Glu Ile Gln Ile Gly Arg Tyr Gly Met Asn Val Tyr Tyr Leu
1               5                   10                  15

Met Tyr Arg Phe Ala Ser
            20

<210> SEQ ID NO 18
<211> LENGTH: 66
<212> TYPE: DNA
<213> ORGANISM: Artificial Sequence
<220> FEATURE:
<223> OTHER INFORMATION: VH CDR3; m2CX1D05

<400> SEQUENCE: 18
cattatgaga ttcagattgg tcgttatggt atgaatgttt attatcttat gtatcgtttt    60
gcttct    66

<210> SEQ ID NO 19
<211> LENGTH: 6
<212> TYPE: PRT
<213> ORGANISM: Artificial Sequence
<220> FEATURE:
<223> OTHER INFORMATION: Internal Processing Site

<400> SEQUENCE: 19

Ser Ser Val Phe Ala Gln
1               5

<210> SEQ ID NO 20
<211> LENGTH: 6
<212> TYPE: PRT
<213> ORGANISM: Artificial Sequence
<220> FEATURE:
<223> OTHER INFORMATION: Internal Processing Site

<400> SEQUENCE: 20

Ser Ile Pro Trp Asn Leu
1               5

<210> SEQ ID NO 21
<211> LENGTH: 330
<212> TYPE: PRT
<213> ORGANISM: Artificial Sequence
<220> FEATURE:
<223> OTHER INFORMATION: contains Fc domain of IgG1

<400> SEQUENCE: 21

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Ala Glu Pro Lys Ser Cys Asp Lys Thr His Thr Cys Pro Pro Cys
            100                 105                 110

```
Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 22
<211> LENGTH: 326
<212> TYPE: PRT
<213> ORGANISM: Artificial Sequence
<220> FEATURE:
<223> OTHER INFORMATION: contains Fc domain of IgG2

<400> SEQUENCE: 22

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140
```

```
Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Thr Lys Gly Gln Pro Arg Glu
210                 215                 220

Pro Gln Val Tyr Thr Leu Pro Pro Ser Arg Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 23
<211> LENGTH: 327
<212> TYPE: PRT
<213> ORGANISM: Artificial Sequence
<220> FEATURE:
<223> OTHER INFORMATION: contains Fc domain of IgG4

<400> SEQUENCE: 23

Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175
```

```
Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Met Thr Lys
225             230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 24
<211> LENGTH: 326
<212> TYPE: PRT
<213> ORGANISM: Artificial Sequence
<220> FEATURE:
<223> OTHER INFORMATION: contains Fc domain of IgG2m4

<400> SEQUENCE: 24

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205
```

```
Ser Ser Ile Glu Lys Thr Ile Ser Lys Thr Lys Gly Gln Pro Arg Glu
    210                 215                 220

Pro Gln Val Tyr Thr Leu Pro Pro Ser Arg Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 25
<211> LENGTH: 457
<212> TYPE: PRT
<213> ORGANISM: Artificial Sequence
<220> FEATURE:
<223> OTHER INFORMATION: 1D05 IgG2m4 Heavy Chain

<400> SEQUENCE: 25

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser His
            20                  25                  30

Ala Ile Ser Trp Val Arg Gln Ala Pro Gly Gln Gly Leu Glu Trp Met
        35                  40                  45

Gly Gly Ile Asn Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Tyr Glu Ile Gln Ile Gly Arg Tyr Gly Met Asn Val Tyr
            100                 105                 110

Tyr Leu Met Tyr Arg Phe Ala Ser Trp Gly Gln Gly Thr Leu Val Thr
        115                 120                 125

Val Ser Ser Ala Ser Thr Lys Gly Pro Ser Val Phe Pro Leu Ala Pro
    130                 135                 140

Cys Ser Arg Ser Thr Ser Glu Ser Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Thr Ser Ser Asn Phe Gly
        195                 200                 205

Thr Gln Thr Tyr Thr Cys Asn Val Asp His Lys Pro Ser Asn Thr Lys
    210                 215                 220

Val Asp Lys Thr Val Glu Arg Lys Cys Cys Val Glu Cys Pro Pro Cys
225                 230                 235                 240
```

```
Pro Ala Pro Val Ala Gly Pro Ser Val Phe Leu Phe Pro Pro Lys
            245                 250                 255

Pro Lys Asp Thr Leu Met Ile Ser Arg Thr Pro Glu Val Thr Cys Val
        260                 265                 270

Val Val Asp Val Ser Gln Glu Asp Pro Glu Val Gln Phe Asn Trp Tyr
            275                 280                 285

Val Asp Gly Val Glu Val His Asn Ala Lys Thr Lys Pro Arg Glu Glu
        290                 295                 300

Gln Phe Asn Ser Thr Phe Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Gly Leu Pro Ser Ser Ile Glu Lys Thr Ile Ser Lys Thr Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Met Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 26
<211> LENGTH: 213
<212> TYPE: PRT
<213> ORGANISM: Artificial Sequence
<220> FEATURE:
<223> OTHER INFORMATION: 1D05 IgG Light Chain

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Ala
            20                  25                  30

Leu Asn Trp Tyr Gln Gln Lys Pro Gly Lys Ala Pro Lys Leu Leu Ile
        35                  40                  45

Tyr Asn Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Phe Asp Gly Asp Pro Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140
```

```
Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 27
<211> LENGTH: 107
<212> TYPE: PRT
<213> ORGANISM: Artificial Sequence
<220> FEATURE:
<223> OTHER INFORMATION: VL; m2CX1D05

<400> SEQUENCE: 27

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Ser Ala
            20                  25                  30

Leu Asn Trp Tyr Gln Gln Lys Pro Gly Lys Ala Pro Lys Leu Leu Ile
        35                  40                  45

Tyr Asn Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Phe Asp Gly Asp Pro Thr
                85                  90                  95

Phe Gly Gln Gly Thr Lys Val Glu Ile Lys Arg
            100                 105

<210> SEQ ID NO 28
<211> LENGTH: 321
<212> TYPE: DNA
<213> ORGANISM: Artificial Sequence
<220> FEATURE:
<223> OTHER INFORMATION: VL; m2CX1D05

<400> SEQUENCE: 28
gatatccaga tgacccagag cccgtctagc ctgagcgcga gcgtgggtga tcgtgtgacc      60
attacctgca gagcgagcca gggtattcgt tctgctctga attggtacca gcagaaacca     120
ggtaaagcac cgaaactatt aatttataat ggttctactt tgcaaagcgg ggtcccgtcc     180
cgttttagcg gctctggatc cggcactgat tttaccctga ccattagcag cctgcaacct     240
gaagactttg cggtttatta ttgccagcag tttgatggtg atcctacctt tggccagggt     300
acgaaagttg aaattaaacg t                                               321

<210> SEQ ID NO 29
<211> LENGTH: 1371
<212> TYPE: DNA
<213> ORGANISM: Artificial Sequence
<220> FEATURE:
<223> OTHER INFORMATION: 1D05 IgG2m4 Heavy Chain
```

<400> SEQUENCE: 29

```
caggtgcaat tggttcagtc tggcgcggaa gtgaaaaaac cgggcagcag cgtgaaagtg      60
agctgcaaag cctccggagg cacttttaat tctcatgcta tttcttgggt gcgccaagcc     120
cctgggcagg gtctcgagtg gatgggcggt atcaatccga ttcttggcat tgcgaattac     180
gcgcagaagt ttcagggccg ggtgaccatt accgcggatg aaagcaccag caccgcgtat     240
atggaactga gcagcctgcg tagcgaagat acggccgtgt attattgcgc gcgtcattat     300
gagattcaga ttggtcgtta tggtatgaat gtttattatc ttatgtatcg ttttgcttct     360
tggggccaag gcaccctggt gacggttagc tcagcatcca ccaagggccc atccgtcttc     420
cccctggcgc cctgctccag gagcacctcc gagagcacag ccgccctggg ctgcctggtc     480
aaggactact ccccgaacc ggtgacggtg tcgtggaact caggcgccct gaccagcggc     540
gtgcacacct tcccggctgt cctacagtcc tcaggactct actccctcag cagcgtggtg     600
accgtgacct ccagcaactt gggcacgcag acctacacct gcaacgtaga tcacaagccc     660
agcaacacca aggtggacaa gacagttgag cggaaatgct gcgtggagtg cccaccatgc     720
ccagcacctc cagtggccgg accatcagtc ttcctgttcc ccccaaaacc caaggacact     780
ctcatgatct cccggacccc tgaggtcacg tgcgtggtgg tggacgtgag ccaggaagac     840
cccgaggtcc agttcaactg gtacgtggat ggcgtggagg tgcataatgc caagacaaag     900
ccgcgggagg agcagttcaa cagcacgttc cgtgtggtca gcgtcctcac cgtcctgcac     960
caggactggc tgaacggcaa ggagtacaag tgcaaggtct ccaacaaagg cctcccgtcc    1020
tccatcgaga aaaccatctc caaaaccaaa gggcagcccc gagagccaca ggtgtacacc    1080
ctgcccccat cccgggagga gatgaccaag aaccaggtca gcctgacctg cctggtcaaa    1140
ggcttctacc ccagcgacat cgccgtggag tgggagagca atgggcagcc ggagaacaac    1200
tacaagacca cgcctcccat gctggactcc gacggctcct tcttcctcta cagcaagcta    1260
accgtggaca agagcaggtg gcagcagggg aatgtcttct catgctccgt gatgcatgag    1320
gctctgcaca accactacac acagaagagc ctctccctgt ctcctggtaa a             1371
```

<210> SEQ ID NO 30
<211> LENGTH: 639
<212> TYPE: DNA
<213> ORGANISM: Artificial Sequence
<220> FEATURE:
<223> OTHER INFORMATION: 1D05 IgG LIght Chain

<400> SEQUENCE: 30

```
gatatccaga tgacccagag cccgtctagc ctgagcgcga gcgtgggtga tcgtgtgacc      60
attacctgca gcgagcca gggtattcgt tctgctctga attggtacca gcagaaacca     120
ggtaaagcac cgaaactatt aatttataat ggttctactt tgcaaagcgg ggtcccgtcc     180
cgttttagcg gctctggatc cggcactgat tttaccctga ccattagcag cctgcaacct     240
gaagactttg cggtttatta ttgccagcag tttgatggtg atcctacctt tggccagggt     300
acgaaagttg aaattaaacg tacggtggct gcaccatctg tcttcatctt cccgccatct     360
gatgagcagt tgaaatctgg aactgcctct gttgtgtgcc tgctgaataa cttctatccc     420
agagaggcca aagtacagtg gaaggtggat aacgccctcc aatcgggtaa ctcccaggag     480
agtgtcacag agcaggacag caaggacagc acctacagcc tcagcagcac cctgacgctg     540
agcaaagcag actacgagaa acacaaagtc tacgcctgcg aagtcaccca tcagggcctg     600
agctcgcccg tcacaaagag cttcaacagg ggagagtgt                           639
```

<210> SEQ ID NO 31
<211> LENGTH: 8575
<212> TYPE: DNA
<213> ORGANISM: Artificial Sequence
<220> FEATURE:
<223> OTHER INFORMATION: 1D05 IgG2m4 HC Plasmid

<400> SEQUENCE: 31

| | | | | | |
|---|---|---|---|---|---|
| cgatagattg | tcgcacctga | ttgcccgaca | ttatcgcgag | cccatttata | cccatataaa | 60 |
| tcagcatcca | tgttggaatt | taatcgcggc | ctcgagcaag | acgtttcccg | ttgaatatgg | 120 |
| ctcataacac | cccttgtatt | actgtttatg | taagcagaca | gttttattgt | tcatgatgat | 180 |
| atatttttat | cttgtgcaat | gtaacatcag | agattttgag | acacaacgtg | gctttccccc | 240 |
| cccccccatt | attgaagcat | ttatcagggt | tattgtctca | tgagcggata | catatttgaa | 300 |
| tgtatttaga | aaataaaca | aatagggtt | ccgcgcacat | ttccccgaaa | agtgccacct | 360 |
| gacgtctaag | aaaccattat | tatcatgaca | ttaacctata | aaaataggcg | tatcacgagg | 420 |
| ccctttcgtc | tcgcgcgttt | cggtgatgac | ggtgaaaacc | tctgacacat | gcagctcccg | 480 |
| gagacggtca | cagcttgtct | gtaagcggat | gccgggagca | gacaagcccg | tcagggcgcg | 540 |
| tcagcgggtg | ttggcgggtg | tcggggctgg | cttaactatg | cggcatcaga | gcagattgta | 600 |
| ctgagagtgc | accatatgct | taattaacgc | ggggcagtgc | atgtaatccc | ttcagttggt | 660 |
| tggtacaact | tgccaactgg | gccctgttcc | acatgtgaca | cgggggggga | ccaaacacaa | 720 |
| aggggttctc | tgactgtagt | tgacatcctt | ataaatggat | gtgcacattt | gccaacactg | 780 |
| agtggctttc | atcctggagc | agactttgca | gtctgtggac | tgcaacacaa | cattgccttt | 840 |
| atgtgtaact | cttggctgaa | gctcttacac | caatgctggg | ggacatgtac | ctcccagggg | 900 |
| cccaggaaga | ctacgggagg | ctacaccaac | gtcaatcaga | ggggcctgtg | tagctaccga | 960 |
| taagcggacc | ctcaagaggg | cattagcaat | agtgtttata | aggccccctt | gttaaccta | 1020 |
| aacgggtagc | atatgcttcc | cgggtagtag | tatatactat | ccagactaac | cctaattcaa | 1080 |
| tagcatatgt | tacccaacgg | gaagcatatg | ctatcgaatt | agggttagta | aagggtcct | 1140 |
| aaggaacagc | gatatctccc | accccatgag | ctgtcacggt | tttatttaca | tggggtcagg | 1200 |
| attccacgag | ggtagtgaac | catttagtc | acaagggcag | tggctgaaga | tcaaggagcg | 1260 |
| ggcagtgaac | tctcctgaat | cttcgcctgc | ttcttcattc | tccttcgttt | agctaataga | 1320 |
| ataactgctg | agttgtgaac | agtaaggtgt | atgtgaggtg | ctcgaaaaca | aggtttcagg | 1380 |
| tgacgccccc | agaataaaat | ttggacgggg | ggttcagtgg | tggcattgtg | ctatgacacc | 1440 |
| aatataaccc | tcacaaaccc | cttgggcaat | aaatactagt | gtaggaatga | acattctga | 1500 |
| atatctttaa | caatagaaat | ccatggggtg | gggacaagcc | gtaaagactg | gatgtccatc | 1560 |
| tcacacgaat | ttatggctat | gggcaacaca | taatcctagt | gcaatatgat | actggggtta | 1620 |
| ttaagatgtg | tcccaggcag | ggaccaagac | aggtgaacca | tgttgttaca | ctctatttgt | 1680 |
| aacaagggga | aagagagtgg | acgccgacag | cagcggactc | cactggttgt | ctctaacacc | 1740 |
| cccgaaaatt | aaacgggct | ccacgccaat | ggggcccata | acaaagaca | agtggccact | 1800 |
| cttttttttg | aaattgtgga | gtgggggcac | gcgtcagccc | ccacacgccg | ccctgcggtt | 1860 |
| ttggactgta | aaataagggt | gtaataactt | ggctgattgt | aaccccgcta | accactgcgg | 1920 |
| tcaaaccact | tgcccacaaa | accactaatg | caccccggg | gaatacctgc | ataagtaggg | 1980 |
| gggcgggcca | agatagggc | gcgattgctg | cgatctggag | gacaaattac | acacacttgc | 2040 |
| gcctgagcgc | caagcacagg | gttgttggtc | ctcatattca | cgaggtcgct | gagagcacgg | 2100 |
| tgggctaatg | ttgccatggg | tagcatatac | tacccaaata | tctggatagc | atatgctatc | 2160 |

```
ctaatctata tctgggtagc ataggctatc ctaatctata tctgggtagc atatgctatc   2220
ctaatctata tctgggtagt atatgctatc ctaatttata tctgggtagc ataggctatc   2280
ctaatctata tctgggtagc atatgctatc ctaatctata tctgggtagt atatgctatc   2340
ctaatctgta tccgggtagc atatgctatc ctaatagaga ttagggtagt atatgctatc   2400
ctaatttata tctgggtagc atatactacc caaatatctg gatagcatat gctatcctaa   2460
tctatatctg ggtagcatat gctatcctaa tctatatctg ggtagcatag gctatcctaa   2520
tctatatctg ggtagcatat gctatcctaa tctatatctg ggtagtatat gctatcctaa   2580
tttatatctg ggtagcatag gctatcctaa tctatatctg ggtagcatat gctatcctaa   2640
tctatatctg ggtagtatat gctatcctaa tctgtatccg ggtagcatat gctatcctca   2700
tgcatataca gtcagcatat gatacccagt agtagagtgg gagtgctatc ctttgcatat   2760
gccgccacct cccaaggggg cgtgaatttt cgctgcttgt ccttttcctg cggcgcgccg   2820
tttaaacatt taaatggatc cgcaccatat gcggtgtgaa ataccgcaca gatgcgtaag   2880
gagaaaatac cgcatcagat tggctattgg ccattgcata cgttgtatcc atatcataat   2940
atgtacattt atattggctc atgtccaaca ttaccgccat gttgacattg attattgact   3000
agttattaat agtaatcaat tacggggtca ttagttcata gcccatatat ggagttccgc   3060
gttacataac ttacggtaaa tggcccgcct ggctgaccgc ccaacgaccc ccgcccattg   3120
acgtcaataa tgacgtatgt tcccatagta acgccaatag ggactttcca ttgacgtcaa   3180
tgggtggagt atttacggta aactgcccac ttggcagtac atcaagtgta tcatatgcca   3240
agtacgcccc ctattgacgt caatgacggt aaatggcccg cctggcatta tgcccagtac   3300
atgaccttat gggactttcc tacttggcag tacatctacg tattagtcat cgctattacc   3360
atggtgatgc ggttttggca gtacatcaat gggcgtggat agcggtttga ctcacgggga   3420
tttccaagtc tccaccccat tgacgtcaat gggagtttgt tttggcacca aaatcaacgg   3480
gactttccaa aatgtcgtaa caactccgcc ccattgacgc aaatgggcgg taggcgtgta   3540
cggtgggagg tctatataag cagagctcgt ttagtgaacc gtcagatcgc ctggagacgc   3600
catccacgct gttttgacct ccatagaaga caccgggacc gatccagcct ccgcggccgg   3660
gaacggtgca ttggaacgcg gattccccgt gccaagagtg acgtaagtac cgcctataga   3720
gtctataggc ccaccccctt ggcttcttat gcatgctata ctgttttttgg cttggggtct   3780 atacaccccc gcttcctcat gttataggtg atggtatagc ttagcctata ggtgtgggtt   3840
attgaccatt attgaccact cccctattgg tgacgatact ttccattact aatccataac   3900
atggctcttt gccacaactc tctttattgg ctatatgcca atacactgtc cttcagagac   3960
tgacacggac tctgtatttt tacaggatgg ggtctcattt attatttaca aattcacata   4020
tacaacacca ccgtccccag tgcccgcagt ttttattaaa cataacgtgg gatctccacg   4080
cgaatctcgg gtacgtgttc cggacatggg ctcttctccg gtagcggcgg agcttctaca   4140 tccgagcccct ggtcccatgc ctccagcggc tcatggtcgc tcggcagctc cttgctccta   4200
acagtggagg ccagacttag gcacagcaca atgcccacca ccaccagtgt gccgcacaag   4260 gccgtggcg tagggtatgt gtctgaaaat gagcgtggag attgggctcg cacgctgac   4320 gcagatggaa gacttaaggc agcggcagaa gaagatgcag gcagctgagt tgttgtattc   4380
tgataagagt cagaggtaac tcccgttgcg gtgctgttaa cggtggaggg cagtgtagtc   4440
tgagcagtac tcgttgctgc cgcgcgcgcc accagacata atagctgaca gactaacaga   4500
ctgttccttt ccatgggtct tttctgcagt caccgtcctt gacacgaagc ttgccgccac   4560
```

```
catggaatgg agctgggtct ttctcttctt cctgtcagta actacaggtg tccactcgca    4620
ggtgcaattg gttcagtctg gcgcggaagt gaaaaaaccg ggcagcagcg tgaaagtgag    4680
ctgcaaagcc tccggaggca cttttaattc tcatgctatt tcttgggtgc gccaagcccc    4740
tgggcagggt ctcgagtgga tgggcggtat caatccgatt cttggcattg cgaattacgc    4800
gcagaagttt cagggccggg tgaccattac cgcggatgaa agcaccagca ccgcgtatat    4860
ggaactgagc agcctgcgta gcgaagatac ggccgtgtat tattgcgcgc gtcattatga    4920
gattcagatt ggtcgttatg gtatgaatgt ttattatctt atgtatcgtt ttgcttcttg    4980
gggccaaggc accctggtga cggttagctc agcatccacc aagggcccat ccgtcttccc    5040
cctggcgccc tgctccagga gcacctccga gagcacagcc gccctgggct gcctggtcaa    5100
ggactacttc cccgaaccgg tgacggtgtc gtggaactca ggcgccctga ccagcggcgt    5160
gcacaccttc ccggctgtcc tacagtcctc aggactctac tccctcagca gcgtggtgac    5220
cgtgacctcc agcaactttg gcacgcagac ctacacctgc aacgtagatc acaagcccag    5280
caacaccaag gtggacaaga cagttgagcg gaaatgctgc gtggagtgcc caccatgccc    5340
agcacctcca gtggccggac catcagtctt cctgttcccc ccaaaaccca aggacactct    5400
catgatctcc cggacccctg aggtcacgtg cgtggtggtg gacgtgagcc aggaagaccc    5460
cgaggtccag ttcaactggt acgtggatgg cgtggaggtg cataatgcca agacaaagcc    5520
gcgggaggag cagttcaaca gcacgttccg tgtggtcagc gtcctcaccg tcctgcacca    5580
ggactggctg aacggcaagg agtacaagtg caaggtctcc aacaaaggcc tcccgtcctc    5640
catcgagaaa accatctcca aaccaaagg gcagccccga gagccacagg tgtacaccct    5700
gcccccatcc cggaggagaa tgaccaagaa ccaggtcagc ctgacctgcc tggtcaaagg    5760
cttctacccc agcgacatcg ccgtggagtg ggagagcaat gggcagccgg agaacaacta    5820
caagaccacg cctcccatgc tggactccga cggctccttc ttcctctaca gcaagctaac    5880
cgtggacaag agcaggtggc agcaggggaa tgtcttctca tgctccgtga tgcatgaggc    5940
tctgcacaac cactacacac agaagagcct ctccctgtct cctggtaaat gagcggccgc    6000
gatctgctgt gccttctagt tgccagccat ctgttgtttg cccctccccc gtgccttcct    6060
tgaccctgga aggtgccact cccactgtcc tttcctaata aaatgaggaa attgcatcgc    6120
attgtctgag taggtgtcat tctattctgg ggggtgggt ggggcagcac agcaagggg    6180 aggattggga agacaatagc aggcatgctg gggatgcggt gggctctatg gccgctgaga    6240 tctgccgct gcggccaggt gctgaagaat tgacccggtt cctcctgggc cagaaagaag    6300
caggcacatc cccttctctg tgacacaccc tgtccacgcc cctggttctt agttccagcc    6360
ccactcatag gacactcata gctcaggagg ctccgccctt caatcccacc cgctaaagta    6420
cttggagcgg tctctcccct cctcatcagc ccaccaaacc aaacctagcc tccaagagtg    6480
ggaagaaatt aaagcaagat aggctattaa gtgcagaggg agagaaaatg cctccaacat    6540
gtgaggaagt aatgagagaa atcatagaat ttcttccgct tcctcgctca ctgactcgct    6600
gcgctcggtc gttcggctgc ggcgagcggt atcagctcac tcaaaggcgg taatacggtt    6660
atccacagaa tcaggggata acgcaggaaa gaacatgtga gcaaaaggcc agcaaaaggc    6720
caggaaccgt aaaaaggccg cgttgctggc gttttccat aggctccgcc cccctgacga    6780
gcatcacaaa aatcgacgct caagtcagag gtggcgaaac ccgacaggac tataaagata    6840
ccaggcgttt cccctggaa gctccctcgt gcgctctcct gttccgaccc tgccgcttac    6900
cggatacctg tccgccttc tcccttcggg aagcgtggcg ctttctcaat gctcacgctg    6960
```

| | |
|---|---|
| taggtatctc agttcggtgt aggtcgttcg ctccaagctg ggctgtgtgc acgaaccccc | 7020 |
| cgttcagccc gaccgctgcg ccttatccgg taactatcgt cttgagtcca acccggtaag | 7080 |
| acacgactta tcgccactgg cagcagccac tggtaacagg attagcagag cgaggtatgt | 7140 |
| aggcggtgct acagagttct tgaagtggtg gcctaactac ggctacacta aggacagt | 7200 |
| atttggtatc tgcgctctgc tgaagccagt taccttcgga aaaagagttg gtagctcttg | 7260 |
| atccggcaaa caaccaccg ctggtagcgg tggttttttt gtttgcaagc agcagattac | 7320 |
| gcgcagaaaa aaggatctc aagaagatcc tttgatcttt tctacggggt ctgacgctca | 7380 |
| gtggaacgaa aactcacgtt aagggatttt ggtcatgaga ttatcaaaaa ggatcttcac | 7440 |
| ctagatcctt ttaaattaaa aatgaagttt taaatcaatc taaagtatat atgagtaaac | 7500 |
| ttggtctgac agttaccaat gcttaatcag tgaggcacct atctcagcga tctgtctatt | 7560 |
| tcgttcatcc atagttgcct gactccgggg ggggggggcg ctgaggtctg cctcgtgaag | 7620 |
| aaggtgttgc tgactcatac caggcctgaa tcgccccatc atccagccag aaagtgaggg | 7680 |
| agccacggtt gatgagagct tgttgtagg tggaccagtt ggtgattttg aacttttgct | 7740 |
| ttgccacgga acgtctgcg ttgtcggaa gatgcgtgat ctgatccttc aactcagcaa | 7800 |
| aagttcgatt tattcaacaa agccgccgtc ccgtcaagtc agcgtaatgc tctgccagtg | 7860 |
| ttacaaccaa ttaaccaatt ctgattagaa aaactcatcg agcatcaaat gaaactgcaa | 7920 |
| tttattcata tcaggattat caataccata tttttgaaaa agccgtttct gtaatgaagg | 7980 |
| agaaaactca ccgaggcagt tccataggat ggcaagatcc tggtatcggt ctgcgattcc | 8040 |
| gactcgtcca acatcaatac aacctattaa tttccctcg tcaaaaataa ggttatcaag | 8100 |
| tgagaaatca ccatgagtga cgactgaatc cggtgagaat ggcaaaagct tatgcatttc | 8160 |
| tttccagact tgttcaacag gccagccatt acgctcgtca tcaaaatcac tcgcatcaac | 8220 |
| caaaccgtta ttcattcgtg attgcgcctg agcgagacga atacgcgat cgctgttaaa | 8280 |
| aggacaatta caaacaggaa tcgaatgcaa ccggcgcagg aacactgcca gcgcatcaac | 8340 |
| aatattttca cctgaatcag gatattcttc taatacctgg aatgctgttt tcccggggat | 8400 |
| cgcagtggtg agtaaccatg catcatcagg agtacggata aaatgcttga tggtcggaag | 8460 |
| aggcataaat tccgtcagcc agtttagtct gaccatctca tctgtaacat cattggcaac | 8520 |
| gctacctttg ccatgtttca gaaacaactc tggcgcatcg gcttcccat acaat | 8575 |

<210> SEQ ID NO 32
<211> LENGTH: 9484
<212> TYPE: DNA
<213> ORGANISM: Artificial Sequence
<220> FEATURE:
<223> OTHER INFORMATION: 1D05 IgG LC Plasmid

<400> SEQUENCE: 32

| | |
|---|---|
| cgatagattg tcgcacctga ttgcccgaca ttatcgcgag cccatttata cccatataaa | 60 |
| tcagcatcca tgttggaatt taatcgcggc ctcgagcaag acgtttcccg ttgaatatgg | 120 |
| ctcataacac cccttgtatt actgtttatg taagcagaca gttttattgt tcatgatgat | 180 |
| atatttttat cttgtgcaat gtaacatcag agatttgag acacaacgtg ctttccccc | 240 |
| ccccccatt attgaagcat ttatcagggt tattgtctca tgagcggata catatttgaa | 300 |
| tgtatttaga aaataaaca aatagggggtt ccgcgcacat ttccccgaaa agtgccacct | 360 |
| gacgtctaag aaaccattat tatcatgaca ttaacctata aaaataggcg tatcacgagg | 420 |
| cccttcgtc tcgcgcgttt cggtgatgac ggtgaaaacc tctgacacat gcagctcccg | 480 |

-continued

| | |
|---|---|
| gagacggtca cagcttgtct gtaagcggat gccgggagca gacaagcccg tcagggcgcg | 540 |
| tcagcgggtg ttggcgggtg tcggggctgg cttaactatg cggcatcaga gcagattgta | 600 |
| ctgagagtgc accatatgct taattaacgc ggggcagtgc atgtaatccc ttcagttggt | 660 |
| tggtacaact tgccaactgg gccctgttcc acatgtgaca cgggggggga ccaaacacaa | 720 |
| aggggttctc tgactgtagt tgacatcctt ataaatggat gtgcacattt gccaacactg | 780 |
| agtggctttc atcctggagc agactttgca gtctgtggac tgcaacacaa cattgccttt | 840 |
| atgtgtaact cttggctgaa gctcttacac caatgctggg ggacatgtac ctcccagggg | 900 |
| cccaggaaga ctacgggagg ctacaccaac gtcaatcaga ggggcctgtg tagctaccga | 960 |
| taagcggacc ctcaagaggg cattagcaat agtgtttata aggcccccctt gttaaccccta | 1020 |
| aacgggtagc atatgcttcc cgggtagtag tatatactat ccagactaac cctaattcaa | 1080 |
| tagcatatgt tacccaacgg gaagcatatg ctatcgaatt agggttagta aaagggtcct | 1140 |
| aaggaacagc gatatctccc accccatgag ctgtcacggt tttatttaca tggggtcagg | 1200 |
| attccacgag ggtagtgaac cattttagtc acaagggcag tggctgaaga tcaaggagcg | 1260 |
| ggcagtgaac tctcctgaat cttcgcctgc ttcttcattc tccttcgttt agctaataga | 1320 |
| ataactgctg agttgtgaac agtaaggtgt atgtgaggtg ctcgaaaaca aggtttcagg | 1380 |
| tgacgccccc agaataaaat ttggacgggg ggttcagtgg tggcattgtg ctatgacacc | 1440 |
| aatataaccc tcacaaaccc cttgggcaat aaatactagt gtaggaatga acattctga | 1500 |
| atatctttaa caatagaaat ccatgggggtg gggacaagcc gtaaagactg gatgtccatc | 1560 |
| tcacacgaat ttatggctat gggcaacaca taatcctagt gcaatatgat actggggtta | 1620 |
| ttaagatgtg tcccaggcag ggaccaagac aggtgaacca tgttgttaca ctctatttgt | 1680 |
| aacaagggga aagagagtgg acgccgacag cagcggactc cactggttgt ctctaacacc | 1740 |
| cccgaaaatt aaacggggct ccacgccaat ggggcccata acaaagaca agtggccact | 1800 |
| cttttttttg aaattgtgga gtgggggcac gcgtcagccc ccacacgccg ccctgcggtt | 1860 |
| ttggactgta aaataagggt gtaataactt ggctgattgt aaccccgcta accactgcgg | 1920 |
| tcaaaccact tgcccacaaa accactaatg gcaccccggg gaatacctgc ataagtaggt | 1980 |
| gggcgggcca agatagggc gcgattgctg cgatctggag gacaaattac acacacttgc | 2040 |
| gcctgagcgc caagcacagg gttgttggtc ctcatattca cgaggtcgct gagagcacgg | 2100 |
| tgggctaatg ttgccatggg tagcatatac tacccaaata tctggatagc atatgctatc | 2160 |
| ctaatctata tctgggtagc ataggctatc ctaatctata tctgggtagc atatgctatc | 2220 |
| ctaatctata tctgggtagt atatgctatc ctaatttata tctgggtagc ataggctatc | 2280 |
| ctaatctata tctgggtagc atatgctatc ctaatctata tctgggtagt atatgctatc | 2340 |
| ctaatctgta tccgggtagc atatgctatc ctaatagaga ttagggtagt atatgctatc | 2400 |
| ctaatttata tctgggtagc atatactacc caaatatctg gatagcatat gctatcctaa | 2460 |
| tctatatctg ggtagcatat gctatcctaa tctatatctg ggtagcatag gctatcctaa | 2520 |
| tctatatctg ggtagcatat gctatcctaa tctatatctg ggtagtatat gctatcctaa | 2580 |
| tttatatctg gtagcatag gctatcctaa tctatatctg ggtagcatat gctatcctaa | 2640 |
| tctatatctg ggtagtatat gctatcctaa tctgtatccg ggtagcatat gctatcctca | 2700 |
| tgcatataca gtcagcatat gatacccagt agtagagtgg gagtgctatc ctttgcatat | 2760 |
| gccgccacct cccaagggg cgtgaatttt cgctgcttgt cctttttcctg cggcgcgccg | 2820 |
| tttaaacatt taaatggatc cgcaccatat gcggtgtgaa ataccgcaca gatgcgtaag | 2880 |

-continued

```
gagaaaatac cgcatcagat tggctattgg ccattgcata cgttgtatcc atatcataat    2940
atgtacattt atattggctc atgtccaaca ttaccgccat gttgacattg attattgact    3000
agttattaat agtaatcaat tacggggtca ttagttcata gcccatatat ggagttccgc    3060
gttacataac ttacggtaaa tggcccgcct ggctgaccgc ccaacgaccc ccgcccattg    3120
acgtcaataa tgacgtatgt tcccatagta acgccaatag ggactttcca ttgacgtcaa    3180
tgggtggagt atttacggta aactgcccac ttggcagtac atcaagtgta tcatatgcca    3240
agtacgcccc ctattgacgt caatgacggt aaatggcccg cctggcatta tgcccagtac    3300
atgaccttat gggactttcc tacttggcag tacatctacg tattagtcat cgctattacc    3360
atggtgatgc ggttttggca gtacatcaat gggcgtggat agcggtttga ctcacgggga    3420
tttccaagtc tccaccccat tgacgtcaat gggagtttgt tttggcacca aaatcaacgg    3480
gactttccaa aatgtcgtaa caactccgcc ccattgacgc aaatgggcgg taggcgtgta    3540
cggtgggagg tctatataag cagagctcgt ttagtgaacc gtcagatcgc ctggagacgc    3600
catccacgct gttttgacct ccatagaaga caccgggacc gatccagcct ccgcggccgg    3660
gaacggtgca ttggaacgcg gattccccgt gccaagagtg acgtaagtac cgcctataga    3720
gtctataggc ccaccccctt ggcttcttat gcatgctata ctgttttggg cttgggtct     3780 atacaccccc gcttcctcat gttataggtg atggtatagc ttagcctata ggtgggggtt    3840
attgaccatt attgaccact cccctattgg tgacgatact ttccattact aatccataac    3900
atggctcttt gccacaactc tctttattgg ctatatgcca atacactgtc cttcagagac    3960
tgacacggac tctgtatttt tacaggatgg ggtctcattt attatttaca aattcacata    4020
tacaacacca ccgtccccag tgcccgcagt ttttattaaa cataacgtgg gatctccacg    4080
cgaatctcgg gtacgtgttc cggacatggg ctcttctccg gtagcggcgg agcttctaca    4140
tccgagccct gctcccatgc ctccagcgac tcatggtcgc tcggcagctc cttgctccta    4200
acagtggagg ccagacttag gcacagcacg atgcccacca ccaccagtgt gccgcacaag    4260
gccgtggcgg tagggtatgt gtctgaaaat gagcgtggag attgggctcg cacggctgac    4320
gcagatggaa gacttaaggc agcggcagaa gaagatgcag gcagctgagt tgttgtattc    4380
tgataagagt cagaggtaac tcccgttgcg gtgctgttaa cggtggaggg cagtgtagtc    4440
tgagcagtac tcgttgctgc cgcgcgcgcc accagacata atagctgaca gactaacaga    4500
ctgttccttt ccatgggtct tttctgcagt caccgtcctt gacacgaagc ttgccgccac    4560
catgagtgtg cccactcagg tcctgggggtt gctgctgctg tggcttacag atgccagatg    4620
cgatatccag atgacccaga gcccgtctag cctgagcgcg agcgtgggtg atcgtgtgac    4680
cattacctgc agagcgagcc agggtattcg ttctgctctg aattggtacc agcagaaacc    4740
aggtaaagca ccgaaactat taatttataa tggttctact ttgcaaagcg gggtcccgtc    4800
ccgttttagc ggctctggat ccggcactga tttttaccctg accattagca gcctgcaacc    4860
tgaagacttt gcggtttatt attgccagca gtttgatggt gatcctacct ttggccaggg    4920
tacgaaagtt gaaattaaac gtacggtggc tgcaccatct gtcttcatct cccgccatc     4980 tgatgagcag ttgaaatctg gaactgcctc tgttgtgtgc ctgctgaata acttctatcc    5040
cagagaggcc aaagtacagt ggaaggtgga taacgccctc caatcgggta actcccagga    5100
gagtgtcaca gagcaggaca gcaaggacag cacctacagc ctcagcagca ccctgacgct    5160
gagcaaagca gactacgaga aacacaaagt ctacgcctgc gaagtcaccc atcagggcct    5220
gagctcgccc gtcacaaaga gcttcaacag gggagagtgt taggcggccg cgatctgctg    5280
```

```
tgccttctag ttgccagcca tctgttgttt gcccctcccc cgtgccttcc ttgaccctgg   5340
aaggtgccac tcccactgtc ctttcctaat aaaatgagga aattgcatcg cattgtctga   5400
gtaggtgtca ttctattctg gggggtgggg tggggcagca cagcaagggg gaggattggg   5460
aagacaatag caggcatgct ggggatgcgg tgggctctat ggccgctgag atctggccgc   5520
tgcggccctg tggaatgtgt gtcagttagg gtgtggaaag tccccaggct ccccagcagg   5580
cagaagtatg caaagcatgc atctcaatta gtcagcaacc aggtgtggaa agtccccagg   5640
ctccccagca ggcagaagta tgcaaagcat gcatctcaat tagtcagcaa ccatagtccc   5700
gcccctaact ccgccatcc cgcccctaac tccgcccagt tccgcccatt ctccgcccca   5760
tggctgacta atttttttta tttatgcaga ggccgaggcc gcctctgcct ctgagctatt   5820
ccagaagtag tgaggaggct tttttggagg cctaggcttt tgcaaaaagc tgtcgaccac   5880
catggccacc tcagcaagtt cccacttgaa caaaaacatc aagcaaatgt acttgtgcct   5940
gccccagggt gagaaagtcc aagccatgta tatctgggtt gatggtactg agaaggact    6000 gcgctgcaaa acccgcaccc tggactgtga gcccaagtgt gtagaagagt tacctgagtg   6060
gaattttgat ggctctagta cctttcagtc tgagggctcc aacagtgaca tgtatctcag   6120
ccctgttgcc atgtttcggg accccttccg cagagatccc aacaagctgg tgttctgtga   6180
agttttcaag tacaaccgga agcccgcaga gaccaattta aggcactcgt gtaaacggat   6240
aatggacatg gtgagcaacc agcacccctg gtttggaatg gaacaggagt atactctgat   6300
gggaacagat gggcaccctt ttggttggcc ttccaatggc tttcctggac cccaaggtcc   6360
gtattactgt ggtgtgggcg cagacaaagc ctatggcagg gacatcgtgg aggctcacta   6420
ccgcgcctgc ttgtatgctg gggtcaagat tacaggaaca aatgctgagg tcatgcctgc   6480
ccagtgggag ttccaaatag gaccctgtga aggaatccgc atgggagatc atctctgggt   6540
ggcccgtttc atcttgcatc gagtatgtga agactttggg gtaatagcaa cctttgaccc   6600
caagcccatt cctgggaact ggaatggtgc aggctgccat accaactttta gcaccaaggc   6660 catgcgggag gagaatggtc tgaagcacat cgaggaggcc atcgagaaac taagcaagcg   6720
gcaccggtat cacattcgag cctacgatcc caagggggggc ctggacaatg cccgtggtct   6780
gactgggttc cacgaaacgt ccaacatcaa cgacttttct gctggtgtcg ccaatcgcag   6840
tgccagcatc cgcattcccc ggactgtcgg ccaggagaag aaaggttact ttgaagaccg   6900
ccgcccctct gccaattgtg accccttttgc agtgacagaa gccatcgtcc gcacatgcct   6960
tctcaatgag actggcgacg agcccttcca atacaaaaac taagtcgaca acttgtttat   7020
tgcagcttat aatggttaca ataaagcaa tagcatcaca aatttcacaa ataaagcatt   7080
tttttcactg cattctagtt gtggtttgtc caaactcatc aatgtatctt atcatgtctg   7140
gatcggcgcg ccggccgctg cggccaggtg ctgaagaatt gacccggttc ctcctgggcc   7200
agaaagaagc aggcacatcc ccttctctgt gacacaccct gtccacgccc ctggttctta   7260
gttccagccc cactcatagg acactcatag ctcaggaggg ctccgccttc aatcccaccc   7320
gctaaagtac ttggagcggt ctctccctcc ctcatcagcc caccaaacca aacctagcct   7380
ccaagagtgg gaagaaatta aagcaagata ggctattaag tgcagaggga gagaaaatgc   7440
ctccaacatg tgaggaagta atgagagaaa tcatagaatt tcttccgctt cctcgctcac   7500
tgactcgctg cgctcggtcg ttcggctgcg gcgagcggta tcagctcact caaaggcggt   7560
aatacggtta tccacagaat caggggataa cgcaggaaag aacatgtgag caaaaggcca   7620
gcaaaaggcc aggaaccgta aaaaggccgc gttgctggcg ttttttccata ggctccgccc   7680
```

-continued

```
ccctgacgag catcacaaaa atcgacgctc aagtcagagg tggcgaaacc cgacaggact      7740
ataaagatac caggcgtttc ccctggaag ctccctcgtg cgctctcctg ttccgaccct       7800
gccgcttacc ggatacctgt ccgccttcct cccttcggga agcgtggcgc tttctcaatg      7860
ctcacgctgt aggtatctca gttcggtgta ggtcgttcgc tccaagctgg gctgtgtgca      7920
cgaaccccc gttcagcccg accgctgcgc cttatccggt aactatcgtc ttgagtccaa       7980
cccggtaaga cacgacttat cgccactggc agcagccact ggtaacagga ttagcagagc      8040
gaggtatgta ggcggtgcta cagagttctt gaagtggtgg cctaactacg gctacactag      8100
aaggacagta tttggtatct gcgctctgct gaagccagtt accttcggaa aaagagttgg      8160
tagctcttga tccggcaaac aaaccaccgc tggtagcggt ggttttttg tttgcaagca       8220
gcagattacg cgcagaaaaa aaggatctca agaagatcct ttgatctttt ctacggggtc      8280
tgacgctcag tggaacgaaa actcacgtta agggattttg gtcatgagat tatcaaaaag     8340
gatcttcacc tagatccttt taaattaaaa atgaagtttt aaatcaatct aaagtatata      8400
tgagtaaact tggtctgaca gttaccaatg cttaatcagt gaggcaccta tctcagcgat      8460
ctgtctattt cgttcatcca tagttgcctg actccggggg ggggggcgc tgaggtctgc       8520
ctcgtgaaga aggtgttgct gactcatacc aggcctgaat cgccccatca tccagccaga     8580
aagtgaggga gccacggttg atgagagctt tgttgtaggt ggaccagttg gtgattttga     8640
acttttgctt tgccacggaa cggtctgcgt tgtcgggaag atgcgtgatc tgatccttca     8700
actcagcaaa agttcgattt attcaacaaa gccgccgtcc cgtcaagtca gcgtaatgct    8760
ctgccagtgt tacaaccaat taaccaattc tgattagaaa aactcatcga gcatcaaatg    8820
aaactgcaat ttattcatat caggattatc aataccatat ttttgaaaaa gccgtttctg   8880
taatgaagga gaaaactcac cgaggcagtt ccataggatg gcaagatcct ggtatcggtc   8940
tgcgattccg actcgtccaa catcaataca acctattaat ttcccctcgt caaaataag   9000
gttatcaagt gagaaatcac catgagtgac gactgaatcc ggtgagaatg gcaaaagctt    9060
atgcatttct ttccagactt gttcaacagg ccagccatta cgctcgtcat caaaatcact    9120
cgcatcaacc aaaccgttat tcattcgtga ttgcgcctga gcgagacgaa atacgcgatc    9180
gctgttaaaa ggacaattac aaacaggaat cgaatgcaac cggcgcagga acactgccag   9240
cgcatcaaca atattttcac ctgaatcagg atattcttct aatacctgga atgctgtttt   9300
cccggggatc gcagtggtga gtaaccatgc atcatcagga gtacggataa aatgcttgat   9360
ggtcggaaga ggcataaatt ccgtcagcca gtttagtctg accatctcat ctgtaacatc   9420
attggcaacg ctacctttgc catgtttcag aaacaactct ggcgcatcgg cttcccata    9480
caat                                                                9484
```

```
<210> SEQ ID NO 33
<211> LENGTH: 34
<212> TYPE: DNA
<213> ORGANISM: Artificial Sequence
<220> FEATURE:
<223> OTHER INFORMATION: Primer

<400> SEQUENCE: 33
acagatgcca gatgcgatat ccagatgacc caga                                34

<210> SEQ ID NO 34
<211> LENGTH: 36
<212> TYPE: DNA
<213> ORGANISM: Artificial Sequence
```

```
<220> FEATURE:
<223> OTHER INFORMATION: Primer

<400> SEQUENCE: 34
tgcagccacc gtacgtttaa tttcaacttt cgtacc                                   36

<210> SEQ ID NO 35
<211> LENGTH: 36
<212> TYPE: DNA
<213> ORGANISM: Artificial Sequence
<220> FEATURE:
<223> OTHER INFORMATION: Primer

<400> SEQUENCE: 35
acaggtgtcc actcgcaggt gcaattggtt cagtct                                   36

<210> SEQ ID NO 36
<211> LENGTH: 36
<212> TYPE: DNA
<213> ORGANISM: Artificial Sequence
<220> FEATURE:
<223> OTHER INFORMATION: Primer

<400> SEQUENCE: 36
gcccttggtg gatgctgagc taaccgtcac cagggt                                   36

<210> SEQ ID NO 37
<211> LENGTH: 6
<212> TYPE: PRT
<213> ORGANISM: Artificial Sequence
<220> FEATURE:
<223> OTHER INFORMATION: Epitope Domain

<400> SEQUENCE: 37

Arg Glu Ile Glu Gly Arg
 1               5

<210> SEQ ID NO 38
<211> LENGTH: 585
<212> TYPE: PRT
<213> ORGANISM: Homo Sapiens

<400> SEQUENCE: 38
```

Ser Ile Pro Trp Asn Leu Glu Arg Ile Thr Pro Pro Arg Tyr Arg Ala
 1               5                  10                  15

Asp Glu Tyr Gln Pro Pro Asp Gly Gly Ser Leu Val Glu Val Tyr Leu
             20                  25                  30

Leu Asp Thr Ser Ile Gln Ser Asp His Arg Glu Ile Glu Gly Arg Val
         35                  40                  45

Met Val Thr Asp Phe Glu Asn Val Pro Glu Glu Asp Gly Thr Arg Phe
     50                  55                  60

His Arg Gln Ala Ser Lys Cys Asp Ser His Gly Thr His Leu Ala Gly
 65                  70                  75                  80

Val Val Ser Gly Arg Asp Ala Gly Val Ala Lys Gly Ala Ser Met Arg
                 85                  90                  95

Ser Leu Arg Val Leu Asn Cys Gln Gly Lys Gly Thr Val Ser Gly Thr
            100                 105                 110

Leu Ile Gly Leu Glu Phe Ile Arg Lys Ser Gln Leu Val Gln Pro Val
        115                 120                 125

Gly Pro Leu Val Val Leu Leu Pro Leu Ala Gly Gly Tyr Ser Arg Val
    130                 135                 140

```
Leu Asn Ala Ala Cys Gln Arg Leu Ala Arg Ala Gly Val Val Leu Val
145                 150                 155                 160

Thr Ala Ala Gly Asn Phe Arg Asp Asp Ala Cys Leu Tyr Ser Pro Ala
            165                 170                 175

Ser Ala Pro Glu Val Ile Thr Val Gly Ala Thr Asn Ala Gln Asp Gln
        180                 185                 190

Pro Val Thr Leu Gly Thr Leu Gly Thr Asn Phe Gly Arg Cys Val Asp
    195                 200                 205

Leu Phe Ala Pro Gly Glu Asp Ile Ile Gly Ala Ser Ser Asp Cys Ser
210                 215                 220

Thr Cys Phe Val Ser Gln Ser Gly Thr Ser Gln Ala Ala Ala His Val
225                 230                 235                 240

Ala Gly Ile Ala Ala Met Met Leu Ser Ala Glu Pro Glu Leu Thr Leu
            245                 250                 255

Ala Glu Leu Arg Gln Arg Leu Ile His Phe Ser Ala Lys Asp Val Ile
        260                 265                 270

Asn Glu Ala Trp Phe Pro Glu Asp Gln Arg Val Leu Thr Pro Asn Leu
        275                 280                 285

Val Ala Ala Leu Pro Pro Ser Thr His Gly Ala Gly Trp Gln Leu Phe
290                 295                 300

Cys Arg Thr Val Trp Ser Ala His Ser Gly Pro Thr Arg Met Ala Thr
305                 310                 315                 320

Ala Ile Ala Arg Cys Ala Pro Asp Glu Glu Leu Leu Ser Cys Ser Ser
            325                 330                 335

Phe Ser Arg Ser Gly Lys Arg Gly Glu Arg Met Glu Ala Gln Gly
        340                 345                 350

Gly Lys Leu Val Cys Arg Ala His Asn Ala Phe Gly Gly Glu Gly Val
        355                 360                 365

Tyr Ala Ile Ala Arg Cys Cys Leu Leu Pro Gln Ala Asn Cys Ser Val
370                 375                 380

His Thr Ala Pro Pro Ala Glu Ala Ser Met Gly Thr Arg Val His Cys
385                 390                 395                 400

His Gln Gln Gly His Val Leu Thr Gly Cys Ser Ser His Trp Glu Val
            405                 410                 415

Glu Asp Leu Gly Thr His Lys Pro Pro Val Leu Arg Pro Arg Gly Gln
        420                 425                 430

Pro Asn Gln Cys Val Gly His Arg Glu Ala Ser Ile His Ala Ser Cys
        435                 440                 445

Cys His Ala Pro Gly Leu Glu Cys Lys Val Lys Glu His Gly Ile Pro
450                 455                 460

Ala Pro Gln Glu Gln Val Thr Val Ala Cys Glu Gly Trp Thr Leu
465                 470                 475                 480

Thr Gly Cys Ser Ala Leu Pro Gly Thr Ser His Val Leu Gly Ala Tyr
            485                 490                 495

Ala Val Asp Asn Thr Cys Val Val Arg Ser Arg Asp Val Ser Thr Thr
        500                 505                 510

Gly Ser Thr Ser Glu Glu Ala Val Thr Ala Val Ala Ile Cys Cys Arg
        515                 520                 525

Ser Arg His Leu Ala Gln Ala Ser Gln Glu Leu Gln Lys Gly Asn Ser
530                 535                 540

Ala Asp Ile Gln His Ser Gly Gly Arg Ser Ser Leu Glu Gly Pro Arg
545                 550                 555                 560
```

```
Phe Glu Gly Lys Pro Ile Pro Asn Pro Leu Leu Gly Leu Asp Ser Thr
            565                 570                 575

Arg Thr Gly His His His His His
            580             585
```

<210> SEQ ID NO 39
<211> LENGTH: 53
<212> TYPE: PRT
<213> ORGANISM: Artificial Sequence
<220> FEATURE:
<223> OTHER INFORMATION: Human Epitope Area

<400> SEQUENCE: 39

```
Ser Ile Pro Trp Asn Leu Glu Arg Ile Thr Pro Pro Arg Tyr Arg Ala
1               5                   10                  15

Asp Glu Tyr Gln Pro Pro Asp Gly Gly Ser Leu Val Glu Val Tyr Leu
            20                  25                  30

Leu Asp Thr Ser Ile Gln Ser Asp His Arg Glu Ile Glu Gly Arg Val
        35                  40                  45

Met Val Thr Asp Phe
    50
```

<210> SEQ ID NO 40
<211> LENGTH: 37
<212> TYPE: PRT
<213> ORGANISM: Artificial Sequence
<220> FEATURE:
<223> OTHER INFORMATION: Consensus Epitope Area

<400> SEQUENCE: 40

```
Ser Ile Pro Trp Asn Leu Glu Arg Ile Pro Glu Pro Asp Gly Ser Val
1               5                   10                  15

Glu Val Tyr Leu Leu Asp Thr Ser Ile Gln His Arg Glu Ile Glu Gly
            20                  25                  30

Arg Val Thr Asp Phe
        35
```

<210> SEQ ID NO 41
<211> LENGTH: 53
<212> TYPE: PRT
<213> ORGANISM: Mouse

<400> SEQUENCE: 41

```
Ser Ile Pro Trp Asn Leu Glu Arg Ile Ile Pro Ala Trp His Gln Thr
1               5                   10                  15

Glu Glu Asp Arg Ser Pro Asp Gly Ser Ser Gln Val Glu Val Tyr Leu
            20                  25                  30

Leu Asp Thr Ser Ile Gln Gly Ala His Arg Glu Ile Glu Gly Arg Val
        35                  40                  45

Thr Ile Thr Asp Phe
    50
```

<210> SEQ ID NO 42
<211> LENGTH: 5
<212> TYPE: PRT
<213> ORGANISM: Artificial Sequence
<220> FEATURE:
<223> OTHER INFORMATION: Secondary Footprint Epitope

<400> SEQUENCE: 42

```
Arg Tyr Arg Ala Asp
1               5
```

```
<210> SEQ ID NO 43
<211> LENGTH: 10
<212> TYPE: PRT
<213> ORGANISM: Artificial Sequence
<220> FEATURE:
<223> OTHER INFORMATION: 1D05 Antibody Variant VH CDR1 Sequence
<221> NAME/KEY: VARIANT
<222> LOCATION: 6
<223> OTHER INFORMATION: Xaa = Ser or Asn
<221> NAME/KEY: VARIANT
<222> LOCATION: 7
<223> OTHER INFORMATION: Xaa = His, Asp, Tyr, Phe or Glu

<400> SEQUENCE: 43

Gly Gly Thr Phe Asn Xaa Xaa Ala Ile Ser
 1               5                  10

<210> SEQ ID NO 44
<211> LENGTH: 20
<212> TYPE: PRT
<213> ORGANISM: Artificial Sequence
<220> FEATURE:
<223> OTHER INFORMATION: 1D05 Antibody Variant VH CDR2 Sequence
<221> NAME/KEY: VARIANT
<222> LOCATION: 6
<223> OTHER INFORMATION: Xaa = Asn or Ile
<221> NAME/KEY: VARIANT
<222> LOCATION: 8
<223> OTHER INFORMATION: Xaa = Ile, Asn, Ser, Gly or Tyr
<221> NAME/KEY: VARIANT
<222> LOCATION: 9
<223> OTHER INFORMATION: Xaa = Leu or Asn
<221> NAME/KEY: VARIANT
<222> LOCATION: 11
<223> OTHER INFORMATION: Xaa = Ile, Asp, Thr, Asn, Ser or Gly
<221> NAME/KEY: VARIANT
<222> LOCATION: 12
<223> OTHER INFORMATION: Xaa = Ala or Thr

<400> SEQUENCE: 44

Trp Met Gly Gly Ile Xaa Pro Xaa Xaa Gly Xaa Xaa Asn Tyr Ala Gln
 1               5                  10                  15

Lys Phe Gln Gly
            20

<210> SEQ ID NO 45
<211> LENGTH: 22
<212> TYPE: PRT
<213> ORGANISM: Artificial Sequence
<220> FEATURE:
<223> OTHER INFORMATION: 1D05 Antibody Variant VH CDR3 Sequence
<221> NAME/KEY: VARIANT
<222> LOCATION: 1
<223> OTHER INFORMATION: Xaa = His, Tyr, Phe or Glu
<221> NAME/KEY: VARIANT
<222> LOCATION: 4
<223> OTHER INFORMATION: Xaa = Ile or Ser
<221> NAME/KEY: VARIANT
<222> LOCATION: 5
<223> OTHER INFORMATION: Xaa = Gln, Gly or Arg
<221> NAME/KEY: VARIANT
<222> LOCATION: 6
<223> OTHER INFORMATION: Xaa = Ile or Val
<221> NAME/KEY: VARIANT
<222> LOCATION: 11
<223> OTHER INFORMATION: Xaa = Met or Leu
<221> NAME/KEY: VARIANT
<222> LOCATION: (12)...(12)
<223> OTHER INFORMATION: Xaa = Asn or Thr
<221> NAME/KEY: VARIANT
<222> LOCATION: (13)...(13)
<223> OTHER INFORMATION: Xaa = Val or Arg
<221> NAME/KEY: VARIANT
<222> LOCATION: (16)...(16)
<223> OTHER INFORMATION: Xaa = Leu, Phe or Tyr
```

<221> NAME/KEY: VARIANT
<222> LOCATION: (17)...(17)
<223> OTHER INFORMATION: Xaa = Met, Tyr, Leu or Phe
<221> NAME/KEY: VARIANT
<222> LOCATION: (19)...(19)
<223> OTHER INFORMATION: Xaa = Arg, Gly or Tyr
<221> NAME/KEY: VARIANT
<222> LOCATION: (20)...(20)
<223> OTHER INFORMATION: Xaa = Phe or Leu
<221> NAME/KEY: VARIANT
<222> LOCATION: (21)...(21)
<223> OTHER INFORMATION: Xaa = Ala or Asp
<221> NAME/KEY: VARIANT
<222> LOCATION: (22)...(22)
<223> OTHER INFORMATION: Xaa = Ser, Ala, Leu or Val

<400> SEQUENCE: 45

```
Xaa Tyr Glu Xaa Xaa Xaa Gly Arg Tyr Gly Xaa Xaa Xaa Tyr Tyr Xaa
 1               5                  10                  15

Xaa Tyr Xaa Xaa Xaa Xaa
            20
```

<210> SEQ ID NO 46
<211> LENGTH: 11
<212> TYPE: PRT
<213> ORGANISM: Artificial Sequence
<220> FEATURE:
<223> OTHER INFORMATION: 1D05 Antibody Variant VL CDR1 Sequence
<221> NAME/KEY: VARIANT
<222> LOCATION: 5
<223> OTHER INFORMATION: Xaa = Gly, Ser, Asp or Asn
<221> NAME/KEY: VARIANT
<222> LOCATION: 7
<223> OTHER INFORMATION: Xaa = Arg or Gln
<221> NAME/KEY: VARIANT
<222> LOCATION: 8
<223> OTHER INFORMATION: Xaa = Ser, Asn, Thr, Arg or Lys
<221> NAME/KEY: VARIANT
<222> LOCATION: 9
<223> OTHER INFORMATION: Xaa = Ala, Tyr or Asn

<400> SEQUENCE: 46

```
Arg Ala Ser Gln Xaa Ile Xaa Xaa Xaa Leu Asn
 1               5                  10
```

<210> SEQ ID NO 47
<211> LENGTH: 11
<212> TYPE: PRT
<213> ORGANISM: Artificial Sequence
<220> FEATURE:
<223> OTHER INFORMATION: 1D05 Antibody Variant VL CDR2 Sequence
<221> NAME/KEY: VARIANT
<222> LOCATION: 5
<223> OTHER INFORMATION: Xaa = Asn, Asp, Tyr, Thr, Ala,  Gly or Gln
<221> NAME/KEY: VARIANT
<222> LOCATION: 6
<223> OTHER INFORMATION: Xaa = Gly or Ala
<221> NAME/KEY: VARIANT
<222> LOCATION: 8
<223> OTHER INFORMATION: Xaa = Thr or Arg

<400> SEQUENCE: 47

```
Leu Leu Ile Tyr Xaa Xaa Ser Xaa Leu Gln Ser
 1               5                  10
```

<210> SEQ ID NO 48
<211> LENGTH: 7
<212> TYPE: PRT
<213> ORGANISM: Artificial Sequence
<220> FEATURE:
<223> OTHER INFORMATION: 1D05 Antibody Variant VL CDR3 Sequence

```
<221> NAME/KEY: VARIANT
<222> LOCATION: 3
<223> OTHER INFORMATION: Xaa = Phe or Tyr
<221> NAME/KEY: VARIANT
<222> LOCATION: 4
<223> OTHER INFORMATION: Xaa = Asp or Asn, Gly, Tyr or Ser
<221> NAME/KEY: VARIANT
<222> LOCATION: 5
<223> OTHER INFORMATION: Xaa = Gly, Ser, Asn or Arg

<400> SEQUENCE: 48

Gln Gln Xaa Xaa Xaa Asp Pro
 1               5

<210> SEQ ID NO 49
<211> LENGTH: 107
<212> TYPE: PRT
<213> ORGANISM: Artificial Sequence
<220> FEATURE:
<223> OTHER INFORMATION: VL; 1D05 VARIANT SEQUENCE
<221> NAME/KEY: VARIANT
<222> LOCATION: 28
<223> OTHER INFORMATION: Xaa = Gly, Ser, Asp or Asn
<221> NAME/KEY: VARIANT
<222> LOCATION: 30
<223> OTHER INFORMATION: Xaa = Arg or Gln
<221> NAME/KEY: VARIANT
<222> LOCATION: 31
<223> OTHER INFORMATION: Xaa = Ser, Asn, Thr, Arg or Lys
<221> NAME/KEY: VARIANT
<222> LOCATION: 32
<223> OTHER INFORMATION: Xaa = Ala, Tyr or Asn
<221> NAME/KEY: VARIANT
<222> LOCATION: 50
<223> OTHER INFORMATION: Asn, Asp, Tyr, Thr, Ala, Gly or Gln
<221> NAME/KEY: VARIANT
<222> LOCATION: (51)...(51)
<223> OTHER INFORMATION: Xaa = Gly or Ala
<221> NAME/KEY: VARIANT
<222> LOCATION: (53)...(53)
<223> OTHER INFORMATION: Xaa = Thr or Arg
<221> NAME/KEY: VARIANT
<222> LOCATION: (91)...(91)
<223> OTHER INFORMATION: Xaa = Phe or Tyr
<221> NAME/KEY: VARIANT
<222> LOCATION: (92)...(92)
<223> OTHER INFORMATION: Xaa = Asp, Asn, Gly, Tyr or Ser
<221> NAME/KEY: VARIANT
<222> LOCATION: (93)...(93)
<223> OTHER INFORMATION: Xaa = Gly, Ser, Asn or Arg

<400> SEQUENCE: 49

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Xaa Ile Xaa Xaa Xaa
                20                  25                  30

Leu Asn Trp Tyr Gln Gln Lys Pro Gly Lys Ala Pro Lys Leu Leu Ile
             35                  40                  45

Tyr Xaa Xaa Ser Xaa Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Xaa Xaa Xaa Asp Pro Thr
                85                  90                  95

Phe Gly Gln Gly Thr Lys Val Glu Ile Lys Arg
                100                 105
```

```
<210> SEQ ID NO 50
<211> LENGTH: 131
<212> TYPE: PRT
<213> ORGANISM: Artificial Sequence
<220> FEATURE:
<223> OTHER INFORMATION: VH; 1D05 VARIANT SEQUENCE
<221> NAME/KEY: VARIANT
<222> LOCATION: 31
<223> OTHER INFORMATION: Xaa = Ser or Asn
<221> NAME/KEY: VARIANT
<222> LOCATION: 32
<223> OTHER INFORMATION: Xaa = His, Asp, Tyr, Phe or Glu
<221> NAME/KEY: VARIANT
<222> LOCATION: 52
<223> OTHER INFORMATION: Xaa = Asn or Ile
<221> NAME/KEY: VARIANT
<222> LOCATION: 54
<223> OTHER INFORMATION: Xaa = Ile, Asn, Ser, Gly or Tyr
<221> NAME/KEY: VARIANT
<222> LOCATION: 55
<223> OTHER INFORMATION: Xaa = Leu or Asn
<221> NAME/KEY: VARIANT
<222> LOCATION: (57)...(57)
<223> OTHER INFORMATION: Xaa = Ile, Asp, Thr, Asn, Ser or Gly
<221> NAME/KEY: VARIANT
<222> LOCATION: (58)...(58)
<223> OTHER INFORMATION: Xaa = Ala or Thr
<221> NAME/KEY: VARIANT
<222> LOCATION: (99)...(99)
<223> OTHER INFORMATION: Xaa = His, Tyr, Phe or Glu
<221> NAME/KEY: VARIANT
<222> LOCATION: (102)...(102)
<223> OTHER INFORMATION: Xaa = Ile or Ser
<221> NAME/KEY: VARIANT
<222> LOCATION: (103)...(103)
<223> OTHER INFORMATION: Xaa = Gln, Gly or Arg
<221> NAME/KEY: VARIANT
<222> LOCATION: (104)...(104)
<223> OTHER INFORMATION: Xaa = Ile or Val
<221> NAME/KEY: VARIANT
<222> LOCATION: (109)...(109)
<223> OTHER INFORMATION: Xaa = Met or Leu
<221> NAME/KEY: VARIANT
<222> LOCATION: (110)...(110)
<223> OTHER INFORMATION: Xaa = Asn or Thr
<221> NAME/KEY: VARIANT
<222> LOCATION: (111)...(111)
<223> OTHER INFORMATION: Xaa = Val or Arg
<221> NAME/KEY: VARIANT
<222> LOCATION: (114)...(114)
<223> OTHER INFORMATION: Xaa = Leu, Phe or Tyr
<221> NAME/KEY: VARIANT
<222> LOCATION: (115)...(115)
<223> OTHER INFORMATION: Xaa= Met, Tyr, Leu or Phe
<221> NAME/KEY: VARIANT
<222> LOCATION: (117)...(120)
<223> OTHER INFORMATION: Xaa = Arg, Gly or Tyr at position 117; Phe or
      Leu at position 118; Ala or Asp at position 119; Ser,
      Ala, Leu or Val at position 120

<400> SEQUENCE: 50

Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Asn Xaa Xaa
                 20                  25                  30

Ala Ile Ser Trp Val Arg Gln Ala Pro Gly Gln Gly Leu Glu Trp Met
             35                  40                  45

Gly Gly Ile Xaa Pro Xaa Xaa Gly Xaa Xaa Asn Tyr Ala Gln Lys Phe
         50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95
```

```
Ala Arg Xaa Tyr Glu Xaa Xaa Xaa Gly Arg Tyr Gly Xaa Xaa Xaa Tyr
            100                 105                 110

Tyr Xaa Xaa Tyr Xaa Xaa Xaa Trp Gly Gln Gly Thr Leu Val Thr
        115                 120                 125

Val Ser Ser
    130

<210> SEQ ID NO 51
<211> LENGTH: 131
<212> TYPE: PRT
<213> ORGANISM: Artificial Sequence
<220> FEATURE:
<223> OTHER INFORMATION: VH; 1D05 VARIANT SEQUENCE H32Y

<400> SEQUENCE: 51

Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Asn Ser Tyr
             20                  25                  30

Ala Ile Ser Trp Val Arg Gln Ala Pro Gly Gln Gly Leu Glu Trp Met
         35                  40                  45

Gly Gly Ile Asn Pro Ile Leu Gly Ile Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg His Tyr Glu Ile Gln Ile Gly Arg Tyr Gly Met Asn Val Tyr
            100                 105                 110

Tyr Leu Met Tyr Arg Phe Ala Ser Trp Gly Gln Gly Thr Leu Val Thr
        115                 120                 125

Val Ser Ser
    130

<210> SEQ ID NO 52
<211> LENGTH: 131
<212> TYPE: PRT
<213> ORGANISM: Artificial Sequence
<220> FEATURE:
<223> OTHER INFORMATION: VH; 1D05 VARIANT SEQUENCE M48A

<400> SEQUENCE: 52

Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Asn Ser His
             20                  25                  30

Ala Ile Ser Trp Val Arg Gln Ala Pro Gly Gln Gly Leu Glu Trp Ala
         35                  40                  45

Gly Gly Ile Asn Pro Ile Leu Gly Ile Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg His Tyr Glu Ile Gln Ile Gly Arg Tyr Gly Met Asn Val Tyr
            100                 105                 110
```

-continued

Tyr Leu Met Tyr Arg Phe Ala Ser Trp Gly Gln Gly Thr Leu Val Thr
         115                 120                 125

Val Ser Ser
    130

<210> SEQ ID NO 53
<211> LENGTH: 131
<212> TYPE: PRT
<213> ORGANISM: Artificial Sequence
<220> FEATURE:
<223> OTHER INFORMATION: VH; 1D05 VARIANT SEQUENCE M48L

<400> SEQUENCE: 53

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser His
            20                  25                  30

Ala Ile Ser Trp Val Arg Gln Ala Pro Gly Gln Gly Leu Glu Trp Leu
        35                  40                  45

Gly Gly Ile Asn Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Tyr Glu Ile Gln Ile Gly Arg Tyr Gly Met Asn Val Tyr
            100                 105                 110

Tyr Leu Met Tyr Arg Phe Ala Ser Trp Gly Gln Gly Thr Leu Val Thr
         115                 120                 125

Val Ser Ser
    130

<210> SEQ ID NO 54
<211> LENGTH: 131
<212> TYPE: PRT
<213> ORGANISM: Artificial Sequence
<220> FEATURE:
<223> OTHER INFORMATION: VH; 1D05 VARIANT SEQUENCE H99Y

<400> SEQUENCE: 54

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser His
            20                  25                  30

Ala Ile Ser Trp Val Arg Gln Ala Pro Gly Gln Gly Leu Glu Trp Met
        35                  40                  45

Gly Gly Ile Asn Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Glu Ile Gln Ile Gly Arg Tyr Gly Met Asn Val Tyr
            100                 105                 110

Tyr Leu Met Tyr Arg Phe Ala Ser Trp Gly Gln Gly Thr Leu Val Thr
         115                 120                 125

Val Ser Ser
    130

```
<210> SEQ ID NO 55
<211> LENGTH: 131
<212> TYPE: PRT
<213> ORGANISM: Artificial Sequence
<220> FEATURE:
<223> OTHER INFORMATION: VH; 1D05 VARIANT SEQUENCE M48LM109LM115L

<400> SEQUENCE: 55

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser His
                20                  25                  30

Ala Ile Ser Trp Val Arg Gln Ala Pro Gly Gln Gly Leu Glu Trp Leu
            35                  40                  45

Gly Gly Ile Asn Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Tyr Glu Ile Gln Ile Gly Arg Tyr Gly Leu Asn Val Tyr
            100                 105                 110

Tyr Leu Leu Tyr Arg Phe Ala Ser Trp Gly Gln Gly Thr Leu Val Thr
        115                 120                 125

Val Ser Ser
    130

<210> SEQ ID NO 56
<211> LENGTH: 131
<212> TYPE: PRT
<213> ORGANISM: Artificial Sequence
<220> FEATURE:
<223> OTHER INFORMATION: VH; 1D05 VARIANT SEQUENCE M48V

<400> SEQUENCE: 56

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser His
                20                  25                  30

Ala Ile Ser Trp Val Arg Gln Ala Pro Gly Gln Gly Leu Glu Trp Val
            35                  40                  45

Gly Gly Ile Asn Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Tyr Glu Ile Gln Ile Gly Arg Tyr Gly Met Asn Val Tyr
            100                 105                 110

Tyr Leu Met Tyr Arg Phe Ala Ser Trp Gly Gln Gly Thr Leu Val Thr
        115                 120                 125

Val Ser Ser
    130

<210> SEQ ID NO 57
<211> LENGTH: 107
<212> TYPE: PRT
<213> ORGANISM: Artificial Sequence
<220> FEATURE:
<223> OTHER INFORMATION: VL; 1D05 VARIANT SEQUENCE N50D
```

-continued

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Ala
            20                  25                  30

Leu Asn Trp Tyr Gln Gln Lys Pro Gly Lys Ala Pro Lys Leu Leu Ile
        35                  40                  45

Tyr Asp Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Phe Asp Gly Asp Pro Thr
                85                  90                  95

Phe Gly Gln Gly Thr Lys Val Glu Ile Lys Arg
            100                 105

<210> SEQ ID NO 58
<211> LENGTH: 107
<212> TYPE: PRT
<213> ORGANISM: Artificial Sequence
<220> FEATURE:
<223> OTHER INFORMATION: VH; 1D05 VARIANT SEQUENCE N50Q

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Ala
            20                  25                  30

Leu Asn Trp Tyr Gln Gln Lys Pro Gly Lys Ala Pro Lys Leu Leu Ile
        35                  40                  45

Tyr Gln Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Phe Asp Gly Asp Pro Thr
                85                  90                  95

Phe Gly Gln Gly Thr Lys Val Glu Ile Lys Arg
            100                 105

<210> SEQ ID NO 59
<211> LENGTH: 107
<212> TYPE: PRT
<213> ORGANISM: Artificial Sequence
<220> FEATURE:
<223> OTHER INFORMATION: VH; 1D05 VARIANT SEQUENCE N50T

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Ala
            20                  25                  30

Leu Asn Trp Tyr Gln Gln Lys Pro Gly Lys Ala Pro Lys Leu Leu Ile
        35                  40                  45

Tyr Thr Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

-continued

```
Glu Asp Phe Ala Val Tyr Tyr Cys Gln Gln Phe Asp Gly Asp Pro Thr
                85                  90              95
Phe Gly Gln Gly Thr Lys Val Glu Ile Lys Arg
            100             105

<210> SEQ ID NO 60
<211> LENGTH: 107
<212> TYPE: PRT
<213> ORGANISM: Artificial Sequence
<220> FEATURE:
<223> OTHER INFORMATION: VH; 1D05 VARIANT SEQUENCE N50Y

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Ala
            20                  25                  30

Leu Asn Trp Tyr Gln Gln Lys Pro Gly Lys Ala Pro Lys Leu Leu Ile
        35                  40                  45

Tyr Tyr Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Phe Asp Gly Asp Pro Thr
                85                  90              95

Phe Gly Gln Gly Thr Lys Val Glu Ile Lys Arg
            100             105
```

1D05 PCSK9 ANTAGONISTS

CROSS-REFERENCE TO RELATED APPLICATIONS

This application is a divisional of U.S. patent application Ser. No. 12/322,867; filed Feb. 6, 2009; which is herein incorporated by reference in its entirety; and which claims the benefit of U.S. Provisional Application No. 61/063,949, filed on Feb. 7, 2008, and 61/066,577, filed Feb. 21, 2008.

STATEMENT REGARDING FEDERALLY-SPONSORED R&D

Not Applicable.

REFERENCE TO MICROFICHE APPENDIX

Not Applicable.

BACKGROUND OF THE INVENTION

Proprotein convertase subtilisin-kexin type 9 (hereinafter called "PCSK9"), also known as neural apoptosis-regulated convertase 1 ("NARC-1"), is a proteinase K-like subtilase identified as the 9$^{th}$ member of the secretory subtilase family; see Seidah et al., 2003 PNAS 100:928-933. The gene for PCSK9 localizes to human chromosome 1p33-p34.3; Seidah et al., supra. PCSK9 is expressed in cells capable of proliferation and differentiation including, for example, hepatocytes, kidney mesenchymal cells, intestinal ileum, and colon epithelia as well as embryonic brain telencephalon neurons; Seidah et al., supra.

Original synthesis of PCSK9 is in the form of an inactive enzyme precursor, or zymogen, of ~72-kDa which undergoes autocatalytic, intramolecular processing in the endoplasmic reticulum ("ER") to activate its functionality. This internal processing event has been reported to occur at the SSVFAQ↓SIPWNL$^{158}$ motif (SEQ ID NOs: 19 and 20, respectively); Benjannet et al., 2004 J. Biol. Chem. 279:48865-48875. Such internal processing has been reported as a requirement of exit from the ER; Benjannet et al., supra; Seidah et al., supra. The cleaved and, thereby, activated protein is secreted in association with the cleaved peptide; supra.

The sequence for human PCSK9 (~22-kb long with 12 exons encoding a 692 amino acid protein) can be found in one instance at Deposit No. NP_777596.2. Human, mouse and rat PCSK9 nucleic acid sequences have been deposited; see, e.g., GenBank Accession Nos.: AX127530 (also AX207686), NP_705793 (also Q80W65), and P59996, respectively. PCSK9 possesses several domains found in other proprotein convertases, including an N-terminal signal sequence, a pro domain, a catalytic domain and a cysteine-rich C terminal domain. The PCSK9 catalytic domain shares high sequence similarity with the proteinase K family of subtilases and, notably, a catalytic triad of D186, H226 and S386.

PCSK9 is disclosed and/or claimed in several patent publications including, but not limited to the following: PCT Publication Nos. WO 01/31007, WO 01/57081, WO 02/14358, WO 01/98468, WO 02/102993, WO 02/102994, WO 02/46383, WO 02/90526, WO 01/77137, and WO 01/34768; US Publication Nos. US 2004/0009553 and US 2003/0119038, and European Publication Nos. EP 1 440 981, EP 1 067 182, and EP 1 471 152.

PCSK9 has been ascribed a role in the differentiation of hepatic and neuronal cells (Seidah et al., supra.), is highly expressed in embryonic liver, and has been strongly implicated in cholesterol homeostasis. Studies have suggested a specific role for PCSK9 in cholesterol biosynthesis or uptake. In a study of cholesterol-fed rats, Maxwell et al. found that PCSK9 was downregulated in a similar manner to three other genes involved in cholesterol biosynthesis, Maxwell et al., 2003 J. Lipid Res. 44:2109-2119. The expression of PCSK9 has, in fact, been shown to be regulated by sterol regulatory element-binding proteins ("SREBP"), as seen with other genes involved in cholesterol metabolism; supra. Later support for these findings came about through a study of PCSK9 transcriptional regulation which demonstrated that such regulation was quite typical of other genes implicated in lipoprotein metabolism; Dubuc et al., 2004 Arterioscler. Thromb. Vasc. Biol. 24:1454-1459. Statins have been shown to upregulate PCSK9 expression in a manner attributed to the cholesterol-lowering effects of the drugs; supra. Moreover, it has been shown that PCSK9 promoters possess two conserved sites involved in cholesterol regulation, a sterol regulatory element and an Sp1 site; supra.

Several lines of evidence demonstrate that PCSK9, in particular, lowers the amount of hepatic LDLR protein and thus compromises the liver's ability to remove LDL cholesterol from the circulation. Adenovirus-mediated overexpression of PCSK9 in the livers of mice results in the accumulation of circulating LDL-C due to a dramatic loss of hepatic LDLR protein, with no effect on LDLR mRNA levels; Benjannet et al., 2004 J. Biol. Chem. 279:48865-48875; Maxwell & Breslow, 2004 PNAS 101:7100-7105; Park et al., 2004 J. Biol. Chem. 279:50630-50638; and Lalanne et al., 2005 J. Lipid Res. 46:1312-1319. The effect of PCSK9 overexpression on raising circulating LDL-C levels in mice is completely dependent on the expression of LDLR, again, indicating that the regulation of LDL-C by PCSK9 is mediated through downregulation of LDLR protein. In agreement with these findings, mice lacking PCSK9 or in which PCSK9 mRNA has been lowered by antisense oligonucleotide inhibitors have higher levels of hepatic LDLR protein and a greater ability to clear circulating LDL-C; Rashid et al., 2005 PNAS 102:5374-5379; and Graham et al., 2007 J. Lipid Res. 48(4):763-767. In addition, lowering PCSK9 levels in cultured human hepatocytes by siRNA also results in higher LDLR protein levels and an increased ability to take up LDL-C; Benjannet et al., 2004 J. Biol. Chem. 279:48865-48875; and Lalanne et al., 2005 J. Lipid Res. 46:1312-1319. Together, these data indicate that PCSK9 action leads to increased LDL-C by lowering LDLR protein levels.

A number of mutations in the gene PCSK9 have also been conclusively associated with autosomal dominant hypercholesterolemia ("ADH"), an inherited metabolism disorder characterized by marked elevations of low density lipoprotein ("LDL") particles in the plasma which can lead to premature cardiovascular failure; see Abifadel et al., 2003 Nature Genetics 34:154-156; Timms et al., 2004 Hum. Genet. 114:349-353; Leren, 2004 Clin. Genet. 65:419-422. A later-published study on the S127R mutation of Abifadel et al., supra, reported that patients carrying such a mutation exhibited higher total cholesterol and apoB100 in the plasma attributed to (1) an overproduction of apoB100-containing lipoproteins, such as low density lipoprotein ("LDL"), very low density lipoprotein ("VLDL") and intermediate density lipoprotein ("IDL"), and (2) an associated reduction in clearance or conversion of said lipoproteins; Ouguerram et al., 2004 Arterioscler. Thromb. Vasc. Biol. 24:1448-1453.

Accordingly, there can be no doubt that PCSK9 plays a role in the regulation of LDL. The expression or upregulation of PCSK9 is associated with increased plasma levels of LDL cholesterol, and the corresponding inhibition or lack of expression of PCSK9 is associated with reduced LDL cholesterol plasma levels. Decreased levels of LDL cholesterol associated with sequence variations in PCSK9 have been found to confer protection against coronary heart disease; Cohen, 2006 *N. Engl. J. Med.* 354:1264-1272.

The identification of compounds and/or agents effective in the treatment of cardiovascular affliction is highly desirable. In clinical trials, reductions in LDL cholesterol levels have been directly related to the rate of coronary events; Law et al., 2003 *BMJ* 326:1423-1427. More recently, the moderate lifelong reduction in plasma LDL cholesterol levels was found to correlate with a substantial reduction in the incidence of coronary events; Cohen et al., supra. This was the case even in populations with a high prevalence of non-lipid-related cardiovascular risk factors; supra. Accordingly, there is great benefit to be reaped from the managed control of LDL cholesterol levels.

The present invention advances these interests by providing antagonists of PCSK9 of use for inhibiting the activities of PCSK9 and the corresponding role PCSK9 plays in various therapeutic conditions.

SUMMARY OF THE INVENTION

The present invention relates to antagonists of PCSK9 and, in particular embodiments, those antagonists that inhibit both human and murine PCSK9 and those exhibiting preferential targeting of processed PCSK9. Broadly, protein-specific antagonists of PCSK9 (or "PCSK9-specific antagonists" as referred to herein) are PCSK9 protein binding molecules or molecules effective in the selective binding of PCSK9 and inhibition of PCSK9 function. These molecules are of import in the treatment of conditions associated with or impacted by PCSK9 function, including, but not limited to hypercholesterolemia, coronary heart disease, metabolic syndrome, acute coronary syndrome and related conditions. PCSK9-specific antagonists are characterized by selective recognition and binding to PCSK9. PCSK9-specific antagonists do not show significant binding to proteins other than PCSK9, other than in those specific instances where the antagonist is supplemented or designed to confer an additional, distinct specificity to the PCSK9-specific binding component.

PCSK9-specific antagonists forming particular embodiments hereof comprise (a) a heavy chain variable region comprising a CDR3 domain comprising SEQ ID NO: 17 or an equivalent of SEQ ID NO: 17, said equivalent characterized as having one or more conservative amino acid substitutions in the CDR3 domain; and/or (b) a light chain variable region comprising a CDR3 domain comprising SEQ ID NO: 7 or an equivalent of SEQ ID NO: 7, said equivalent characterized as having one or more conservative amino acid substitutions in the CDR3 domain. In specific embodiments, PCSK9-specific antagonists bind to human and/or murine PCSK9 with a $K_D$ of $1.2 \times 10^{-6}$ M or less. In more specific embodiments, PCSK9-specific antagonists bind to human and/or murine PCSK9 with a $K_D$ of $1 \times 10^{-7}$ M or less. In additional embodiments, PCSK9-specific antagonists bind to human and/or murine PCSK9 with a $K_D$ of $1 \times 10^{-8}$ M or less. In further embodiments, PCSK9-specific antagonists bind to human and/or murine PCSK9 with a $K_D$ of $5 \times 10^{-9}$ M or less, or of $1 \times 10^{-9}$ M or less. In select embodiments, PCSK9-specific antagonists bind to human and/or murine PCSK9 with a $K_D$ of $1 \times 10^{-10}$ M or less, a $K_D$ of $1 \times 10^{-11}$ M or less, or a $K_D$ of $1 \times 10^{-12}$ M or less. In specific embodiments, PCSK9-specific antagonists do not bind proteins other than PCSK9 at the above levels indicated for binding to PCSK9.

Particular embodiments of the present invention include PCSK9-specific antagonists which exhibit binding to PCSK9 at one of the above prescribed levels and compete for binding to PCSK9 with 1D05 antibody molecules. 1D05 antibody molecules form important PCSK9-specific antagonists hereof. 1D05 antibody molecules are characterized as comprising a (i) heavy chain variable region ("VH") comprising SEQ ID NO: 11; and (ii) a light chain variable region ("VL") comprising SEQ ID NO: 27. Said VH and VL regions comprise the full complement of disclosed CDRs 1, 2 and 3 for the VH (SEQ ID NOs: 13, 15 and 17) and VL regions (SEQ ID NOs: 3, 5 and 7), respectively. Examples of 1D05 antibody molecules include without limitation: (i) a Fab which comprises a light chain comprising SEQ ID NO: 1 and an Fd chain comprising amino acids 1-233 of SEQ ID NO: 9 (or SEQ ID NO: 9); and (ii) a full length antibody molecule which comprises a light chain comprising SEQ ID NO: 26 and a heavy chain comprising SEQ ID NO: 25.

PCSK9-specific antagonists are effective in counteracting PCSK9-dependent inhibition of cellular LDL-uptake, and particularly human and/or murine PCSK9-dependent inhibition of cellular LDL uptake. Repeatedly, PCSK9-specific antagonist 1D05 has demonstrated dose-dependent inhibition of the effects of PCSK9 on LDL uptake. Accordingly, the disclosed PCSK9-specific antagonists are of import for lowering plasma LDL cholesterol levels. The disclosed antagonists also have utility for various diagnostic purposes, including the detection and quantification of PCSK9. Select 1D05 antagonists are, in particular, useful because of their cross-reactivity with both human and murine PCSK9. This quality enables particular 1D05 antagonists to be studied pharmacologically in murine models without having to ensure that the mice express human PCSK9. In such experiments, the murine model is sufficiently representative of the native activity of the targeted protein and the antagonist's inhibition thereof.

In specific embodiments, the present invention encompasses PCSK9-specific antagonists. In particular embodiments, the present invention encompasses antibody molecules comprising disclosed heavy and/or light chain variable regions, equivalents of said regions having one or more conservative amino acid substitutions, and homologs thereof. Select embodiments comprise isolated PCSK9-specific antagonists that comprise the disclosed CDR domains or sets of the heavy and/or light chain CDR domains, and equivalents of such domains characterized as having one or more conservative amino acid substitutions. As will be appreciated by those skilled in the art, fragments of PCSK9-specific antagonists that retain the ability to antagonize PCSK9 may be inserted into various frameworks; see, e.g., U.S. Pat. No. 6,818,418 and references contained therein, the collective disclosures of which are incorporated herein by reference, which discuss various scaffolds which may be used to display antibody loops previously selected on the basis of antigen binding. In the alternative, genes encoding for VL and VH may be joined, using recombinant methods, for example using a synthetic linker that enables them to be made as a single protein chain in which the VL and VH regions pair to form monovalent molecules, otherwise known as single chain Fvs ("ScFVs"); see, e.g., Bird et al., 1988 *Science* 242: 423-426, and Huston et al., 1988 *Proc. Natl. Acad. Sci. USA* 85:5879-5883, the disclosures of which are incorporated herein by reference.

PCSK-9 specific antagonists and fragments may be in the form of various non-antibody-based scaffolds, including but not limited to avimers (Avidia); DARPins (Molecular Partners); Adnectins (Adnexus), Anticalins (Pieris) and Affibodies (Affibody). The use of alternative scaffolds for protein binding is well appreciated in the scientific literature, see, e.g., Binz & Plückthun, 2005 Curr. Opin. Biotech. 16:1-11; the disclosure of which is incorporated herein by reference. Accordingly, non-antibody-based scaffolds or antagonist molecules comprising (i) the disclosed heavy and/or light chain variable region CDR3 sequences (SEQ ID NOs: 17 and 7, respectively), (ii) the disclosed heavy chain variable CDR1, CDR2 and CDR3 sequences or the disclosed light chain variable CDR1, CDR2 and CDR3 sequences: CDR1 (SEQ ID NOs: 13 and 3, respectively), CDR2 (SEQ ID NOs: 15 and 5, respectively) and CDR3 (SEQ ID NOs; 17 and 7, respectively, (iii) the full complement (SEQ ID NOs; 13, 15, 17, 3, 5 and 7) of disclosed heavy and light chain CDRs within a variable region framework of a human heavy and/or light chain sequence, respectively, or (iv) the disclosed heavy and/or light chain variable regions SEQ ID NO: 11 and/or SEQ ID NO: 27 form important embodiments of the present invention, where such scaffolds or antagonist molecules exhibit selectivity for PCSK9 and counteract PCSK9-dependent inhibition of cellular LDL-uptake.

In another aspect, the present invention provides nucleic acid encoding the disclosed PCSK9-specific antagonists and, in particular embodiments, PCSK9-specific antagonists which comprise the disclosed heavy and light chains, the disclosed variable heavy and light regions and select components thereof (including CDRs 1, 2 and/or 3), particularly the disclosed respective CDR3 regions. In another aspect, the present invention provides vectors comprising said nucleic acid. The present invention, additionally, provides isolated cell(s) comprising nucleic acid encoding disclosed PCSK9-specific antagonists. In another aspect, the present invention provides isolated cell(s) comprising a polypeptide or vector of the present invention.

The present invention provides methods for making PCSK9-specific antagonists disclosed herein including but not limited to antibodies, antigen binding fragments, derivatives, chimeric molecules, fusions of any of the foregoing with another polypeptide, or alternative structures/compositions capable of specifically binding PCSK9 which comprise the disclosed sequences. The methods comprise: (i) incubating a cell comprising nucleic acid encoding the PCSK9-specific antagonist(s), or which comprises individual nucleic acids encoding one or more components thereof, said nucleic acids which, when expressed, collectively produce the antagonist(s), under conditions that allow for the expression and/or assembly of the PCSK9-specific antagonist(s), and (ii) isolating said antagonist(s) from the cell. One of skill in the art can obtain PCSK9-specific antagonists disclosed herein using standard recombinant DNA techniques as well.

The present invention provides a method for antagonizing the activity or function of PCSK9 or a noted effect of PCSK9 which comprises contacting a cell, population of cells, or tissue sample of interest expressing PCSK9 (or treated with or having therein human or murine PCSK9) with a PCSK9-specific antagonist disclosed herein under conditions that allow said antagonist to bind to PCSK9. Specific embodiments of the present invention include such methods wherein the cell is a human or murine cell. Additional embodiments are wherein the cell expresses human or murine-derived PCSK9.

In another aspect, the present invention provides a method for antagonizing the activity or function of PCSK9 or a noted effect of PCSK9 in a subject exhibiting a condition associated with PCSK9 activity, or a condition where the functioning of PCSK9 is contraindicated for a particular subject, which comprises administering to the subject a therapeutically effective amount of a PCSK9-specific antagonist of the present invention in a pharmaceutical or other composition.

The present invention, thus, encompasses a method of treating a condition associated with PCSK9 activity, or a condition wherein the functioning of PCSK9 is contraindicated for a particular subject, which comprises administering to the subject a therapeutically effective amount of a PCSK9-specific antagonist of the present invention in a pharmaceutical or other composition. In select embodiments, the condition is hypercholesterolemia, coronary heart disease, metabolic syndrome, acute coronary syndrome or related conditions.

In specific embodiments, the present invention encompasses a method of administering a disclosed PCSK9-specific antagonist to a subject which comprises delivering a therapeutically effective amount of a pharmaceutical or other composition comprising a PCSK9-specific antagonist as disclosed herein.

In another aspect, the present invention provides a pharmaceutical composition or other composition comprising a PCSK9-specific antagonist of the invention characterized as comprising a pharmaceutically acceptable carrier including but not limited to an excipient, diluent, stabilizer, buffer, or alternative designed to facilitate administration of the antagonist in the desired amount to the treated individual.

The following table offers a generalized outline of the sequences discussed in the present application. The Sequence Listing including all notations, sequences and features forms as express part of the disclosure hereof:

TABLE 1

| SEQ ID NO: | DESCRIPTION |
| --- | --- |
| SEQ ID NO: 1 | LIGHT CHAIN ("LC"); 1D05 |
| SEQ ID NO: 2 | LIGHT CHAIN ("LC") NUCLEIC ACID; 1D05 |
| SEQ ID NO: 3 | VL CDR1; 1D05 |
| SEQ ID NO: 4 | VL CDR1 NUCLEIC ACID; 1D05 |
| SEQ ID NO: 5 | VL CDR2; 1D05 |
| SEQ ID NO: 6 | VL CDR2 NUCLEIC ACID; 1D05 |
| SEQ ID NO: 7 | VL CDR3; 1D05 |
| SEQ ID NO: 8 | VL CDR3 NUCLEIC ACID; 1D05 |
| SEQ ID NO: 9 | Fd CHAIN inclusive of linkers and tags; 1D05 |
| SEQ ID NO: 10 | Fd CHAIN NUCLEIC ACID; 1D05 |
| SEQ ID NO: 11 | VH; 1D05 |
| SEQ ID NO: 12 | VH NUCLEIC ACID; 1D05 |
| SEQ ID NO: 13 | VH CDR1; 1D05 |
| SEQ ID NO: 14 | VH CDR1 NUCLEIC ACID; 1D05 |
| SEQ ID NO: 15 | VH CDR2; 1D05 |
| SEQ ID NO: 16 | VH CDR2 NUCLEIC ACID; 1D05 |
| SEQ ID NO: 17 | VH CDR3; 1D05 |
| SEQ ID NO: 18 | VH CDR3 NUCLEIC ACID; 1D05 |
| SEQ ID NO: 19 | FRAGMENT OF PROCESSING SITE |
| SEQ ID NO: 20 | FRAGMENT OF PROCESSING SITE |
| SEQ ID NO: 21 | Constant domain of IgG1 |
| SEQ ID NO: 22 | Constant domain of IgG2 |
| SEQ ID NO: 23 | Constant domain of IgG4 |
| SEQ ID NO: 24 | Constant domain of IgG2m4 |
| SEQ ID NO: 25 | 1D05 IgG2m4 Heavy Chain ("HC") |
| SEQ ID NO: 26 | 1D05 IgG Light (Kappa) Chain |
| SEQ ID NO: 27 | VL; 1D05 |
| SEQ ID NO: 28 | VL NUCLEIC ACID; 1D05 |
| SEQ ID NO: 29 | 1D05 IgG2m4 HC NUCLEIC ACID |
| SEQ ID NO: 30 | 1D05 IgG LC NUCLEIC ACID |
| SEQ ID NO: 31 | 1D05 IgG2m4 HC PLASMID |
| SEQ ID NO: 32 | 1D05 IgG LC PLASMID |
| SEQ ID NO: 33 | PRIMER |
| SEQ ID NO: 34 | PRIMER |
| SEQ ID NO: 35 | PRIMER |
| SEQ ID NO: 36 | PRIMER |
| SEQ ID NO: 37 | 1D05 EPITOPE DOMAIN |
| SEQ ID NO: 38 | PORTION OF PCSK9 SEQUENCE IN FIGURE |
| SEQ ID NO: 39 | HUMAN EPITOPE AREA |
| SEQ ID NO: 40 | CONSENSUS SEQUENCE |

TABLE 1-continued

| SEQ ID NO: | DESCRIPTION |
|---|---|
| SEQ ID NO: 41 | MURINE EPITOPE AREA |
| SEQ ID NO: 42 | SECONDARY FOOTPRINT EPITOPE |
| SEQ ID NO: 43 | 1D05 Variant VH CDR1 Sequence |
| SEQ ID NO: 44 | 1D05 Variant VH CDR2 Sequence |
| SEQ ID NO: 45 | 1D05 Variant VH CDR3 Sequence |
| SEQ ID NO: 46 | 1D05 Variant VL CDR1 Sequence |
| SEQ ID NO: 47 | 1D05 Variant VL CDR2 Sequence |
| SEQ ID NO: 48 | 1D05 Variant VL CDR3 Sequence |
| SEQ ID NO: 49 | VL; 1D05 Variant Sequence |
| SEQ ID NO: 50 | VH; 1D05 Variant Sequence |
| SEQ ID NO: 51 | VH; 1D05 Variant Sequence H32Y |
| SEQ ID NO: 52 | VH; 1D05 Variant Sequence M48A |
| SEQ ID NO: 53 | VH; 1D05 Variant Sequence M48L |
| SEQ ID NO: 54 | VH; 1D05 Variant SequenceH99Y |
| SEQ ID NO: 55 | VH; 1D05 Variant Sequence M48L/M109L/M115L |
| SEQ ID NO: 56 | VH; 1D05 Variant SequenceM48V |
| SEQ ID NO: 57 | V1; 1D05 Variant Sequence N50D |
| SEQ ID NO: 58 | V1; 1D05 Variant Sequence N50Q |
| SEQ ID NO: 59 | V1; 1D05 Variant SequenceN50T |
| SEQ ID NO: 60 | V1; 1D05 Variant SequenceN50Y |

BRIEF DESCRIPTION OF THE DRAWINGS

FIGS. 3A-3D have two controls: (i) a cell only control, showing the basal level of cellular LDL uptake, and (ii) a cell+PCSK9 (5 µg/ml) control which shows the level of PCSK9-dependent loss of LDL-uptake. The titration experiments which contain 1D05 and PCSK9 were done at a fixed concentration of PCSK9 (5 µg/ml) and increasing concentrations of 1D05 shown in the graphs. As shown, 1D05 can inhibit the effect of PCSK9 on cellular LDL uptake. $IC_{50}$s for 1D05 (Fab) are 97 and 144 nM for mouse and human PCSK9 protein, respectively. $IC_{50}$s for 1D05 (IgG) are 85 and 79 nM for mouse and human PCSK9 protein, respectively.

FIGS. 4A and 4B illustrate inhibition of PCSK9 internalization by 1D05 (Fab and IgG, respectively) and restoration of LDL uptake. HepG2 cells were plated and AlexaFluor-labeled PCSK9 and LDL were then added to cells and incubated at 37° C. for 4 hrs. Following incubation, the amount of PCSK9 or LDL internalized by cells was determined using cofocal microscopy. Controls included the addition of cells alone (No treatment), and only AF-labeled PCSK9 in addition to 50× (250 µg/ml) unlabeled PCSK9 (50× Cold Wt). In addition to 5 µg/ml wild-type AF-labeled PCSK9 and 10 µg/ml AF-labeled LDL, increasing amounts of either the 1D05 Fab (panel A) or IGG (panel B) were added, resulting in subsequent inhibition of PCSK9 internalization into cells and a recovery of LDL uptake. Together, these studies demonstrate that both the Fab and IgG prevent PCSK9 internalization into cells.

FIG. 6 illustrates a sequence comparison of the constant domains of IgG1 (SEQ ID NO: 21; Fc domain of which is represented by residues 110-130 of SEQ ID NO: 21), IgG2 (SEQ ID NO: 22, Fc domain of which is represented by residues 107-326 of SEQ ID NO: 22), IgG4 (SEQ ID NO: 23; Fc domain of which is represented by residues 107-327 of SEQ ID NO: 23) and IgG2 m4 (SEQ ID NO: 24; Fc domain of which is represented by residues 107-326 of SEQ ID NO: 24) isotypes.

FIGS. 7A and 7B illustrate peptide fragments originated by limited proteolysis of a) wt-PCSK9 and b) 1D05/wt-PCSK9 complex with AspN for 5 minutes. The star in FIG. 7A highlights the peptide fragment present in the wt-PCSK9 spectrum which is not detected in the 1D05/wt-PCSK9 spectrum. The aspartic acid residue 169 is hence protected in the complex.

FIGS. 9C-D illustrate the zoom views of the same spectra, respectively. The stars in FIGS. 9A and 9C highlight the peptide fragments present in the wt-PCSK9 spectrum which are not detected in the 1D05/wt-PCSK9 spectrum.

FIG. 10 illustrates residues of the primary sequence of the wt-PCSK9 catalytic domain involved in binding with 1D05 neutralizing Fab. The peptide fragments of wt-PCSK9 protected in limited proteolysis experiments by 1D05 binding are boxed.

FIGS. 12A and 12B illustrate sequence alignment between the identified general epitope areas of human (SEQ ID NO: 39) and murine (SEQ ID NO: 41) PCSK9. A consensus sequence (SEQ ID NO: 40) is provided as the second sequence of FIG. 12A. As evident in the Figures, the residues included in the protected peptide 194-199 are conserved among the two species while the residues in peptide 165-169 are not.

FIGS. 14A-D illustrates that 1B20 is a full inhibitor of PCSK9 function in the Exopolar assay.

DETAILED DESCRIPTION OF THE INVENTION

Figure 1:
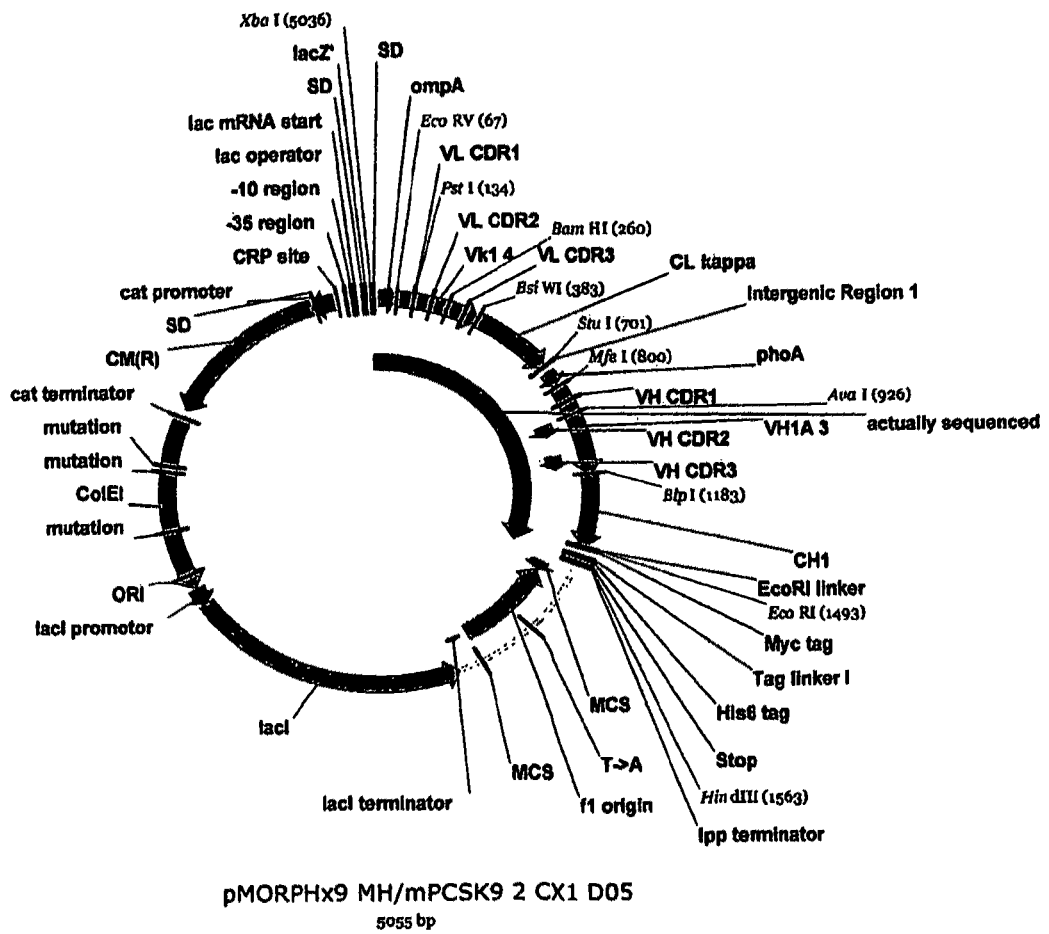
FIG. 1 illustrates Fab expression vector pMORPH_x9_MH encoding the mPCSK9 2CX1D05 Fab heavy and light chains.

The present invention relates to antagonists of PCSK9 and, in particular embodiments, those antagonists that inhibit both human and murine PCSK9 and those that preferentially target processed PCSK9. Protein-specific antagonists of PCSK9 (or "PCSK9-specific antagonists") in accordance herewith are effective in the selective binding to and inhibition of PCSK9 function and, thus, are of import in the treatment of conditions associated with or impacted by PCSK9 function, including, but not limited to, hypercholesterolemia, coronary heart disease, metabolic syndrome, acute coronary syndrome and related conditions. Use of the term "antagonist" refers to the fact that the subject molecule can antagonize the functioning of PCSK9. Use of the term "antagonizing" or derivatives thereof refers to the act of opposing, counteracting, inhibiting, neutralizing or curtailing one or more functions of PCSK9. Reference herein to PCSK9 function or PCSK9 activity refers to any function or activity that is driven by, requires, or is exacerbated or enhanced by PCSK9. PCSK9-specific antagonists as described herein have proven to be effective for counteracting human and/or murine PCSK9-dependent inhibition of cellular LDL-uptake.

One important embodiment hereof relates to 1D05 antibody molecules. Such 1D05 antibody molecules are characterized as comprising a (i) heavy chain variable region ("VH") comprising SEQ ID NO: 11; and (ii) a light chain variable region ("VL") comprising SEQ ID NO: 27. Said VH and VL regions comprise the full complement of disclosed CDRs 1, 2 and 3 for the VH (SEQ ID NOs: 13, 15 and 17) and VL regions (SEQ ID NOs: 3, 5 and 7), respectively. Examples of 1D05 antibody molecules include without limitation: (i) a Fab which comprises a light chain comprising SEQ ID NO: 1 and an Fd chain comprising amino acids 1-233 of SEQ ID NO: 9 (or SEQ ID NO: 9); and (ii) a full length antibody molecule which comprises a light chain comprising SEQ ID NO: 26 and a heavy chain comprising SEQ ID NO: 25. The select group of 1D05 antibodies demonstrate that PCSK9-specific antagonists as disclosed herein effectively inhibit both human and murine PCSK9 and may be studied pharmacologically in murine models absent the expression of human PCSK9.

The CDR definitions arrived at and disclosed herein were defined using the Morphosys software program Sequence Analysis Software ("SAS"). Applicants wish to note, however, that various other methods are available to delineate and define the start and end points of the CDR sequences, including but not limited to Kabat, 1991 *Sequences of Proteins of Immunological Interest*, 5<sup>th</sup> edit., NIH Publication no. 91-3242 U.S. Department of Health and Human Services; Clothia et al., 1987 *J. Mol. Biol.* 196:901-917; Clothia et al., 1989 *Nature* 342:877-883; Lefranc, 1997 *Immunol. Today*, 18:509; and Chen et al., 1999 *J. Mol. Biol.* 293:865-881. These and other methods have been reviewed and are well within the realm of skills possessed by those in the art; see, e.g., Honegger & Plückthun, 2001 *J. Mol. Biol.* 309:657-670. While the current inventors have employed the SAS software to define the CDRs, the present invention fully encompasses the different definitions around the sequences and the varying CDR delineations arrived at through use of any different analysis software or methods. Said use and resulting CDR definitions based on the presently disclosed sequences is fully within the scope of the present disclosure and anticipated herein.

PCSK9-specific molecules also have utility for various diagnostic purposes in the detection and quantification of PCSK9.

Disclosed PCSK9-specific antagonists are, furthermore, unique in that select embodiments have demonstrated a preferential recognition of processed PCSK9, the active form of PCSK9.

PCSK9-specific antagonists as disclosed herein are desirable molecules for lowering plasma LDL cholesterol levels and are of utility for any primate, mammal or vertebrate of commercial or domestic veterinary importance. PCSK9-specific antagonists are of utility as well to inhibit the activity of PCSK9 in any population of cells or tissues possessing the LDL receptor. The utility of the disclosed antagonists is directly measurable by assays readily available to the skilled artisan. Means for measuring LDL uptake are described in the literature; see, e.g., Barak & Webb, 1981 *J. Cell Biol.* 90:595-604, and Stephan & Yurachek, 1993 *J. Lipid Res.* 34:325330. In addition, means for measuring LDL cholesterol in plasma is well described in the literature; see, e.g., McNamara et al., 2006 *Clinica Chimica Acta* 369:158-167. The particular impact of the disclosed antagonists on cellular LDL uptake may also be measured through a method which comprises providing purified PCSK9 and labeled LDL particles to a cell sample; providing a PCSK9 antagonist to the cell sample; incubating said cell sample for a period of time sufficient to allow LDL particle uptake by the cells; quantifying the amount of label incorporated into the cell; and identifying those antagonists that result in an increase in the amount of quantified label taken up by the cells as compared with that observed when PCSK9 is administered alone. An additional method for measuring the impact of the disclosed antagonists comprises providing purified PCSK9 and labeled LDL particles to a cell sample; providing a PCSK9 antagonist to the cell sample; incubating said cell sample for a period of time sufficient to allow LDL particle uptake by the cells; isolating cells of the cell sample by removing the supernate; reducing non-specific association of labeled LDL particles (whether to the plate, the cells, or anything other than the LDL receptor); lysing the cells; quantifying the amount of label retained within the cell lysate; and identifying those antagonists that result in an increase in the amount of quantified label taken up by the cells as compared with that observed when PCSK9 is administered alone. Antagonists that result in an increase in the amount of quantified label are PCSK9 antagonists.

Any type of cell bearing the LDL receptor can be employed in the above methods including, but not limited to HEK cells, HepG2 cells, and CHO cells. LDL particles derived from any source are of use in the above-described assays. In particular assays, the LDL particles are fresh particles derived from blood. This can be accomplished by any method available to the skilled artisan including, but not limited to, the method of Havel et al., 1955 *J. Clin. Invest.* 34: 1345-1353. The LDL particles may be labeled with fluorescence. The labeled LDL particles may have incorporated therein visible wavelength excited fluorophore 3,3'-dioctadecylindocarbocyanine iodide (dil(3)) to form the highly fluorescent LDL derivative dil(3)-LDL. Any label which enables the skilled artisan to detect LDL in the cellular lysate may be used. An LDL analog may be used that would only become detectable (e.g., become fluorescent or fluoresce at a different wavelength, etc.) when metabolized intracellularly or, for instance, if it were to become associated with (or dissociated from) other molecules in the process of becoming internalized (e.g. a FRET assay, in which an LDL analog would become associated with a secondary fluor, or else be dissociated from a quencher). Any means available in the art for detecting internalization of labeled LDL particles can be employed. The incubation time for the LDL particles and PCSK9 with the cells is an amount of time sufficient to allow LDL particle uptake by the cells. This time may be within the range of 5 minutes to 360 minutes. The concentration of PCSK9 added to the cells may be in the range of 1 nM to 5 µM and, in specific methods, be in the range of 0.1 nM to 3 µM. One specific means by which the skilled artisan can determine a range of concentrations for a particular PCSK9 protein is to develop a dose response curve in the LDL-uptake assay. A concentration of PCSK9 can be selected that promotes close to maximal loss of LDL-uptake and is still in the linear range of the dose response curve. Typically, this concentration is ~5 times the EC-50 of the protein extracted from the dose response curve. The concentrations can vary by protein.

Broadly, PCSK9-specific antagonists as defined herein selectively recognize and specifically bind to PCSK9. An antibody is typically said to specifically bind an antigen when the dissociation constant is ≤1 µM, preferably ≤100 nM and most preferably ≤10 nM. Use of the terms "selective" or "specific" herein, further, refers to the fact that the disclosed antagonists do not show significant binding to proteins other than PSCK9, except in those specific instances where the antagonist is supplemented or designed to confer an additional, distinct specificity to the PCSK9-specific binding portion (as, for example, in bispecific or bifunctional molecules where the molecule is designed to bind two molecules or effect two functions, at least one of which is to specifically bind PCSK9). In specific embodiments, PCSK9-specific antagonists bind to human and/or murine PCSK9 with a $K_D$ of $1.2 \times 10^{-6}$ M or less. In more specific embodiments, PCSK9-specific antagonists bind to human and/or murine PCSK9 with a $K_D$ of $5 \times 10^{-7}$ M or less, of $2 \times 10^{-7}$ M or less, or of $1 \times 10^{-7}$ M or less. In additional embodiments, PCSK9-specific antagonists bind to human and/or murine PCSK9 with a $K_D$ of $1 \times 10^{-8}$ M or less. In further embodiments, PCSK9-specific antagonists bind to human and/or murine PCSK9 with a $K_D$ of $5 \times 10^{-9}$ M or less, or of $1 \times 10^{-9}$ M or less. In select embodiments, PCSK9-specific antagonists bind to human and/or murine PCSK9 with a $K_D$ of $1 \times 10^{-10}$ M or less, a $K_D$ of $1 \times 10^{-11}$ M or less, or a $K_D$ of $1 \times 10^{-12}$ M or less. In specific embodiments, PCSK9-specific antagonists do not bind proteins other than PCSK9 at the above $K_D$s. $K_D$ refers to the dissociation constant obtained from the ratio of $K_d$ (the dissociation rate of a particular binding molecule-target protein interaction) to $K_a$ (the association rate of the particular binding molecule-target protein interaction), or $K_d/K_a$ which is expressed as a molar concentration (M). $K_D$ values can be determined using methods well established in the art. A preferred method for determining the $K_D$ of a binding molecule is by using surface plasmon resonance, for example employing a biosensor system such as a Biacore™ (GE Healthcare Life Sciences) system.

PCSK9-specific antagonists disclosed herein have been shown to dose-dependently inhibit human and/or murine PCSK9 dependent effects on LDL uptake. Accordingly, PCSK9-specific antagonists as disclosed herein are characterized by their ability to counteract PCSK9-dependent inhibition of LDL uptake into cells. This uptake of LDL into cells by the LDL receptor is referred to herein as "cellular LDL uptake". In specific embodiments, PCSK9-specific antagonists counteract or antagonize human and/or murine PCSK9-dependent inhibition of LDL uptake into cells, exhibiting an $IC_{50}$ of less than $1.0 \times 10^{-6}$ M, or, in order of preference, less than $1 \times 10^{-7}$ M, $1 \times 10^{-8}$ M, $1 \times 10^{-9}$ M, $1 \times 10^{-10}$ M, $1 \times 10^{-11}$ M and $1 \times 10^{-12}$ M. The extent of inhibition by any PCSK9-specific antagonist may be measured quantitatively in statistical comparison to a control, or via any alternative method available in the art for assessing a negative effect on, or inhibition of, PCSK9 function (i.e., any method capable of assessing antagonism of PCSK9 function). In specific embodiments, the inhibition is at least about 10% inhibition. In other embodiments, the inhibition is at least 20%, 30%, 40%, 50%, 60%, 70,%, 80%, 90%, or 95%. Accordingly, PCSK9-specific antagonists capable of effecting these levels of inhibition of PCSK9 function form particular embodiments hereof.

A PCSK9-specific antagonist in accordance herewith can be any binding molecule that specifically binds human and/or murine PCSK9 protein including, but not limited to, antibody molecules as defined below, any PCSK9-specific binding structure, any polypeptide or nucleic acid structure that specifically binds PCSK9, and any of the foregoing incorporated into various protein scaffolds; including but not limited to, various non-antibody-based scaffolds, and various structures capable of affording or allowing for selective binding to PCSK9 including but not limited to small modular immunopharmaceuticals (or "SMIPs"; see, Haan & Maggos, 2004 *Biocentury* January 26); Immunity proteins (see, e.g., Chak et al., 1996 *Proc. Natl. Acad. Sci. USA* 93:6437-6442); cytochrome b562 (see Ku and Schultz, 1995 *Proc. Natl. Acad. Sci. USA* 92:6552-6556); the peptide α2p8 (see Barthe et al., 2000 *Protein Sci.* 9:942-955); avimers (Avidia; see Silverman et al., 2005 *Nat. Biotechnol.* 23:1556-1561); DARPins (Molecular Partners; see Binz et al., 2003 *J. Mol. Biol.* 332:489-503; and Forrer et al., 2003 *FEBS Lett.* 539:2-6); Tetranectins (see, Kastrup et al., 1998 *Acta. Crystallogr. D. Biol. Crystallogr.* 54:757-766); Adnectins (Adnexus; see, Xu et al., 2002 *Chem. Biol.* 9:933-942), Anticalins (Pieris; see Vogt & Skerra, 2004 *Chemobiochem.* 5:191-199; Beste et al., 1999 *Proc. Natl. Acad. Sci. USA* 96:1898-1903; Lamla & Erdmann, 2003 *J. Mol. Biol.* 329:381-388; and Lamla & Erdmann, 2004 *Protein Expr. Purif.* 33:39-47); A-domain proteins (see North & Blacklow, 1999 *Biochemistry* 38:3926-3935), Lipocalins (see Schlehuber & Skerra, 2005 *Drug Discov. Today* 10:23-33); Repeat-motif proteins such as Ankyrin repeat proteins (see Sedgwick & Smerdon, 1999 *Trends Biochem. Sci.* 24:311-316; Mosavi et al., 2002 *Proc. Natl. Acad. Sci. USA* 99:16029-16034; and Binz et al., 2004 *Nat. Biotechnol.* 22:575-582); Insect Defensin A (see Zhao et al., 2004 *Peptides* 25:629-635); Kunitz domains (see Roberts et al., 1992 *Proc. Natl. Acad. Sci. USA* 89:2429-2433; Roberts et al., 1992 *Gene* 121:9-15; Dennis & Lazarus, 1994 *J. Biol. Chem.* 269:22129-22136; and Dennis & Lazarus, 1994 *J. Biol. Chem.* 269:22137-22144); PDZ-Domains (see Schneider et al., 1999 *Nat. Biotechnol.* 17:170-175); Scorpion toxins such as Charybdotoxin (see Vita et al., 1998 *Biopolymers* 47:93-100); $10^{th}$ fibronectin type III domain (or 10Fn3; see Koide et al., 1998 *J. Mol. Biol.* 284:1141-1151, and Xu et al., 2002 *Chem. Biol.* 9:933-942); CTLA-4 (extracellular domain; see Nuttall et al., 1999 *Proteins* 36:217-227; and Irving et al., 2001 *J. Immunol. Methods* 248:31-45); Knottins (see Souriau et al., 2005 *Biochemistry* 44:7143-7155 and Lehtio et al., 2000 *Proteins* 41:316-322); Neocarzinostatin (see Heyd et al. 2003 *Biochemistry* 42:5674-5683); carbohydrate binding module 4-2 (CBM4-2; see Cicortas et al., 2004 *Protein Eng. Des. Sel.* 17:213-221); Tendamistat (see McConnell & Hoess, 1995 *J. Mol. Biol.* 250:460-470, and Li et al., 2003 *Protein Eng.* 16:65-72); T cell receptor (see Holler et al., 2000 *Proc. Natl. Acad. Sci. USA* 97:5387-5392; Shusta et al., 2000 *Nat. Biotechnol.* 18:754-759; and Li et al., 2005 *Nat. Biotechnol.* 23:349-354); Affibodies (Affibody; see Nord et al., 1995 *Protein Eng.* 8:601-608; Nord et al., 1997 *Nat. Biotechnol.* 15:772-777; Gunneriusson et al., 1999 *Protein Eng.* 12:873-878); and other selective binding proteins or scaffolds recognized in the literature; see, e.g., Binz & Plückthun, 2005 *Curr. Opin. Biotech.* 16:1-11; Gill & Damle, 2006 *Curr. Opin. Biotechnol.* 17:1-6; Hosse et al., 2006 *Protein Science* 15:14-27; Binz et al., 2005 *Nat. Biotechnol.* 23:1257-1268; Hey et al., 2005 *Trends in Biotechnol.* 23:514-522; Binz & Plückthun, 2005 *Curr. Opin. Biotech.* 16:459-469; Nygren & Skerra, 2004 *J. Immunolog. Methods* 290:3-28; Nygren & Uhlen, 1997 *Curr. Opin. Struct. Biol.* 7:463-469; the disclosures of which are incorporated herein by reference. Antibodies and the use of antigen-binding fragments is well defined and understood in the literature. The use of alternative scaffolds for protein binding is well appreciated in the scientific literature as well, see, e.g., Binz & Plückthun, 2005 *Curr. Opin. Biotech.* 16:1-11; Gill & Damle, 2006 *Curr. Opin. Biotechnol.* 17:1-6; Hosse et al., 2006 *Protein Science* 15:14-27; Binz et al., 2005 *Nat. Biotechnol.* 23:1257-1268; Hey et al., 2005 *Trends in Biotechnol.* 23:514-522; Binz & Plückthun, 2005 *Curr. Opin. Biotech.* 16:459-469; Nygren & Skerra, 2004 *J. Immunolog. Methods* 290:3-28; Nygren & Uhlen, 1997 *Curr. Opin. Struct. Biol.* 7:463-469; the disclosures of which are incorporated herein by reference. Accordingly, non-antibody-based scaffolds or antagonist molecules in accordance herewith exhibiting selectivity for PCSK9 that counteract PCSK9-dependent inhibition of cellular LDL-uptake form important embodiments of the present invention. Aptamers (nucleic acid or peptide molecules capable of selectively binding a target molecule) are one specific example. They can be selected from random sequence pools or identified from natural sources such as riboswitches. Peptide aptamers, nucleic acid aptamers (e.g., structured nucleic acid, including both DNA and RNA-based structures) and nucleic acid decoys can be effective for selectively binding and inhibiting proteins of interest; see, e.g., Hoppe-Seyler & Butz, 2000 *J. Mol. Med.* 78:426-430; Bock et al., 1992 *Nature* 355:564-566; Bunka & Stockley, 2006 *Nat. Rev. Microbiol.* 4:588-596; Martell et al., 2002 *Molec. Ther.* 6:30-34; Jayasena, 1999 *Clin. Chem.* 45:1628-1650; the disclosures of which are incorporated herein by reference.

Importantly, the binding site (or epitope) for 1D05 on PCSK9 was identified through limited proteolysis and mass spectrometry ("LP-MS"). The limited proteolysis mass spectrometry analysis involved incubating wild-type PCSK9 ("wt-PCSK9") and a complex of wt-PCSK9 and 1D05 with endoproteinase enzymes of different specificity in carefully controlled conditions. Under such conditions, the endoproteases cleaved only exposed primary cleavage sites. The experiment was designed so that the binding of 1D05 to wt-hPCSK9 masked surface residues normally exposed on wt-hPCSK9 not bound to the antibody. Such masked residues provided insight into the binding domain of 1D05. Through such experiments, a novel neutralizing epitope conformational in nature and represented by peptides RYRAD (SEQ ID NO: 42) AND REIEGR (SEQ ID NO: 37) was identified. This epitope falls within PCSK9's catalytic domain and provides a novel target epitope for which to identify additional effective PCSK9 antagonists. Identification of additional PCSK9-specific antagonists binding this epitope is of significant interest given 1D05's PCSK9-neutralizing activity.

One means of identifying antagonists and particularly antibodies that bind to the identified 1D05 epitope or an overlapping epitope is through a competition or similar assay where the candidate antibody or binding molecule would have to out-compete 1D05 for the epitope. Competitive antagonists encompassed herein are molecules that inhibit (i.e., prevent or interfere with in comparison to a control) or reduce 1D05 binding by at least 50%, 60%, 70%, and 80% in order of increasing preference (even more preferably, at least 90% and, most preferably, at least 95%) at 1 μM or less with 1D05 at or below its $K_D$, and in particular those molecules that antagonize (i) PCSK9 binding to the LDL receptor, (ii) PCSK9 internalization into cells, or (iii) both PCSK9 binding to the LDL receptor and PCSK9 internalization into cells. Competition between binding members may be readily assayed in vitro for example using ELISA and/or by monitoring the interaction of the antibodies with PCSK9 in solution. The exact means for conducting the analysis is not critical. PCSK9 may be immobilized to a 96-well plate or may be placed in a homogenous solution. In specific embodiments, the ability of unlabeled candidate antibody(ies) to block the binding of labeled 1D05 can be measured using radioactive, enzyme or other labels. In the reverse assay, the ability of unlabeled antibodies to interfere with the interaction of labeled 1D05 with PCSK9 wherein said 1D05 and PCSK9 are already bound is determined. In specific embodiments, (i) PCSK9 is contacted with labeled 1D05 (an antibody molecule which comprises a VL comprising SEQ ID NO: 27 and a VH comprising SEQ ID NO: 11); (ii) PCSK9 is contacted with the candidate antibody or pool of antibodies; and (iii) antibodies capable of interrupting or preventing complexes between PCSK9 and 1D05 are identified. The readout in such an example is through measurement of bound label. 1D05 and the candidate antibody(ies) may be added in any order or at the same time. A specific assay that may be run is that of Example 13 where the activity of an antibody found to bind to the same epitope domain as 1D05 is illustrated.

Antibodies identified as 1D05 competitors in the above or other suitable assays may be tested for the ability to antagonize or neutralize (i) PCSK9 binding to the LDL receptor; and/or (ii) PCSK9 internalization into cells. These parameters may be measured through the use of assays similar to that employed or described in the current specification. In specific embodiments, the inhibition demonstrated by the competing antibody is at least about 10% inhibition. In other embodiments, the inhibition is at least 20%, 30%, 40%, 50%, 60%, 70%, 80%, 90% or 95%.

The present invention specifically encompasses PCSK9-specific antagonists and particularly monoclonal antibody molecules (and their corresponding amino acid and nucleic acid sequences) that selectively bind to the epitope identified for 1D05 or an overlapping epitope interfering with 1D05's binding to PCSK9. Critical residues for 1D05 binding that were identified on the epitope of PCSK9 are those residues corresponding to residues Arg194, Glu197 and Arg199 of human PCSK9. The narrow epitope comprising these amino acid residues is represented by SEQ ID NO: 37 and falls within the area of SEQ ID NO: 39 of human PCSK9 and SEQ ID NO: 41 of murine PCSK9. A secondary footprint of the antibody is represented by SEQ ID NO: 42. Monoclonal antibodies that specifically bind to the conformational epitope represented by SEQ ID NO: 37 and SEQ ID NO:42 or an overlapping epitope antagonize or neutralize (i) PCSK9 binding to the LDL receptor; (ii) PCSK9 internalization into cells, or (iii) both. Accordingly, monoclonal antibodies that bind to an epitope on PCSK9 which comprises and/or consists of: SEQ ID NO: 37, SEQ ID NO: 39 or SEQ ID NO: 41 form important embodiments of the present invention. Specific embodiments of the present invention relate to monoclonal antibodies that recognize the following epitopes on PCSK9: SEQ ID NO: 37 and SEQ ID NO: 42. A monoclonal antibody molecule in accordance herewith may be an intact (complete or full length) antibody, a substantially intact antibody, or a portion or fragment of an antibody comprising an antigen-binding portion, e.g., a Fab fragment, Fab' fragment or F(ab')$_2$ fragment of a murine antibody or of a chimeric antibody or of a humanized antibody or of a human antibody. Monoclonal, as used herein, refers to a homogeneous or substantially homogeneous (or pure) antibody population (i.e., at least about 90%, 91%, 92%, 93%, 94%, 95%, 96%, more preferably at least about 97% or 98%, or most preferably at least 99% of the antibodies in the population are identical and would compete in an ELISA assay for the same antigen or epitope. In specific embodiments of the present invention, the present invention provides monoclonal antibodies that (i) compete for binding to PCSK9 with a 1D05 antibody molecule, reducing 1D05 binding by at least 50% at 1 µM or less with 1D05 at or below its $K_D$, (ii) block PCSK9 binding to the LDL receptor, (iii) inhibit PCSK9 internalization into the cell, and (iv) comprise a specific antigen-binding region, VH, VL, set of CDRs or heavy CDR3, heavy and/or light chain or any variant of these components described herein. Additional embodiments provide PCSK9-specific antagonists including but not limited to monoclonal antibodies that recognize/bind to SEQ ID NO: 37, SEQ ID NO: 39 or SEQ ID NO: 41, wherein the PCSK9-specific antagonists bind to human and/or murine PCSK9 with a $K_D$ of $1.2 \times 10^{-6}$ M or less, and wherein the PCSK9-specific antagonist competes with 1D05 for binding to PCSK9. In specific embodiments hereof, the PCSK9-specific antagonists are further defined by one or more of the following qualities: they (i) reduce 1D05 binding by at least 50% at 1 µM or less with 1D05 at or below its $K_D$, (ii) block PCSK9 binding to the LDL receptor, (iii) inhibit PCSK9 internalization into the cell, and/or (iv) comprise a specific antigen-binding region, VH, VL, set of CDRs or heavy CDR3, heavy and/or light chain or any variant of these components described herein. In specific embodiments, the PCSK9-specific antagonists in accordance with the above comprise (i) the disclosed heavy and/or light chain variable region CDR3 sequences (SEQ ID NOs: 17 and 7, respectively), (ii) the disclosed heavy and/or light chain variable regions CDR1 (SEQ ID NOs: 13 and 3, respectively), CDR2 (SEQ ID NOs: 15 and 5, respectively) and CDR3 (SEQ ID NOs; 17 and 7, respectively, (iii) the full complement (SEQ ID NOs; 13, 15, 17, 3, 5 and 7) of disclosed heavy and light chain CDRs within a variable region framework of a human heavy and/or light chain sequence; (iv) the disclosed VL and/or VH regions (SEQ ID NOs: 27 and 11, respectively); (v) the disclosed light and/or Fd chains (SEQ ID NO: 1 and amino acids 1-233 of SEQ ID NO: 9 (or SEQ ID NO: 9)), or (vi) the disclosed light and/or heavy chains (SEQ ID NOs: 26 and 25). In specific embodiments, the PCSK9-specific antagonists bind to/recognize both SEQ ID NOs: 37 and SEQ ID NO: 42.

In any of the above assays for identifying antibodies binding the same or overlapping epitope region as 1D05, binding of the known binder (i.e., 1D05 antibody molecule known to bind residues Arg194, Glu197 and Arg199 of SEQ ID NO: 37) as compared to the binding of the candidate binder should be distinguishable. This can (but need not) be accomplished through the use of labels on either or both molecules as will be readily appreciated by the skilled artisan. Labels, as used herein, refer to another molecule or agent incorporated into/affixed to the antibody molecule. In one embodiment, the label is a detectable marker, e.g., a radiolabeled amino acid or attachment to a polypeptide of biotinyl moieties that can be detected by marked avidin (e.g., streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

A 1D05 antibody used for the competition assays may be any antibody molecule which is of the 1D05 description provided herein (i.e. any antibody molecule selective for PCSK9 which comprises a VL comprising SEQ ID NO: 27 and a VH comprising SEQ ID NO: 11). Examples of such antibodies include without limitation (i) a Fab which comprises a light chain comprising SEQ ID NO: 1 and an Fd chain comprising amino acids 1-233 of SEQ ID NO: 9 (or SEQ ID NO: 9); (ii) a full length antibody molecule which comprises a light chain comprising SEQ ID NO: 26 and a heavy chain comprising SEQ ID NO: 25.

Peptides or peptidomimetics based on the regions corresponding to SEQ ID NO: 39 or SEQ ID NO: 41 (and in select embodiments the areas corresponding to SEQ ID NO: 37 and SEQ ID NO: 42) should have antagonistic properties by preventing the interaction of PCSK9 with LDLR. Importantly, peptides that comprise SEQ ID NO: 37 and SEQ ID NO: 42 should generate neutralizing antibodies able to inhibit PCSK9 binding to LDLR and/or inhibit PCSK9 internalization into cells.

In specific embodiments, peptides encompassed herein comprise SEQ ID NO: 39 OR SEQ ID NO: 41. In select embodiments, the peptides comprise SEQ ID NO: 37 and are less than 50 amino acids. In certain embodiments, the peptides comprise both SEQ ID NO: 37 and SEQ ID NO: 42 and are 40 amino acids or less. In more specific embodiments, the peptides comprise SEQ ID NO: 37 and are less than 40 amino acids, less than 30 amino acids, less than 20 amino acids, or less than 10 amino acids.

Screening of peptides of the invention may be carried out utilizing competition assays as described above. If the peptide being tested competes with a 1D05 antibody molecule (i.e. any antibody molecule selective for PCSK9 which comprises a VL comprising SEQ ID NO: 27 and a VH comprising SEQ ID NO: 11) as shown by a decrease in binding of such 1D05 antibody molecule then it is likely that the peptide and 1D05 bind to the same, or a closely related, epitope. Still another way to determine whether a peptide has the specificity of the 1D05 antibody molecule is to pre-incubate the 1D05 antibody molecule with PCSK9 with which it is normally reactive, and then add the peptide being tested with demonstrated specificity for PCSK9 to determine whether the peptide is inhibited in its ability to bind PCSK9. If the peptide being tested is inhibited then, in all likelihood, it has the same, or a functionally equivalent, epitope and specificity as the 1D05 antibody molecule.

Using routine procedures as outlined throughout the instant specification and well known to those of ordinary skill in the art, one can then determine whether a peptide which binds to PCSK9 is useful by determining whether the peptide is blocks PCSK9 from binding to the LDL receptor and/or prevents PCSK9 internalization into cells.

Expression and selection of any of the PCSK9-specific antagonists described in the present application may be achieved using suitable technologies including, but not limited to phage display (see, e.g., International Application Number WO 92/01047, Kay et al., 1996 *Phage Display of Peptides and Proteins: A Laboratory Manual*, San Diego: Academic Press), yeast display, bacterial display, T7 display, and ribosome display (see, e.g., Lowe & Jermutus, 2004 *Curr. Pharm. Biotech.* 517-527).

Particular PCSK9-specific antagonists forming part of the present invention are antibody molecules or antibodies. "Antibody molecule" or "Antibody" as described herein refers to an immunoglobulin-derived structure with selective binding to human and/or murine PCSK9 including, but not limited to, a full length or whole antibody, an antigen binding fragment (a fragment derived, physically or conceptually, from an antibody structure), a derivative of any of the foregoing, a fusion of any of the foregoing with another polypeptide, or any alternative structure/composition which incorporates any of the foregoing for purposes of selectively binding to/inhibiting the function of PCSK9.

"Whole" antibodies or "full length" antibodies refer to proteins that comprise two heavy (H) and two light (L) chains inter-connected by disulfide bonds which comprise: (1) in terms of the heavy chains, a variable region (abbreviated herein as "$V_H$") and a heavy chain constant region which comprises three domains, $C_{H1}$, $C_{H2}$, and $C_{H3}$; and (2) in terms of the light chains, a light chain variable region (abbreviated herein as "$V_L$") and a light chain constant region which comprises one domain, $C_L$.

Antibody fragments and, more specifically, antigen binding fragments are molecules possessing an antibody variable region or segment thereof (which comprises one or more of the disclosed CDR 3 domains, heavy and/or light within framework regions of heavy and/or light chains, as appropriate), which confers selective binding to PCSK9, and particularly human and/or murine PCSK9. Antibody fragments containing such an antibody variable region include, but are not limited to the following antibody molecules: a Fab, a F(ab')$_2$, a Fd, a Fv, a scFv, bispecific antibody molecules (antibody molecules comprising a PCSK9-specific antibody or antigen binding fragment as disclosed herein linked to a second functional moiety having a different binding specificity than the antibody, including, without limitation, another peptide or protein such as an antibody, or receptor ligand), a bispecific single chain Fv dimer, an isolated CDR3, a minibody, a 'scAb', a dAb fragment, a diabody, a triabody, a tetrabody, a minibody, and artificial antibodies based upon protein scaffolds, including but not limited to fibronectin type III polypeptide antibodies (see, e.g., U.S. Pat. No. 6,703,199 and International Application Numbers WO 02/32925 and WO 00/34784) or cytochrome B; see, e.g., Nygren et al., 1997 *Curr. Opinion Struct. Biol.* 7:463-469; the disclosures of which are incorporated herein by reference. The antibody portions or binding fragments may be natural, or partly or wholly synthetically produced. Such antibody portions can be prepared by various means known by one of skill in the art, including, but not limited to, conventional techniques, such as papain or pepsin digestion.

The term "isolated" as used herein in reference to antibody molecules, PCSK9-specific antagonists in general, encoding nucleic acid or other describes a property as it pertains to the disclosed PCSK9-specific antagonists, nucleic acid or other that makes them different from that found in nature. The difference can be, for example, that they are of a different purity than that found in nature, or that they are of a different structure or form part of a different structure than that found in nature. A structure not found in nature, for example, includes recombinant human immunoglobulin structures including, but not limited to, recombinant human immunoglobulin structures with optimized CDRs. Other examples of structures not found in nature are PCSK9-specific antagonists or nucleic acid substantially free of other cellular material. Isolated PCSK9-specific antagonists are generally free of other protein-specific antagonists having different protein specificities (i.e., possess an affinity for other than PCSK9).

In one particular aspect, the present invention provides isolated PCSK9-specific antagonists which antagonize PCSK9 function. In particular embodiments, said PCSK9-specific antagonists inhibit human and/or murine PCSK9's antagonism of cellular LDL uptake by interfering with PCSK9 binding to the LDL receptor and resultant PCSK9 cell internalization. Disclosed PCSK9-specific antagonists, thus, form desirable molecules for lowering plasma LDL-cholesterol levels; see, e.g., Cohen et al., 2005 *Nat. Genet.* 37:161-165 (wherein significantly lower plasma LDL cholesterol levels were noted in individuals heterozygous for a nonsense mutation in allele PCSK9); Rashid et al., 2005 *Proc. Natl. Acad. Sci. USA* 102:5374-5379 (wherein PCSK9-knockout mice evidenced increased numbers of LDLRs in hepatocytes, accelerated plasma LDL clearance, and significantly lower plasma cholesterol levels); and Cohen et al., 2006 *N. Engl. J. Med.* 354:1264-1272 (wherein humans heterozygous for mutated, loss of function, PCSK9 exhibited a significant reduction in the long-term risk of developing atherosclerotic heart disease).

Through repeat experiments, 1D05 antibody molecules as disclosed herein dose-dependently inhibited the effects of both human and/or murine PCSK9 on LDL uptake. In specific embodiments, the present invention, thus, encompasses PCSK9-specific antagonists and, in more specific embodiments, antibody molecules comprising the heavy and/or light chain variable regions (SEQ ID NO: 11 and 27, respectively) contained within these 1D05 antibody molecules or the heavy and/or light chains, e.g., amino acids 1-233 of SEQ ID NO: 9 (or SEQ ID NO: 9) and SEQ ID NO: 1, respectively, or SEQ ID NOs: 25 and 26, respectively, as well as equivalents (characterized as having one or more conservative amino acid substitutions that do not degrade the PCSK9-selective property of 1D05) or homologs thereof. Particular embodiments comprise isolated PCSK9-specific antagonists that comprise the CDR domains disclosed herein or sets of heavy and/or light chain CDR domains disclosed herein, or equivalents thereof, characterized as having one or more conservative amino acid substitutions.

Use of the terms "domain" or "region" herein simply refers to the respective portion of the antibody molecule wherein the sequence or segment at issue will reside or, in the alternative, currently resides.

In specific embodiments, the present invention provides isolated PCSK9-specific antagonists and, in more specific embodiments, antibody molecules comprising a heavy chain variable region which comprises SEQ ID NO: 11; equivalents thereof characterized as having one or more conservative amino acid substitutions, and homologs thereof. The disclosed antagonists should counteract or inhibit human and/or murine PCSK9-dependent inhibition of cellular LDL uptake. In specific embodiments, the present invention provides homologs of the disclosed antagonists characterized as being at least 90% identical over the heavy chain variable region to SEQ ID NO: 11; said antagonists which inhibit human and/or murine PCSK9-dependent inhibition of cellular LDL uptake by at least 10%.

In specific embodiments, the present invention provides isolated PCSK9-specific antagonists and, in more specific embodiments, antibody molecules comprising a light chain variable region which comprises SEQ ID NO: 27; equivalents thereof characterized as having one or more conservative amino acid substitutions, and homologs thereof. The disclosed antagonists should counteract or inhibit human and/or murine PCSK9-dependent inhibition of cellular LDL uptake. In specific embodiments, the present invention provides homologs of the disclosed antagonists characterized as being at least 90% identical over the light chain variable region to SEQ ID NO: 27; said antagonists which inhibit human and/or murine PCSK9-dependent inhibition of cellular LDL uptake by at least 10%.

In specific embodiments, the present invention provides isolated PCSK9-specific antibody molecules which comprise a heavy chain variable region comprising SEQ ID NO: 11 and a light chain variable region comprising SEQ ID NO: 27; or equivalents thereof characterized as having one or more conservative amino acid substitutions in the prescribed sequences. Specific embodiments are said antagonists which inhibit human and/or murine PCSK9-dependent inhibition of cellular LDL uptake by at least 10%. In specific embodiments, the present invention provides homologs of the disclosed antagonists characterized as being at least 90% identical over the heavy and light chain variable regions to SEQ ID NOs: 11 and 27, respectively; said antagonists which inhibit human and/or murine PCSK9-dependent inhibition of cellular LDL uptake by at least 10%.

In particular embodiments, the present invention provides isolated PCSK9-specific antagonists and, in more specific embodiments, PCSK9 antibody molecules that comprise variable heavy CDR3 sequence SEQ ID NO: 17; and equivalents thereof characterized as having one or more conservative amino acid substitutions; specific embodiments of which inhibit human and/or murine PCSK9-dependent inhibition of cellular LDL uptake by at least 10%. Specific embodiments provide isolated antagonists which additionally comprise in the heavy chain variable region CDR1 and/or CDR2 sequences comprising SEQ ID NO: 13 and/or SEQ ID NO: 15, respectively; or equivalents thereof characterized as having one or more conservative amino acid substitutions in any one or more of the CDR sequences. In specific embodiments, the present invention provides homologs of the disclosed antagonists characterized as being at least 90% identical over the CDR3 sequences or within each of the CDR1, CDR2 and CDR3 sequences to SEQ ID NO: 17 or SEQ ID NOs: 13, 15 and 17, respectively, as appropriate; said antagonists which inhibit human and/or murine PCSK9-dependent inhibition of cellular LDL uptake by at least 10%.

In particular embodiments, the present invention provides isolated PCSK9-specific antagonists and, in more specific embodiments, antibody molecules which comprise variable light CDR3 sequence which comprises SEQ ID NO: 7; and equivalents thereof characterized as having one or more conservative amino acid substitutions; specific embodiments of which inhibit human and/or murine PCSK9-dependent inhibition of cellular LDL uptake by at least 10%. Specific embodiments provide isolated antagonists which additionally comprise in the light chain variable region CDR1 and/or CDR2 sequences comprising SEQ ID NO: 3 and/or SEQ ID NO: 5, respectively; or an equivalent thereof characterized as having one or more conservative amino acid substitutions in any one or more of the CDR sequences. In specific embodiments, the present invention provides homologs of the disclosed antagonists characterized as being at least 90% identical over the CDR3 sequences or within each of the CDR1, CDR2 and CDR3 sequences to SEQ ID NO: 7 or SEQ ID NOs: 3, 5 and 7, respectively, as appropriate; said antagonists which inhibit human and/or murine PCSK9-dependent inhibition of cellular LDL uptake by at least 10%.

In particular embodiments, the present invention provides isolated PCSK9-specific antagonists and, in more specific embodiments, antibody molecules which comprise heavy chain variable region CDR3 sequence and light chain variable region CDR3 sequence comprising SEQ ID NOs: 17 and 7, respectively; or equivalents thereof characterized as having one or more conservative amino acid substitutions in any one or more of the CDR3 sequences; specific embodiments of which inhibit human and/or murine PCSK9-dependent inhibition of cellular LDL uptake by at least 10%. In specific embodiments, the present invention provides homologs of the disclosed antagonists characterized as being at least 90% identical over the heavy and light chain variable region CDR3 sequences to SEQ ID NOs: 17 and 7, respectively; said antagonists which inhibit human and/or murine PCSK9-dependent inhibition of cellular LDL uptake by at least 10%.

Specific embodiments provide isolated PCSK9-specific antagonists and, in more specific embodiments, antibody molecules which comprise heavy chain variable region CDR1, CDR2, and CDR3 sequences and light chain variable region CDR1, CDR2, and CDR3 sequences comprising SEQ ID NOs: 13, 15, 17, 3, 5 and 7, respectively; and equivalents thereof characterized as having one or more conservative amino acid substitutions in any one or more of the CDR sequences; specific embodiments of which inhibit human and/or murine PCSK9-dependent inhibition of cellular LDL uptake by at least 10%. In specific embodiments, the present invention provides homologs of the disclosed antagonists characterized as being at least 90% identical over the heavy and light chain variable region CDR1, CDR2 and CDR3 sequences to SEQ ID NOs: 13, 15, 17, 3, 5 and 7, respectively; said antagonists which inhibit human and/or murine PCSK9-dependent inhibition of cellular LDL uptake by at least 10%.

One particular aspect of the present invention encompasses isolated PCSK9-specific antagonists and, in more specific embodiments, antibody molecules which are variants of that disclosed above which comprise a heavy chain variable region CDR3 sequence of SEQ ID NO: 45 wherein the CDR3 sequence is not SEQ ID NO: 17; specific embodiments of which inhibit human and/or murine PCSK9-dependent inhibition of cellular LDL uptake by at least 10%. Further embodiments hereof additionally comprise heavy chain variable region CDR1 sequence of SEQ ID NO: 43 wherein the variant sequence is not SEQ ID NO: 13 and/or heavy chain variable region CDR2 sequence of SEQ ID NO: 44 wherein the variant sequence is not SEQ ID NO: 15; specific embodiments of which inhibit human and/or murine PCSK9-dependent inhibition of cellular LDL uptake by at least 10%. In other embodiments, the present invention encompasses heavy chain variable region sequence comprising CDR1, CDR2, and CDR3 sequence which, respectively, comprises SEQ ID NOs: 43, 44 and 45 in the respective regions, which are, respectively, not SEQ ID NOs:13, 15 and 17; specific embodiments of which inhibit human and/or murine PCSK9-dependent inhibition of cellular LDL uptake by at least 10%.

Another aspect of the present invention encompasses isolated PCSK9-specific antagonists and, in more specific embodiments, antibody molecules which are variants of that disclosed above which comprise a light chain variable region CDR3 sequence of SEQ ID NO: 48 wherein the CDR3 sequence is not SEQ ID NO: 7; specific embodiments of which inhibit human and/or murine PCSK9-dependent inhibition of cellular LDL uptake by at least 10%. Further embodiments hereof additionally comprise light chain variable region CDR1 sequence of SEQ ID NO: 46 wherein the variant sequence is not SEQ ID NO: 3 and/or light chain variable region CDR2 sequence of SEQ ID NO: 47 wherein the variant sequence is not SEQ ID NO: 5; specific embodiments of which inhibit human and/or murine PCSK9-dependent inhibition of cellular LDL uptake by at least 10%. In other embodiments, the present invention encompasses light chain variable region sequence comprising CDR1, CDR2 and CDR3 sequence which, respectively, comprises SEQ ID NOs: 46, 47 and 48 in the respective regions, which are, respectively, not SEQ ID NOs: 3, 5 and 7; specific embodiments of which inhibit human and/or murine PCSK9-dependent inhibition of cellular LDL uptake by at least 10%.

Additional distinct embodiments encompass isolated PCSK9-specific antagonists which comprise: (a) a heavy chain variable region comprising CDR1, CDR2 and CDR3 sequence, wherein (i) the CDR1 sequence comprises SEQ ID NO: 13 or SEQ ID NO: 43; SEQ ID NO: 43 being different in sequence from SEQ ID NO: 13; (ii) the CDR2 sequence comprises SEQ ID NO: 15 or SEQ ID NO: 44; SEQ ID NO: 44 being different in sequence from SEQ ID NO: 15; and (iii) the CDR3 sequence comprises SEQ ID NO: 17 or SEQ ID NO: 45; SEQ ID NO: 45 being different in sequence from SEQ ID NO: 17; and/or (b) a light chain variable region comprising CDR1, CDR2 and CDR3 sequence, wherein (i) the CDR1 sequence comprises SEQ ID NO: 3 or SEQ ID NO: 46; SEQ ID NO: 46 being different in sequence from SEQ ID NO: 3; (ii) the CDR2 sequence comprises SEQ ID NO: 5 or SEQ ID NO: 47; SEQ ID NO: 47 being different in sequence from SEQ ID NO: 5; and (iii) the CDR3 sequence comprises SEQ ID NO: 7 or SEQ ID NO: 48; SEQ ID NO: 48 being different in sequence from SEQ ID NO: 7; specific embodiments of which inhibit human and/or murine PCSK9-dependent inhibition of cellular LDL uptake by at least 10%.

Other aspects of the present invention encompass isolated PCSK9-specific antagonists and, in more specific embodiments, antibody molecules which are variants of that disclosed above which comprise (i) a heavy chain variable region sequence comprising CDR1, CDR2, and CDR3 sequence which, respectively, comprises SEQ ID NOs: 43, 44 and 45 in the respective regions, which are, respectively, not SEQ ID NOs:13, 15 and 17; and (ii) a light chain variable region sequence comprising CDR1, CDR2 and CDR3 sequence which, respectively, comprises SEQ ID NOs: 46, 47 and 48 in the respective regions, which are, respectively, not SEQ ID NOs: 3, 5 and 7; specific embodiments of which inhibit human and/or murine PCSK9-dependent inhibition of cellular LDL uptake by at least 10%.

In specific embodiments herein the CDRs are in place of the corresponding regions of 1D05 with out without conservative amino acid substitutions; specific embodiments of which inhibit human and/or murine PCSK9-dependent inhibition of cellular LDL uptake by at least 10%. In particular embodiments, the present invention encompasses isolated PCSK9-specific antagonists and, in more specific embodiments, antibody molecules comprising heavy and/or light chain variable regions comprising SEQ ID NOs: 50 and 49, respectively; said variants SEQ ID NOs which are not SEQ ID NOs: 11 and 27, respectively; specific embodiments of which inhibit human and/or murine PCSK9-dependent inhibition of cellular LDL uptake by at least 10%.

Specific embodiments include any isolated PCSK9-specific antagonist and, in more specific embodiments, antibody molecules which comprise heavy chain variable region sequence found in any of SEQ ID NOs: 51-56, optionally comprising a light chain variable region sequence disclosed herein (e.g., SEQ ID NO: 27); specific embodiments of which inhibit human and/or murine PCSK9-dependent inhibition of cellular LDL uptake by at least 10%. Other embodiments include any isolated PCSK9-specific antagonist and, in more specific embodiments, antibody molecules which comprise light chain variable region sequence found in any of SEQ ID NOs: 57-60, optionally comprising a heavy chain variable region sequence disclosed herein (e.g., SEQ ID NO: 11); specific embodiments of which inhibit human and/or murine PCSK9-dependent inhibition of cellular LDL uptake by at least 10%.

Particular embodiments are isolated PCSK9-specific antagonists which comprise the above-described VH and VL regions in a full length antibody. Specific embodiments herein further comprise a series of amino acids selected from the group consisting of: SEQ ID NO: 21 (IgG1), SEQ ID NO: 22 (IgG2), SEQ ID NO: 23 (IgG4) and SEQ ID NO: 24 (IgG2 m4).

Conservative amino acid substitutions, as one of ordinary skill in the art will appreciate, are substitutions that replace an amino acid residue with one imparting similar or better (for the intended purpose) functional and/or chemical characteristics. Antagonists bearing such conservative amino acid substitutions can be tested for retained or better activity using functional assays available in the art or described herein. PCSK9-specific antagonists possessing one or more conservative amino acid substitutions which retain the ability to selectively bind to human PCSK9 and antagonize PCSK9 functioning at a level the same or better than 1D05 antibody molecules as described herein are referred to herein as "functional equivalents" of the disclosed antagonists and form specific embodiments of the present invention. Conservative amino acid substitutions are often ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Such modifications are not designed to significantly reduce or alter the binding or functional inhibition characteristics of the PCSK9-specific antagonist, albeit they may improve such properties. The purpose for making a substitution is not significant and can include, but is by no means limited to, replacing a residue with one better able to maintain or enhance the structure of the molecule, the charge or hydrophobicity of the molecule, or the size of the molecule. For instance, one may desire simply to substitute a less desired residue with one of the same polarity or charge. Such modifications can be introduced by standard techniques known in the art, such as site-directed mutagenesis and PCR-mediated mutagenesis. One specific means by which those of skill in the art accomplish conservative amino acid substitutions is alanine scanning mutagenesis as discussed in, for example, MacLennan et al., 1998 *Acta Physiol. Scand. Suppl.* 643:55-67, and Sasaki et al., 1998 *Adv. Biophys.* 35:1-24.

In another aspect, the present invention provides isolated PCSK9-specific antagonists and, in more specific embodiments, antibody molecules which comprise heavy and/or light chain variable regions comprising amino acid sequences that are homologous to the corresponding amino acid sequences of the disclosed antibodies, wherein the antibody molecules inhibit PCSK9-dependent inhibition of cellular LDL uptake. Specific embodiments are antagonists which comprise heavy and/or light chain variable regions which are at least 90% identical to disclosed heavy and/or light chain variable regions, respectively. Reference to "at least 90% identical" includes at least 90, 91, 92, 93, 94, 95, 96, 97, 98, 99 and 100% identical sequences along the full length of the molecule disclosed herein.

PCSK9-specific antagonists with amino acid sequences homologous to the amino acid sequences of antagonists described herein are typically produced to improve one or more of the properties of the antagonist without negatively impacting its specificity for PCSK9. One method of obtaining such sequences, which is not the only method available to the skilled artisan, is to mutate sequence encoding the PCSK9-specific antagonist or specificity-determining region(s) thereof, express an antagonist comprising the mutated sequence(s), and test the encoded antagonist for retained function using available functional assays including those described herein. Mutation may be by site-directed or random mutagenesis. As one of skill in the art will appreciate, however, other methods of mutagenesis can readily bring about the same effect. For example, in certain methods, the spectrum of mutants are constrained by non-randomly targeting conservative substitutions based on either amino acid chemical or structural characteristics, or else by protein structural considerations. In affinity maturation experiments, several such mutations may be found in a single selected molecule, whether they are randomly or non-randomly selected. There are also various structure-based approaches toward affinity maturation as demonstrated in, e.g., U.S. Pat. No. 7,117,096, PCT Pub. Nos.: WO 02/084277 and WO 03/099999; the disclosures of which are incorporated herein by reference.

As used herein, the percent homology between two amino acid or nucleic acid sequences is equivalent to the percent identity between the two sequences, and these two terms will be used interchangeably throughout. As used herein, % identity of two nucleic acid or amino acid sequences is determined using the algorithm of Karlin and Altschul (Proc. Natl. Acad. Sci. USA 90:5873-5877, 1993). Such an algorithm is incorporated into the NBLAST and XBLAST programs of Altschul et al., 1990 *J. Mol. Biol.* 215:403-410. BLAST nucleotide searches are performed with the NBLAST program, score=100, wordlength=12, to obtain nucleic acid sequences homologous to a nucleic acid molecule of the invention. BLAST protein searches are performed with the XBLAST program, score=50, wordlength=3, to obtain amino acid sequences homologous to an amino acid sequence disclosed herein. To obtain gapped alignments for comparison purposes, Gapped BLAST is utilized as described in Altschul et al., 1997 *Nucleic Acids Res.* 25:3389-3402. When utilizing BLAST and Gapped BLAST programs, the default parameters of the respective programs (e.g., XBLAST and NBLAST) are used.

Utilization of components of one or more disclosed PCSK9-specific molecules to produce other binding molecules with similar or better specificity is well within the realm of one skilled in the art. This can be accomplished, for example, using techniques of recombinant DNA technology. One specific example of this involves the introduction of DNA encoding the immunoglobulin variable region, or one or more of the CDRs, of an antibody to the variable region, constant region, or constant region plus framework regions, as appropriate, of a different immunoglobulin. Such molecules form important aspects of the present invention. Specific immunoglobulins or the corresponding sequences, into which particular disclosed sequences may be inserted or, in the alternative, form the essential part of, include but are not limited to the following antibody molecules which form particular embodiments of the present invention: a Fab (monovalent fragment with variable light (VL), variable heavy (VH), constant light (CL) and constant heavy 1 (CH1) domains), a F(ab')$_2$ (bivalent fragment comprising two Fab fragments linked by a disulfide bridge or alternative at the hinge region), a Fd (VH and CH1 domains), a Fv (VL and VH domains), a scFv (a single chain Fv where VL and VH are joined by a linker, e.g., a peptide linker, see, e.g., Bird et al., 1988 *Science* 242:423-426, Huston et al., 1988 *PNAS USA* 85:5879-5883), a bispecific antibody molecule (an antibody molecule comprising a PCSK9-specific antibody or antigen binding fragment as disclosed herein linked to a second functional moiety having a different binding specificity than the antibody, including, without limitation, another peptide or protein such as an antibody, or receptor ligand), a bispecific single chain Fv dimer (see, e.g., PCT/US92/09965), an isolated CDR3, a minibody (single chain-CH3 fusion that self assembles into a bivalent dimer of about 80 kDa), a 'scAb' (an antibody fragment containing VH and VL as well as either CL or CH1), a dAb fragment (VH domain, see, e.g., Ward et al., 1989 *Nature* 341:544-546, and McCafferty et al., 1990 *Nature* 348:552-554; or VL domain; Holt et al., 2003 *Trends in Biotechnology* 21:484-489), a diabody (see, e.g., Holliger et al., 1993 *PNAS USA* 90:6444-6448 and International Application Number WO 94/13804), a triabody, a tetrabody, a minibody (a scFv joined to a CH3; see, e.g., Hu et al., 1996 *Cancer Res.* 56:3055-3061), IgG, IgG1, IgG2, IgG3, IgG4, IgM, IgD, IgA, IgE or any derivatives thereof, and artificial antibodies based upon protein scaffolds, including but not limited to fibronectin type III polypeptide antibodies (see, e.g., U.S. Pat. No. 6,703,199 and International Application Number WO 02/32925) or cytochrome B; see, e.g., Koide et al., 1998 *J. Molec. Biol.* 284:1141-1151, and Nygren et al., 1997 *Current Opinion in Structural Biology* 7:463-469; the disclosures of which are incorporated herein by reference. Certain antibody molecules including, but not limited to, Fv, scFv, diabody molecules or domain antibodies (Domantis) may be stabilized by incorporating disulfide bridges to line the VH and VL domains, see, e.g., Reiter et al., 1996 *Nature Biotech.* 14:1239-1245; the disclosure of which is incorporated herein by reference. Bispecific antibodies may be produced using conventional technologies (see, e.g., Holliger & Winter, 1993 *Current Opinion Biotechnol.* 4:446-449, specific methods of which include production chemically, or from hybrid hybridomas) and other technologies including, but not limited to, the BiTE™ technology (molecules possessing antigen binding regions of different specificity with a peptide linker) and knobs-into-holes engineering (see, e.g., Ridgeway et al., 1996 *Protein Eng.* 9:616-621; the disclosure of which is incorporated herein by reference). Bispecific diabodies may be produced in *E. coli*, and these molecules as other PCSK9-specific antagonists, as one of skill in the art will appreciate, may be selected using phage display in the appropriate libraries (see, e.g., International Application Number WO 94/13804; the disclosure of which is incorporated herein by reference).

Variable domains, into which CDRs of interest are inserted, may be obtained from any germ-line or rearranged human variable domain. Variable domains may also be synthetically produced. The CDR regions can be introduced into the respective variable domains using recombinant DNA technology. One means by which this can be achieved is described in Marks et al., 1992 *Bio/Technology* 10:779-783; the disclosure of which is incorporated herein by reference. A variable heavy domain may be paired with a variable light domain to provide an antigen binding site. In addition, independent regions (e.g., a variable heavy domain alone) may be used to bind antigen. The artisan is well aware, as well, that two domains of an Fv fragment, VL and VH, while perhaps coded by separate genes, may be joined, using recombinant methods, by a synthetic linker that enables them to be made as a single protein chain in which the VL and VH regions pair to form monovalent molecules (scFvs).

Specific embodiments provide the CDR(s) in germline framework regions. Framework regions, including but not limited to human framework regions, are known to those of skill in the art (e.g., a human or non-human framework). The framework regions may be naturally occurring or consensus framework regions. In one aspect, the framework region of an antibody of the invention is human (see, e.g., Clothia et al., 1998 *J. Mol. Biol.* 278:457-479 for a listing of human framework regions; said disclosure of which is incorporated herein by reference in its entirety). Specific embodiments herein provide heavy chain variable CDR3 SEQ ID NO: 17 into VH1A_3 in place of the relevant CDR. Specific embodiments herein provide heavy chain variable CDR1, CDR2 and/or CDR3 sequences (SEQ ID NO:s 13, 15 and 17, respectively) into VH1A_3 in place of the relevant CDRs. Specific embodiments herein provide light chain variable CDR3 SEQ ID NO: 7 into VK1_4 in place of the relevant CDR. Specific embodiments herein provide light chain variable CDR1, CDR2 and/or CDR3 sequences (SEQ ID NO:s 3, 5 and 7, respectively) into VK1_4 in place of the relevant CDRs. Specific embodiments further provide heavy chain variable CDR3 SEQ ID NO: 17 and light chain variable CDR3 SEQ ID NO: 7 into VH1A_3 and VK1_4 germline sequences, respectively. Further embodiments, provide heavy chain variable CDR1, CDR2 and/or CDR3 sequences (SEQ ID NO:s 13, 15 and 17, respectively) into VH1A_3 in place of the relevant CDRs; and light chain variable CDR1, CDR2 and/or CDR3 sequences (SEQ ID NO:s 3, 5 and 7, respectively) into VK1_4 in place of the relevant CDRs.

The present invention encompasses antibody molecules that are human, humanized, deimmunized, chimeric and primatized. The invention also encompasses antibody molecules produced by the process of veneering; see, e.g., Mark et al., 1994 Handbook of Experimental Pharmacology, vol. 113: The pharmacology of monoclonal Antibodies, Springer-Verlag, pp. 105-134; the disclosure of which is incorporated herein by reference. "Human" in reference to the disclosed antibody molecules specifically refers to antibody molecules having variable and/or constant regions derived from human germline immunoglobulin sequences, wherein said sequences may, but need not, be modified/altered to have certain amino acid substitutions or residues that are not encoded by human germline immunoglobulin sequence. Such mutations can be introduced by methods including, but not limited to, random or site-specific mutagenesis in vitro, or by somatic mutation in vivo. Specific examples of mutation techniques discussed in the literature are that disclosed in Gram et al., 1992 *PNAS USA* 89:3576-3580; Barbas et al., 1994 *PNAS USA* 91:3809-3813, and Schier et al., 19961 *Mol. Biol.* 263:551-567; the disclosures of which are incorporated herein by reference. These are only specific examples and do not represent the only available techniques. There are a plethora of mutation techniques in the scientific literature which are available to, and widely appreciated by, the skilled artisan. "Humanized" in reference to the disclosed antibody molecules refers specifically to antibody molecules wherein CDR sequences derived from another mammalian species, such as a mouse, are grafted onto human framework sequences. "Primatized" in reference to the disclosed antibody molecules refers to antibody molecules wherein CDR sequences of a non-primate are inserted into primate framework sequences, see, e.g., WO 93/02108 and WO 99/55369; the disclosures of which are incorporated herein by reference.

Specific antibodies of the present invention are monoclonal antibodies and, in particular embodiments, are in one of the following antibody formats: IgD, IgA, IgE, IgM, IgG1, IgG2, IgG3, IgG4 or any derivative of any of the foregoing. The language "derivatives thereof" or "derivatives" in this respect includes, inter alia, (i) antibodies and antibody molecules with conservative modifications in one or both variable regions (i.e., VH and/or VL), (ii) antibodies and antibody molecules with manipulations in the constant regions of the heavy and/or light chains, and/or (iii) antibodies and antibody molecules that contain additional chemical moieties which are not normally a part of the immunoglobulin molecule (e.g., pegylation).

Manipulations of the variable regions can be within one or more of the VH and/or VL CDR regions. Site-directed mutagenesis, random mutagenesis or other method for generating sequence or molecule diversity can be utilized to create mutants which can subsequently be tested for a particular functional property of interest in available in vitro or in vivo assays including those described herein.

Antibodies of the present invention also include those in which modifications have been made to the framework residues within VH and/or VL to improve one or more properties of the antibody of interest. Typically, such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. Such "backmutated" antibodies are also intended to be encompassed by the invention. Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al; the disclosure of which is incorporated herein by reference.

In addition or alternative to modifications made within the framework or CDR regions, antibodies of the invention may be engineered to include modifications within the Fc or constant regions, where present, typically to alter one or more functional properties of the antibody, such as serum half-life, complement fixation, Fc receptor binding, and/or antigen-dependent cellular cytotoxicity.

The concept of generating "hybrids" or "combinatorial" IgG forms comprising various antibody isotypes to hone in on desired effector functionality has generally been described; see, e.g., Tao et al., 1991 *J. Exp. Med.* 173:1025-1028. A specific embodiment of the present invention encompasses antibody molecules that possess specific manipulations in the Fc region which have been found to result in reduced or altered binding to FcγR receptors, C1q or FcRn on the part of the antibody. The present invention, therefore, encompasses antibodies in accordance with the present description that do not provoke (or provoke to a lesser extent) antibody-dependent cellular cytotoxicity ("ADCC"), complement-mediated cytotoxicity ("CMC"), or form immune complexes, while retaining normal pharmacokinetic ("PK") properties. Specific embodiments of the present invention provide an antibody molecule as defined in accordance with the present invention which comprises, as part of its immunoglobulin structure, SEQ ID NO: 24 and, in particular embodiments, residues 107-326 of SEQ ID NO: 24 as part of the immunoglobulin structure. The present invention encompasses antibody molecules which comprise: (i) a light chain comprising SEQ ID NO: 1, and (ii) a heavy chain comprising SEQ ID NO: 11 in sequence with (adjacent to) or followed by a series of amino acids selected from the group consisting of: SEQ ID NO: 21 (IgG1), SEQ ID NO: 22 (IgG2), SEQ ID NO: 23 (IgG4) and SEQ ID NO: 24 (IgG2m4). FIG. 6 illustrates a comparison of sequence comprising SEQ ID NO: 24, particularly IgG2m4, with IgG1, IgG2, and IgG4. Amino acid sequences for mature, secreted anti-PCSK9 IgG2m4 heavy and light chains can be found as SEQ ID NOs: 25 and 26, respectively. Antibody molecules encoded at least in part by said sequence are encompassed herein.

Specific PCSK9-specific antagonists may carry a detectable label, or may be conjugated to a toxin (e.g., a cytotoxin), a radioactive isotope, a radionuclide, a liposome, a targeting moiety, a biosensor, a cationic tail, or an enzyme (e.g., via a peptidyl bond or linker). Such PCSK9-specific antagonist compositions form an additional aspect of the present invention.

In another aspect, the present invention provides isolated nucleic acid encoding disclosed PCSK9-specific antagonists. "Isolated" as mentioned prior refers to the property of the thing referred to that makes them different from that found in nature. The difference can be, for example, that they are of a different purity than that found in nature, or that they are of a different structure or form part of a different structure than that found in nature. An example of nucleic acid not found in nature is, for example, nucleic acid substantially free of other cellular material. The nucleic acid may be present in whole cells, in a cell lysate, or in a partially purified or substantially pure form. In specific instances, a nucleic acid may be isolated when purified away from other cellular components or other contaminants, e.g., other cellular nucleic acids or proteins, for example, using standard techniques, including without limitation, alkaline/SDS treatment, CsCl banding, column chromatography, agarose gel electrophoresis and other suitable methods known in the art. The nucleic acid may include DNA (inclusive of cDNA) and/or RNA. Nucleic acids of the present invention can be obtained using standard molecular biology techniques. For antibodies expressed by hybridomas (e.g., hybridomas prepared from transgenic mice carrying human immunoglobulin genes), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

The present invention encompasses isolated nucleic acid encoding disclosed variable heavy and/or light chains and select components thereof, particularly the disclosed variable or respective CDR regions and, in particular CDR3. In specific embodiments hereof, the CDR(s) are provided within antibody framework regions and, in particular embodiments, human framework regions. Specific embodiments provide isolated nucleic acid encoding the CDR(s) into germline framework regions including, but not limited to, human germline framework regions. Specific embodiments herein provide isolated nucleic acid encoding heavy chain CDR SEQ ID NO: 17 (in specific embodiments, said nucleic acid of which comprises SEQ ID NO: 18) into VH1A_3 in place of the nucleic acid encoding the relevant CDR. Specific embodiments herein provide nucleic acid encoding heavy chain variable CDR1, CDR2 and/or CDR3 sequences SEQ ID NOs: 13, 15 and 17, respectively (and, in particular embodiments, said nucleic acid of which comprises SEQ ID NOs: 14, 16 and 18, respectively) into VH1A_3 in place of the relevant CDRs. Specific embodiments herein provide isolated nucleic acid encoding light chain CDR SEQ ID NO: 7 (in specific embodiments, said nucleic acid of which comprises SEQ ID NO: 8) into VK1_4 in place of the nucleic acid encoding the relevant CDR. Specific embodiments herein provide nucleic acid encoding light chain variable CDR1, CDR2 and/or CDR3 sequences SEQ ID NOs: 3, 5 and 7, respectively (and, in particular embodiments, said nucleic acid of which comprises SEQ ID NOs: 4, 6 and 8, respectively) into VK1_4 in place of the relevant CDRs. Specific embodiments further provide heavy chain variable CDR3 SEQ ID NO: 17 (and, in particular embodiments, said nucleic acid of which comprises SEQ ID NO: 18) and light chain variable CDR3 SEQ ID NO: 7 (and, in particular embodiments, said nucleic acid of which comprises SEQ ID NO: 8) into VH1A3 and VK1_4 germline sequences, respectively. Further embodiments provide heavy chain variable CDR1, CDR2 and/or CDR3 sequences SEQ ID NOs: 13, 15 and 17, respectively (and, in particular embodiments, said nucleic acid of which comprises SEQ ID NOs: 14, 16 and 18, respectively) into VH1A_3 in place of the relevant CDRs; and light chain variable CDR1, CDR2 and/or CDR3 sequences SEQ ID NOs: 3, 5 and 7, respectively (and, in particular embodiments, said nucleic acid of which comprises SEQ ID NOs: 4, 6 and 8, respectively) into VK1_4 in place of the relevant CDRs.

The isolated nucleic acid encoding the variable regions can be provided within any desired antibody molecule format including, but not limited to, the following: F(ab')$_2$, a Fab, a Fv, a scFv, bispecific antibody molecules (antibody molecules comprising a PCSK9-specific antibody or antigen binding fragment as disclosed herein linked to a second functional moiety having a different binding specificity than the antibody, including, without limitation, another peptide or protein such as an antibody, or receptor ligand), a bispecific single chain Fv dimer, a minibody, a dAb fragment, diabody, triabody or tetrabody, a minibody, IgG, IgG1, IgG2, IgG3, IgG4, IgM, IgD, IgA, IgE or any derivatives thereof.

Specific embodiments provide isolated nucleic acid which encodes PCSK9-specific antagonists and, in more specific embodiments, antibody molecules comprising a heavy chain variable domain which comprises SEQ ID NO: 11; specific embodiments of which comprise nucleic acid sequence SEQ ID NO: 12. Specific embodiments of the present invention provide isolated nucleic acid encoding PCSK9-specific antagonists and, in more specific embodiments, antibody molecules, which additionally comprise: (i) nucleic acid encoding heavy chain CDR1 amino acid sequence SEQ ID NO: 13 (specific embodiments of which comprise nucleic acid SEQ ID NO: 14) and/or (ii) nucleic acid encoding heavy chain CDR2 amino acid sequence SEQ ID NO: 15 (specific embodiments of which comprise nucleic acid SEQ ID NO: 16). Specific embodiments provide isolated nucleic acid encoding PCSK9-specific antagonists and, in more specific embodiments, antibody molecules comprising a light chain variable domain which comprises SEQ ID NO: 27; specific embodiments of which comprise nucleic acid sequence SEQ ID NO: 28. Specific embodiments of the present invention provide isolated nucleic acid encoding PCSK9-specific antagonists and, in more specific embodiments, antibody molecules, which additionally comprise: (i) nucleic acid encoding light chain CDR1 amino acid sequence SEQ ID NO: 3 (specific embodiments of which comprise nucleic acid SEQ ID NO: 4) and/or (ii) nucleic acid encoding light chain CDR2 amino acid sequence SEQ ID NO: 5 (specific embodiments of which comprise nucleic acid SEQ ID NO: 6). Specific embodiments provide isolated nucleic acid encoding PCSK9-specific antagonists and, in more specific embodiments, antibody molecules which comprise a heavy chain variable domain which comprises SEQ ID NO: 11; specific embodiments of which comprise nucleic acid sequence SEQ ID NO: 12; and a light chain variable domain which comprises SEQ ID NO: 27; specific embodiments of which comprise nucleic acid sequence SEQ ID NO: 28. Specific embodiments provide isolated nucleic acid encoding (i) heavy chain CDR1, CDR2 and/or CDR3 sequences (SEQ ID NOs: 13, 15 and 17, respectively; specific embodiments of which comprise nucleic acid SEQ ID NOs: 14, 16 and/or 18, respectively) preferably in a framework region (including but not limited to a human framework region); and (ii) light chain CDR1, CDR2 and/or CDR3 sequences (SEQ ID NO: 3, 5 and 7, respectively; specific embodiments of which comprise nucleic acid SEQ ID NOs: 4, 6 and/or 8, respectively) preferably in a framework region (including but not limited to a human framework region). The present invention further provides in specific embodiments, homologs of the antagonists disclosed above, characterized as being at least 90% identical over the heavy and/or light chain variable regions, or the CDR regions, as appropriate, whichever is present to the corresponding sequences of 1D05.

Additional embodiments provide isolated nucleic acid encoding PCSK9-specific antagonists and, in more specific embodiments, antibody molecules which comprise a light chain comprising SEQ ID NO: 1 (specific embodiments of which comprise nucleic acid SEQ ID NO: 2) and a heavy chain or Fd chain comprising amino acids 1-233 of SEQ ID NO: 9, or SEQ ID NO: 9 (specific embodiments of which comprise nucleic acid 1-699 of SEQ ID NO: 10, or SEQ ID NO: 10, respectively). Further embodiments provide isolated nucleic acid encoding PCSK9-specific antagonists and, in more specific embodiments, antibody molecules which comprise a light chain comprising SEQ ID NO: 26 (specific embodiments of which comprise SEQ ID NO: 30) and a heavy chain comprising SEQ ID NO: 25 (specific embodiments of which comprise SEQ ID NO: 29). The present invention further provides in specific embodiments, homologs of the antagonists disclosed above, characterized as being at least 90% identical over the heavy and/or light chains to the corresponding sequences of 1D05.

Specific embodiments of the present invention encompass nucleic acid encoding antibody molecules that possess manipulations in the Fc region which result in reduced or altered binding to FcγR receptors, C1q, or FcRn on the part of the antibody. One specific embodiment of the present invention is isolated nucleic acid which encodes for antibody molecules comprising as part of their immunoglobulin structure SEQ ID NO: 24 and, in particular embodiments, residues 107-326 of SEQ ID NO: 24. In specific embodiments, synthetic PCSK9-specific antagonists can be produced by expression from nucleic acid generated from oligonucleotides synthesized and assembled within suitable expression vectors; see, e.g., Knappick et al., 2000 *J. Mol. Biol.* 296:57-86, and Krebs et al., 2001 *J. Immunol. Methods* 254:67-84.

The present invention encompasses nucleic acid encoding antibody molecules which comprise: (i) nucleic acid encoding a light chain comprising SEQ ID NO: 1 (specific embodiments of which comprise nucleic acid SEQ ID NO: 2), and (ii) nucleic acid encoding a heavy chain comprising SEQ ID NO: 11 (specific embodiments of which comprise nucleic acid SEQ ID NO: 12) followed in sequence by (adjacent to) a set of nucleotides encoding for a set of amino acids selected from the group consisting of: SEQ ID NO: 21 (IgG1), SEQ ID NO: 22 (IgG2), SEQ ID NO: 23 (IgG4) and SEQ ID NO: 24 (IgG2m4). Nucleotide sequences for mature, secreted anti-PCSK9 IgG2m4 heavy and light chains can be found as SEQ ID NOs: 29 and 30, respectively. Plasmid sequences comprising heavy and light chain 1D05 anti-PCSK9 IgG2m4 antibody molecules can be found as SEQ ID NOs: 31 and 32, respectively. Nucleic acid encoding such antibody molecules form important embodiments hereof.

Also included within the present invention are isolated nucleic acids comprising nucleotide sequences which are at least about 90% identical and more preferably at least about 95% identical to the full length of the nucleotide sequences described herein, and which nucleotide sequences encode PCSK9-specific antagonists which inhibit PCSK9-dependent inhibition of cellular LDL uptake by at least 10%.

Reference to "at least about 90% identical" throughout the application includes at least about 90, 91, 92, 93, 94, 95, 96, 97, 98, 99 or 100% identical.

The invention further provides isolated nucleic acid at least a portion of which hybridizes to the complement of nucleic acid consisting of SEQ ID NO: 12 and/or SEQ ID NO: 28 under stringent hybridization conditions, said nucleic acid of which confers upon antibody molecules the ability to specifically bind PCSK9 and antagonize PCSK9 function, and PCSK9-specific antagonists expressed employing said nucleic acid. Methods for hybridizing nucleic acids are well-known in the art; see, e.g., Ausubel, *Current Protocols in Molecular Biology*, John Wiley & Sons, N.Y., 6.3.1-6.3.6, 1989. Stringent hybridization conditions involve hybridizing at 68° C. in 5×SSC/5× Denhardt's solution (or equivalent)/ 1.0% SDS, and washing in 0.2×SSC/0.1% SDS at room temperature. Moderately stringent conditions include washing in 3×SSC at 42° C. The parameters of salt concentration and temperature can be varied to achieve the optimal level of identity between the probe and the target nucleic acid. The skilled artisan can manipulate various hybridization and/or washing conditions to specifically target nucleic acid in the hybridizing portion that is at least 80, 85, 90, 95, 98, or 99% identical to SEQ ID NO: 12 and/or SEQ ID NO: 28. Basic parameters affecting the choice of hybridization conditions and guidance for devising suitable conditions are set forth by Sambrook et al., *Molecular Cloning: A Laboratory Manual*, Cold Spring Harbor Laboratory Press, Cold Spring Harbor, N.Y., chapters 9 and 11, 1989 and Ausubel et al. (eds), *Current Protocols in Molecular Biology*, John Wiley & Sons, Inc., sections 2.10 and 6.3-6.4, 1995 (the disclosures of which are incorporated herein by reference), and can be readily determined by those having ordinary skill in the art. PCSK9 antagonists having one or more variable regions comprising nucleic acid which hybridizes to the complement of nucleic acid consisting of SEQ ID NO: 12 and/or SEQ ID NO: 28 under stringent hybridization conditions should be effective in antagonizing one or more functions of PCSK9. Said antagonists and encoding nucleic acid, thus, form important embodiments of the present invention.

In another aspect, the present invention provides vectors comprising the nucleic acid disclosed herein. Vectors in accordance with the present invention include, but are not limited to, plasmids and other expression constructs (e.g., phage or phagemid, as appropriate) suitable for the expression of the desired antibody molecule at the appropriate level for the intended purpose; see, e.g., Sambrook & Russell, *Molecular Cloning: A Laboratory Manual: 3rd Edition*, Cold Spring Harbor Laboratory Press; the disclosure of which is incorporated herein by reference. For most cloning purposes, DNA vectors may be used. Typical vectors include plasmids, modified viruses, bacteriophage, cosmids, yeast artificial chromosomes, bacterial artificial chromosomes, and other forms of episomal or integrated DNA. It is well within the purview of the skilled artisan to determine an appropriate vector for a particular gene transfer, generation of a recombinant PCSK9-specific antagonist, or other use. In specific embodiments, in addition to a recombinant gene, the vector may also contain an origin of replication for autonomous replication in a host cell, appropriate regulatory sequences, such as a promoter, a termination sequence, a polyadenylation sequence, an enhancer sequence, a selectable marker, a limited number of useful restriction enzyme sites, and/or other sequences as appropriate and the potential for high copy number. Examples of expression vectors for the production of protein-specific antagonists are well known in the art; see, e.g., Persic et al., 1997 *Gene* 187:9-18; Boel et al., 2000 *J. Immunol. Methods* 239:153-166, and Liang et al., 2001 *J. Immunol. Methods* 247:119-130; the disclosures of which are incorporated herein by reference. If desired, nucleic acid encoding the antagonist may be integrated into the host chromosome using techniques well known in the art; see, e.g., Ausubel, *Current Protocols in Molecular Biology*, John Wiley & Sons, 1999, and Marks et al., International Application Number WO 95/17516. Nucleic acid may also be expressed on plasmids maintained episomally or incorporated into an artificial chromosome; see, e.g., Csonka et al., 2000 *J. Cell Science* 113:3207-3216; Vanderbyl et al., 2002 *Molecular Therapy* 5:10. Specifically with regards to antibody molecules, the antibody light chain gene and the antibody heavy chain gene can be inserted into separate vectors or, more typically, both genes may be inserted into the same expression vector. Nucleic acid encoding any PCSK9-specific antagonist or component thereof can be inserted into an expression vector using standard methods (e.g., ligation of complementary restriction sites on the nucleic acid fragment and vector, or blunt end ligation if no restriction sites are present). Another specific example of how this may be carried out is through use of recombinational methods, e.g. the Clontech "InFusion" system, or Invitrogen "TOPO" system (both in vitro), or intracellularly (e.g. the Cre-Lox system). Specifically with regards to antibody molecules, the light and heavy chain variable regions can be used to create full-length antibody genes of any antibody isotype by inserting them into expression vectors already encoding heavy chain constant and light chain constant regions of the desired isotype such that the VH segment is operatively linked to the CH segment(s) within the vector and the VL segment is operatively linked to the CL segment within the vector. Additionally or alternatively, the recombinant expression vector comprising nucleic acid encoding a PCSK9-specific antagonist can encode a signal peptide that facilitates secretion of the antagonist from a host cell. The nucleic acid can be cloned into the vector such that the nucleic acid encoding a signal peptide is linked in-frame adjacent to the PCSK9-specific antagonist-encoding nucleic acid. The signal peptide may be an immunoglobulin or a non-immunoglobulin signal peptide. Any technique available to the skilled artisan may be employed to introduce the nucleic acid into the host cell; see, e.g., Morrison, 1985 *Science*, 229:1202. Methods of subcloning nucleic acid molecules of interest into expression vectors, transforming or transfecting host cells containing the vectors, and methods of making substantially pure protein comprising the steps of introducing the respective expression vector into a host cell, and cultivating the host cell under appropriate conditions are well known. The PCSK9-specific antagonist so produced may be harvested from the host cells in conventional ways. Techniques suitable for the introduction of nucleic acid into cells of interest will depend on the type of cell being used. General techniques include, but are not limited to, calcium phosphate transfection, DEAE-Dextran, electroporation, liposome-mediated transfection and transduction using viruses appropriate to the cell line of interest (e.g., retrovirus, vaccinia, baculovirus, or bacteriophage).

In another aspect, the present invention provides isolated cell(s) comprising nucleic acid encoding disclosed PCSK9-specific antagonists. A variety of different cell lines are contemplated herein and can be used for the recombinant production of PCSK9-specific antagonists, including but not limited to those from prokaryotic organisms (e.g., *E. coli*, *Bacillus*, and *Streptomyces*) and from eukaryotic (e.g., yeast, Baculovirus, and mammalian); see, e.g., Breitling et al., Recombinant antibodies, John Wiley & Sons, Inc. and Spektrum Akademischer Verlag, 1999; the disclosure of which is incorporated herein by reference. Plant cells, including transgenic plants, and animal cells, including transgenic animals (other than humans), comprising the nucleic acid or antagonists disclosed herein are also contemplated as part of the present invention. Suitable mammalian cells or cell lines including, but not limited to, those derived from Chinese Hamster Ovary (CHO cells, including but not limited to DHFR-CHO cells (described in Urlaub and Chasin, 1980 *Proc. Natl. Acad. Sci. USA* 77:4216-4220) used, for example, with a DHFR selectable marker (e.g., as described in Kaufman and Sharp, 1982 *Mol. Biol.* 159:601-621), NS0 myeloma cells (where a GS expression system as described in WO 87/04462, WO 89/01036, and EP 338,841 may be used), COS cells, SP2 cells, HeLa cells, baby hamster kidney cells, YB2/0 rat myeloma cells, human embryonic kidney cells, human embryonic retina cells, and others comprising the nucleic acid or antagonists disclosed herein form additional embodiments of the present invention; the preceding cited disclosures of which are incorporated herein by reference. Specific embodiments of the present invention comprising nucleic acid encoding disclosed PCSK9-specific antagonists include, but are not limited to, *E. coli*; see, e.g., Plückthun, 1991 *Bio/Technology* 9:545-551, or yeast, such as *Pichia*, and recombinant derivatives thereof (see, e.g., Li et al., 2006 *Nat. Biotechnol.* 24:210-215); the preceding disclosures of which are incorporated herein by reference. Specific embodiments of the present invention relate to eukaryotic cells comprising nucleic acid encoding the disclosed PCSK9-specific antagonists, see, Chadd & Chamow, 2001 *Current Opinion in Biotechnology* 12:188-194, Andersen & Krummen, 2002 *Current Opinion in Biotechnology* 13:117, Larrick & Thomas, 2001 *Current Opinion in Biotechnology* 12:411-418; the disclosures of which are incorporated herein by reference. Specific embodiments of the present invention relate to mammalian cells comprising nucleic acid encoding the disclosed PCSK9-specific antagonists which are able to produce PCSK9-specific antagonists with proper post translational modifications. Post translational modifications include, but are by no means limited to, disulfide bond formation and glycosylation. Another type of post translational modification is signal peptide cleavage. Preferred embodiments herein have the appropriate glycosylation; see, e., Yoo et al., 2002 *J. Immunol. Methods* 261:1-20; the disclosure of which is incorporated herein by reference. Naturally occurring antibodies contain at least one N-linked carbohydrate attached to a heavy chain. Id. Different types of mammalian host cells can be used to provide for efficient post-translational modifications. Examples of such host cells include Chinese Hamster Ovary (CHO), HeLa, C6, PC12, and myeloma cells; see, Yoo et al., 2002 J. Immunol. Methods 261:1-20, and Persic et al., 1997 Gene 187:9-18; the disclosures of which are incorporated herein by reference.

In another aspect, the present invention provides isolated cell(s) comprising a polypeptide of the present invention.

In another aspect, the present invention provides a method of making a PCSK9-specific antagonist of the present invention, which comprises incubating a cell comprising nucleic acid encoding the PCSK9-specific antagonist, or a heavy and/or light chain or a fragment thereof (e.g., VH and/or VL, or one or more of the disclosed heavy and/or light chain variable region CDRs) of a desired PCSK9-specific antagonist (dictated by the desired antagonist) with specificity for human and/or murine PCSK9 under conditions that allow the expression of the PCSK9-specific antagonist, or the expression and assembly of said heavy and/or light chains or fragment into a PCSK9-specific antagonist, and isolating said PCSK9-specific antagonist from the cell. One example by which to generate particular desired heavy and/or light chain sequence or fragment is to first amplify (and modify) the germline heavy and/or light chain variable sequences or fragment using PCR. Germline sequence for human heavy and/or light variable regions are readily available to the skilled artisan, see, e.g., the "Vbase" human germline sequence database, and Kabat, E. A. et al., 1991 *Sequences of Proteins of Immunological Interest*, Fifth Edition, U.S. Department of Health and Human Services, NIH Publication No. 91-3242; Tomlinson, I. M. et al., 1992 "The Repertoire of Human Germline VH Sequences Reveals about Fifty Groups of VH Segments with Different Hypervariable Loops" *J. Mol. Biol.* 227:776-798; and Cox, J. P. L. et al., 1994 "A Directory of Human Germ-line Vκ Segments Reveals a Strong Bias in their Usage" *Eur. J. Immunol.* 24:827-836; the disclosures of which are incorporated herein by reference. Mutagenesis of germline sequences may be carried out using standard methods, e.g., PCR-mediated mutagenesis where the mutations are incorporated into PCR primers, or site-directed mutagenesis. If full-length antibodies are desired, sequence is available for the human heavy chain constant region genes; see, e.g., Kabat. E. A. et al., 1991 *Sequences of Proteins of Immunological Interest*, Fifth Edition, U.S. Department of Health and Human Services, NIH Publication No. 91-3242. Fragments containing these regions may be obtained, for example, by standard PCR amplification. Alternatively, the skilled artisan can avail him/herself of vectors already encoding heavy and/or light chain constant regions.

Available techniques exist to recombinantly produce other antibody molecules which retain the specificity of an original antibody. A specific example of this is where DNA encoding the immunoglobulin variable region or the CDRs is introduced into the constant regions, or constant regions and framework regions, or simply the framework regions, of another antibody molecule; see, e.g., EP-184,187, GB 2188638, and EP-239400; the disclosures of which are incorporated herein by reference. Cloning and expression of antibody molecules, including chimeric antibodies, are described in the literature; see, e.g., EP 0120694 and EP 0125023; the disclosures of which are incorporated herein by reference.

Antibody molecules in accordance with the present invention may, in one instance, be raised and then screened for characteristics identified herein using known techniques. Basic techniques for the preparation of monoclonal antibodies are described in the literature, see, e.g., Kohler and Milstein (1975, *Nature* 256:495-497); the disclosure of which is incorporated herein by reference. Fully human monoclonal antibodies can be produced by available methods. These methods include, but are by no means limited to, the use of genetically engineered mouse strains which possess an immune system whereby the mouse antibody genes have been inactivated and in turn replaced with a repertoire of functional human antibody genes, while leaving other components of the mouse immune system unchanged. Such genetically engineered mice allow for the natural in vivo immune response and affinity maturation process which results in high affinity, full human monoclonal antibodies. This technology is well known in the art and is fully detailed in various publications, including but not limited to U.S. Pat. Nos. 5,545,806; 5,569,825; 5,625,126; 5,633,425; 5,789,650; 5,877,397; 5,661,016; 5,814,318; 5,874,299; 5,770,249 (assigned to GenPharm International and available through Medarex, under the umbrella of the "UltraMab Human Antibody Development System"); as well as U.S. Pat. Nos. 5,939,598; 6,075,181; 6,114,598; 6,150,584 and related family members (assigned to Abgenix, disclosing their XenoMouse® technology); the disclosures of which are incorporated herein by reference. See also reviews from Kellerman and Green, 2002 *Curr. Opinion in Biotechnology* 13:593-597, and Kontermann & Stefan, 2001 *Antibody Engineering*, Springer Laboratory Manuals; the disclosures of which are incorporated herein by reference.

Alternatively, a library of PCSK9-specific antagonists in accordance with the present invention may be brought into contact with PCSK9, and ones able to demonstrate specific binding selected. Functional studies can then be carried out to ensure proper functionality, e.g., inhibition of PCSK9-dependent inhibition of cellular LDL uptake. There are various techniques available to the skilled artisan for the selection of protein-specific molecules from libraries using enrichment technologies including, but not limited to, phage display (e.g., see technology from Cambridge Antibody Technology ("CAT") disclosed in U.S. Pat. Nos. 5,565,332; 5,733,743; 5,871,907; 5,872,215; 5,885,793; 5,962,255; 6,140,471; 6,225,447; 6,291,650; 6,492,160; 6,521,404; 6,544,731; 6,555,313; 6,582,915; 6,593,081, as well as other U.S. family members and/or applications which rely on priority filing GB 9206318, filed May 24, 1992; see also Vaughn et al., 1996, *Nature Biotechnology* 14:309-314), ribosome display (see, e.g., Hanes and Pluckthün, 1997 *Proc. Natl. Acad. Sci.* 94:4937-4942), bacterial display (see, e.g., Georgiou, et al., 1997 *Nature Biotechnology* 15:29-34) and/or yeast display (see, e.g., Kieke, et al., 1997 *Protein Engineering* 10:1303-1310); the preceding disclosures of which are incorporated herein by reference. A library, for example, can be displayed on the surface of bacteriophage particles, with nucleic acid encoding the PCSK9-specific antagonist or fragment thereof expressed and displayed on its surface. Nucleic acid may then be isolated from bacteriophage particles exhibiting the desired level of activity and the nucleic acid used in the development of desired antagonist. Phage display has been thoroughly described in the literature; see, e.g., Kontermann & Stefan, supra, and International Application Number WO 92/01047; the disclosures of which are incorporated herein by reference. Specifically with regard to antibody molecules, individual heavy or light chain clones in accordance with the present invention may also be used to screen for complementary heavy or light chains, respectively, capable of interaction therewith to form a molecule of the combined heavy and light chains; see, e.g., International Application Number WO 92/01047. Any method of panning which is available to the skilled artisan may be used to identify PCSK9-specific antagonists. Another specific method for accomplishing this is to pan against the target antigen in solution, e.g. biotinylated, soluble PCSK9, and then capture the PCSK9-specific antagonist-phage complexes on streptavidin-coated magnetic beads, which are then washed to remove nonspecifically-bound phage. The captured phage can then be recovered from the beads in the same way they would be recovered from the surface of a plate, (e.g. DTT) as described herein.

PCSK9-specific antagonists may be purified by techniques available to one of skill in the art. Titers of the relevant antagonist preparation, ascites, hybridoma culture fluids, or relevant sample may be determined by various serological or immunological assays which include, but are not limited to, precipitation, passive agglutination, enzyme-linked immunosorbent antibody ("ELISA") techniques and radioimmunoassay ("RIA") techniques.

The present invention relates in part to methods employing PCSK9-specific antagonists described herein for antagonizing PCSK9 function; said methods of which are further described below. Use of the term "antagonizing" throughout the present application refers to the act of opposing, inhibiting, counteracting, neutralizing or curtailing one or more functions of PCSK9. Inhibition or antagonism of one or more of PCSK9-associated functional properties can be readily determined according to methodologies known to the art (see, e.g., Barak & Webb, 1981 *J. Cell Biol.* 90:595-604; Stephan & Yurachek, 1993 *J. Lipid Res.* 34:325330; and McNamara et al., 2006 *Clinica Chimica Acta* 369:158-167) as well as those described herein. Inhibition or antagonism will effectuate a decrease in PCSK9 activity relative to that seen in the absence of the antagonist or, for example, that seen when a control antagonist of irrelevant specificity is present. Preferably, a PCSK9-specific antagonist in accordance with the present invention antagonizes PCSK9 functioning to the point that there is a decrease of at least 10%, of the measured parameter including but not limited to the activities disclosed herein, and more preferably, a decrease of at least 20%, 30%, 40%, 50%, 60%, 70%, 80%, 90% and 95% of the measured parameter. Such inhibition/antagonism of PCSK9 functioning is particularly effective in those instances where PCSK9 functioning is contributing at least in part to a particular phenotype, disease, disorder or condition which is negatively impacting the subject.

In one aspect, the present invention provides a method for antagonizing the activity of PCSK9, which comprises contacting a cell, population of cells or tissue sample capable of being affected by PCSK9 (i.e., which expresses and/or comprises LDL receptors) with a PCSK9-specific antagonist disclosed herein under conditions that allow said antagonist to bind to PCSK9 when present and inhibit PCSK9's inhibition of cellular LDL uptake. Specific embodiments of the present invention include such methods wherein the cell is a human cell. Additional embodiments of the present invention include such methods wherein the cell is a murine cell.

In another aspect, the present invention provides a method for antagonizing the activity of PCSK9 in a subject, which comprises administering to the subject a therapeutically effective amount of a PCSK9-specific antagonist of the present invention. In specific embodiments, the methods for antagonizing PCSK9 function are for the treatment of a PCSK9-associated disease, disorder or condition or, alternatively, a disease, disorder or condition that could benefit from the effects of a PCSK9 antagonist. The medicament would be useful in a subject(s) exhibiting a condition associated with PCSK9 activity, or a condition where the functioning of PCSK9 is contraindicated for a particular subject. In select embodiments, the condition may be hypercholesterolemia, coronary heart disease, metabolic syndrome, acute coronary syndrome or related conditions.

The present invention, thus, contemplates the use of PCSK9-specific antagonists described herein in various methods of treatment where antagonizing PCSK9 function is desirable. The method of treatment can be prophylactic or therapeutic in nature. In specific embodiments, the present invention relates to a method of treatment for a condition associated with/attributed to PCSK9 activity, or a condition where the functioning of PCSK9 is contraindicated for a particular subject, which comprises administering to the subject a therapeutically effective amount of a PCSK9-specific antagonist of the present invention. In select embodiments, the condition may be hypercholesterolemia, coronary heart disease, metabolic syndrome, acute coronary syndrome or related conditions.

Methods of treatment in accordance with the present invention comprise administering to an individual a therapeutically (or prophylactically) effective amount of a PCSK9-specific antagonist of the present invention. Use of the terms "therapeutically effective" or "prophylactically effective" in reference to an amount refers to the amount necessary at the intended dosage to achieve the desired therapeutic/prophylactic effect for the period of time desired. The desired effect may be, for example, amelioration of at least one symptom associated with the treated condition. These amounts will vary, as the skilled artisan will appreciate, according to various factors, including but not limited to the disease state, age, sex and weight of the individual, and the ability of the PCSK9-specific antagonist to elicit the desired effect in the individual. The response may be documented by in vitro assay, in vivo non-human animal studies, and/or further supported from clinical trials.

The PCSK9-specific antagonist may be administered as a pharmaceutical composition. The present invention, thus, provides a pharmaceutically acceptable composition comprising a PCSK9-specific antagonist of the invention and a pharmaceutically acceptable carrier including but not limited to an excipient, diluent, stabilizer, buffer, or alternative designed to facilitate administration of the antagonist in the desired format and amount to the treated individual.

The pharmaceutical composition may be formulated by any number of strategies known in the art, see, e.g., McGoff and Scher, 2000 *Solution Formulation of Proteins/Peptides*: In—McNally, E. J., ed. Protein Formulation and Delivery. New York, N.Y.: Marcel Dekker; pp. 139-158; Akers & Defilippis, 2000, *Peptides and Proteins as Parenteral Solutions*. In—Pharmaceutical Formulation Development of Peptides and Proteins. Philadelphia, Pa.: Taylor and Francis; pp. 145-177; Akers et al., 2002, *Pharm. Biotechnol.* 14:47-127. A pharmaceutically acceptable composition suitable for patient administration will contain an effective amount of the PCSK9-specific antagonist in a formulation which both retains biological activity while also promoting maximal stability during storage within an acceptable temperature range.

The antagonist-based pharmaceutically acceptable composition may, in particular embodiments, be in liquid or solid form, or in the form of gas particles or aerosolized particles. Any technique for production of liquid or solid formulations may be utilized. Such techniques are well within the realm of the abilities of the skilled artisan. Solid formulations may be produced by any available method including, but not limited to, lyophilization, spray drying, or drying by supercritical fluid technology. Solid formulations for oral administration may be in any form rendering the antagonist accessible to the patient in the prescribed amount and within the prescribed period of time. The oral formulation can take the form of a number of solid formulations including, but not limited to, a tablet, capsule, or powder. Solid formulations may alternatively be lyophilized and brought into solution prior to administration for either single or multiple dosing according to methods well known to the skilled artisan. Antagonist compositions should generally be formulated within a biologically relevant pH range and may be buffered to maintain a proper pH range during storage. Both liquid and solid formulations generally require storage at lower temperatures (e.g., 2-8° C.) in order to retain stability for longer periods. Formulated antagonist compositions, especially liquid formulations, may contain a bacteriostat to prevent or minimize proteolysis during storage, including but not limited to effective concentrations (e.g., ≤1% w/v) of benzyl alcohol, phenol, m-cresol, chlorobutanol, methylparaben, and/or propylparaben. A bacteriostat may be contraindicated for some patients. Therefore, a lyophilized formulation may be reconstituted in a solution either containing or not containing such a component. Additional components may be added to either a buffered liquid or solid antagonist formulation, including but not limited to sugars as a cryoprotectant (including but not limited to polyhydroxy hydrocarbons such as sorbitol, mannitol, glycerol, and dulcitol and/or disaccharides such as sucrose, lactose, maltose, or trehalose) and, in some instances, a relevant salt (including but not limited to NaCl, KCl, or LiCl). Such antagonist formulations, especially liquid formulations slated for long term storage, will rely on a useful range of total osmolarity to both promote long term stability at temperatures of, for example, 2-8° C. or higher, while also making the formulation useful for parenteral injection. As appropriate, preservatives, stabilizers, buffers, antioxidants and/or other additives may be included. The formulations may contain a divalent cation (including but not limited to MgCl2, CaCl2, and MnCl2); and/or a non-ionic surfactant (including but not limited to Polysorbate-80 (Tween 80™), Polysorbate-60 (Tween 60™), Polysorbate-40 (Tween 40™), and Polysorbate-20 (Tween 20™), polyoxyethylene alkyl ethers, including but not limited to Brij 58™, Brij35™, as well as others such as Triton X-100™, Triton X-114™, NP40™, Span 85 and the Pluronic series of non-ionic surfactants (e.g., Pluronic 121)). Any combination of such components form specific embodiments of the present invention.

Pharmaceutical compositions in liquid format may include a liquid carrier, e.g., water, petroleum, animal oil, vegetable oil, mineral oil, or synthetic oil. The liquid format may also include physiological saline solution, dextrose or other saccharide solution or glycols, such as ethylene glycol, propylene glycol or polyethylene glycol.

Preferably, the pharmaceutical composition may be in the form of a parenterally acceptable aqueous solution that is pyrogen-free with suitable pH, tonicity, and stability. Pharmaceutical compositions may be formulated for administration after dilution in isotonic vehicles, for example, Sodium Chloride Injection, Ringer's Injection, or Lactated Ringer's Injection.

One aspect of the present invention is a pharmaceutical composition which comprises: (i) about 50 to about 200 mg/mL of a PCSK9-specific antagonist described herein; (ii) a polyhydroxy hydrocarbon (including but not limited to sorbitol, mannitol, glycerol and dulcitol) and/or a disaccharide (including but not limited to sucrose, lactose, maltose and trehalose); the total of said polyhydroxy hydrocarbon and/or disaccharide being about 1% to about 6% weight per volume ("w/v") of the formulation; (iii) about 5 mM to about 200 mM of histidine, imidazole, phosphate or acetic acid which serves as a buffering agent to prevent pH drift over the shelf life of the pharmaceutical composition and as a tonicity modifier; (iv) about 5 mM to about 200 mM of arginine, proline, phenylalanine, alanine, glycine, lysine, glutamic acid, aspartic acid or methionine to counteract aggregation; (v) about 0.01M to about 0.1M of hydrochloric acid ("HCl") in an amount sufficient to achieve a pH in the range of about 5.5 to about 7.5; and (vi) a liquid carrier including but not limited to sterile water, petroleum, animal oil, vegetable oil, mineral oil, synthetic oil, physiological saline solution, dextrose or other saccharide solution or glycols, such as ethylene glycol, propylene glycol or polyethylene glycol; wherein said pharmaceutical composition has a pH in the range of about 5.5 to about 7.5; and wherein said pharmaceutical composition optionally comprises about 0.01% to about 1% w/v of the formulation of a non-ionic surfactant (including but not limited to Polysorbate-80 (Tween 80™), Polysorbate-60 (Tween 60™), Polysorbate-40 (Tween 40™), and Polysorbate-20 (Tween 20™), polyoxyethylene alkyl ethers, including but not limited to Brij 58™, Brij35™, as well as others such as Triton X-100™, Triton X-114™, NP40™, Span 85 and the Pluronic series of non-ionic surfactants (e.g., Pluronic 121)).

HCl may be added as free acid, Histidine-HCl or Arginine-HCl. Where supplied as Histidine-HCl or Arginine-HCl, the total amounts of Histidine or Arginine in the HCl form should be that specified above. Accordingly, some or all of the HCl depending on the amounts of Histidine and/or Arginine may be supplied as Histidine-HCl and/or Arginine-HCl; as appropriate. Use of the term "about" with respect to amounts disclosed in the specification means within 10% of the specified numbers provided. A range provided as, for example" in "about 50 to about 200" expressly includes as distinct embodiments each number within said range. As such in the above example, embodiments including but not limited to those having 50, 100, 125, 150 and 200 form specific embodiments herein. Pharmaceutical compositions as disclosed herein have general applicability despite the mode of administration. In specific embodiments, the disclosed pharmaceutical compositions are useful for subcutaneous administration as a liquid or upon reconstitution of a lyophilized form. In specific embodiments, PCSK9-specific antagonists employed in the disclosed formulations may be pegylated or form part of fusion proteins.

Specific aspects of the present invention relate to the above disclosed pharmaceutical compositions which comprise: (i) about 50 to about 200 mg/mL of a PCSK9-specific antagonist described herein; (ii) about 1% to about 6% (in particular embodiments from about 2% to about 6%) w/v mannitol, trehalose or sucrose; (iii) about 10 mM to about 100 mM of histidine; (iv) about 25 mM to about 100 mM of arginine or proline; (v) about 0.02 M to about 0.05M of hydrochloric acid ("HCl") in an amount sufficient to achieve a pH in the range of about 5.8 to about 7; and (vi) a liquid carrier including but not limited to sterile water, petroleum, animal oil, vegetable oil, mineral oil, synthetic oil, physiological saline solution, dextrose or other saccharide solution or glycols, such as ethylene glycol, propylene glycol or polyethylene glycol; wherein said pharmaceutical composition has a pH in the range of about 5.8 to about 7; and wherein said pharmaceutical composition optionally comprising about 0.01% to about 1% w/v of the formulation of a non-ionic surfactant (including but not limited to Polysorbate-80 (Tween 80™), Polysorbate-60 (Tween 60™), Polysorbate-40 (Tween 40™), and Polysorbate-20 (Tween 20™), polyoxyethylene alkyl ethers, including but not limited to Brij 58™, Brij35™, as well as others such as Triton X-100™, Triton X-114™, NP40™, Span 85 and the Pluronic series of non-ionic surfactants (e.g., Pluronic 121)).

Specific embodiments provide pharmaceutical compositions which comprise: (i) 50 to 200 mg/mL of a PCSK9-specific antagonist described herein; (ii) about 1% to about 6% (in particular embodiments from about 2% to about 6%) w/v mannitol, trehalose or sucrose; (iii) about 10 mM to about 150 mM of histidine; (iv) about 10 mM to about 150 mM of arginine or proline; (v) about 0.03 M to about 0.05 M of hydrochloric acid ("HCl") in an amount sufficient to achieve a pH in the range of about 5.8 to about 6.5; and (vi) a liquid carrier including but not limited to sterile water, petroleum, animal oil, vegetable oil, mineral oil, synthetic oil, physiological saline solution, dextrose or other saccharide solution or glycols, such as ethylene glycol, propylene glycol or polyethylene glycol; wherein said pharmaceutical composition has a pH in the range of about 5.8 to about 6.5; and wherein said pharmaceutical composition optionally comprising about 0.01% to about 1% w/v of Polysorbate-80 (Tween 80™) or Polysorbate-20 (Tween 20™).

Specific embodiments herein provide pharmaceutical compositions which comprise: (i) 50 to 200 mg/mL of a PCSK9-specific antagonist described herein; (ii) about 1% to about 6% (in particular embodiments from about 2% to about 6%) w/v sucrose; (iii) about 25 mM to about 100 mM of histidine; (iv) about 25 mM to about 100 mM of arginine; (v) about 0.040 M to about 0.045 M of hydrochloric acid ("HCl") in an amount sufficient to achieve a pH of about 6; and (vi) sterile water; wherein said pharmaceutical composition has a pH of about 6; and wherein said pharmaceutical composition optionally comprising about 0.01% to about 1% w/v of Polysorbate-80 (Tween 80™) or Polysorbate-20 (Tween 20™). In specific embodiments thereof, the levels of histidine and arginine are within 25 mM of each other and, in other embodiments are the same.

Specific embodiments herein provide pharmaceutical compositions which comprise (i) 50 to 200 mg/mL of a PCSK9-specific antagonist described herein; (ii) sucrose, histidine and arginine in one of the following amounts: (a) about 1% w/v sucrose, about 10 mM histidine and about 25 mM arginine; (b) about 2% w/v sucrose, about 25 mM histidine and about 25 mM arginine; (c) about 3% w/v sucrose, about 50 mM histidine and about 50 mM arginine; or (d) about 6% w/v sucrose, about 100 mM histidine and about 100 mM arginine; (iii) about 0.04 mol or, alternatively, about 1.46 g of HCl; and (iv) sterile water; wherein said pharmaceutical composition has a pH of about 6; and wherein said pharmaceutical composition optionally comprising about 0.01% to about 1% w/v of Polysorbate-80 (Tween 80™) or Polysorbate-20 (Tween 20™). Specific embodiments herein are wherein the amounts of sucrose, histidine and arginine in (ii) above are that described in (c) or (d).

Specific embodiments herein provide pharmaceutical compositions as described which comprise 50 to 200 mg/ml of any one of the various PCSK9-specific antagonists described herein. For purposes of exemplification of one distinct embodiment thereof, and not to be construed as a limitation, is the following: a pharmaceutical formulation as described above which comprises: a PCSK9-specific antagonist which comprises: (a) a light chain comprising SEQ ID NO: 26; and (b) a heavy chain comprising SEQ ID NO: 25; wherein said PCSK9-specific antagonist is an antibody molecule that antagonizes PCSK9's inhibition of cellular LDL uptake.

Particular embodiments herein are pharmaceutical compositions according to the above description which are lyophilized and reconstituted. In specific embodiments, said protein concentration in said lyophilized and reconstituted solution is up to 2-fold higher than in the pre-lyophilized composition. In specific embodiments, the protein or PCSK9-specific antagonist concentration in the lyophilized and/or reconstituted pharmaceutical composition is in the range of about 50 mg/mL to about 300 mg/mL. Diluents useful for reconstituting the lyophilized pharmaceutical compositions include but are not limited to sterile water, bacteriostatic water for injection ("BWFI"), phosphate-buffered saline, a sterile saline solution, physiological saline solution, Ringer's solution or dextrose solution and may in specific embodiments contain 0.01-1% (w/v) of Polysorbate-80 (Tween 80™) or Polysorbate-20 (Tween 20™). In specific embodiments, lyophilized powder can be reconstituted with 1/60.2× original volume (or 0.167 mL) up to 1× (1 mL).

Exemplary embodiments of the present invention are pharmaceutical compositions as described herein which are stable. Other embodiments of the present invention are pharmaceutical compositions as described herein which are stable to lyophilization and reconstitution. Various methods are available to the skilled artisan to prepare lyophilized compositions; see, e.g., Martin & Mo, 2007 "Stability Considerations for Lyophilized Biologics" Amer. Pharm. Rev. "Stable" as used herein refers to the property of the protein or PCSK9-specific antagonist to retain its physical or chemical stability, conformational integrity, or its ability to exhibit less denaturation, protein clipping, aggregation, fragmentation, acidic variant formation or loss of biological activity compared with a control sample at a temperature in the range of 4-37° C. for at least about 30 days. Other embodiments remain stable for up to 3 months, 6 months, 12 months, 2 years or longer periods at the above temperatures. In specific embodiments the formulation exhibits no significant changes at 2-8° C. for at least 6 months, and preferably 12 months, 2 years or longer, in order of preference. Specific embodiments experience less than 10% or, in particular embodiments, less than 5% of denaturation, protein clipping, aggregation, fragmentation, acidic variant formation or loss of biological activity compared with a control sample at a temperature in the range of 25-45° C. (or alternatively 2-8° C.) for at least about 30 days, 3 months, 6 months, 12 months, 2 years or longer. Stability of the formulations can be tested via several means known to the skilled artisan including, but not limited to Size Exclusion Chromatography (SEC-HPLC) to measure aggregation and fragmentation, Dynamic Light Scattering (DLS) to measure particle size of concentrated samples, capillary SDS-PAGE to measure fragmentation and capillary iso-electric focusing (cIEF) or cation exchange chromatography ("CEX") to measure acidic variants formation. Techniques suitable for the analysis of protein stability are well understood by those of skill in the art: see review in *Peptide and Protein Drug Delivery,* 247-301, Vincent Lee Ed., Marcel Dekker, Inc., New York, N.Y., Pubs. (1991) and Jones, 1993 *Adv. Drug Delivery Rev.* 10:29-90.

Pharmaceutical compositions as described herein should be sterile. There are various techniques available to the skilled artisan to accomplish this including, but not limited to, filtration through sterile filtration membranes. In specific embodiments, employing lyophilized and reconstituted compositions, this may be done prior to or following lyophilization and reconstitution.

Dosing of antagonist therapeutics is well within the realm of the skilled artisan, see, e.g., Lederman et al., 1991 *Int. J. Cancer* 47:659-664; Bagshawe et al., 1991 *Antibody, Immunoconjugates and Radiopharmaceuticals* 4:915-922, and will vary based on a number of factors including but not limited to the particular PCSK9-specific antagonist utilized, the patient being treated, the condition of the patient, the area being treated, the route of administration, and the treatment desired. A physician or veterinarian of ordinary skill can readily determine and prescribe the effective therapeutic amount of the antagonist. Dosage ranges may be from about 0.01 to 100 mg/kg, and more usually 0.05 to 25 mg/kg, of the host body weight. For example, dosages can be 0.3 mg/kg body weight, 1 mg/kg body weight, 3 mg/kg body weight, 5 mg/kg body weight or 10 mg/kg body weight or within the range of 1-10 mg/kg. For purposes of illustration, and not limitation, in specific embodiments, a dose of 5 mg to 2.0 g may be utilized to deliver the antagonist systemically. Optimal precision in achieving concentrations of antagonist within a range that yields efficacy without toxicity requires a regimen based on the kinetics of the drug's availability to the target site(s). This involves a consideration of the distribution, equilibrium, and elimination of the PCSK9-specific antagonist. Antagonists described herein may be used alone at appropriate dosages. Alternatively, co-administration or sequential administration of other agents may be desirable. It will be possible to present a therapeutic dosing regime for the PCSK9-specific antagonists of the present invention in conjunction with alternative treatment regimes. For example, PCSK9-specific antagonists may be used in combination or in conjunction with other drugs (therapeutic and/or prophylactic), including but not limited to cholesterol-lowering drugs, for example, cholesterol absorption inhibitors (e.g., Zetia®) and cholesterol synthesis inhibitors (e.g., Zocor® and Vytorin®). The present invention contemplates such combinations and they form an important embodiment hereof. Accordingly, the present invention relates to methods of treatment as described above where the PCSK9-specific antagonist is administered/delivered simultaneously with, following or prior to another drug or drugs (therapeutic and/or prophylactic), including but not limited to cholesterol-lowering drugs, cholesterol absorption inhibitors and cholesterol absorption inhibitors.

Individuals (subjects) capable of treatment as described herein include primates, human and non-human, and include any non-human mammal or vertebrate of commercial or domestic veterinary importance.

The PCSK9-specific antagonist may be administered to an individual by any route of administration appreciated in the art, including but not limited to oral administration, administration by injection (specific embodiments of which include intravenous, subcutaneous, intraperitoneal or intramuscular injection), administration by inhalation, intranasal, or topical administration, either alone or in combination with other agents designed to assist in the treatment of the individual. The PCSK9-specific antagonist may also be administered by injection devices, injector pens, needleless devices; and subcutaneous patch delivery systems. The route of administration should be determined based on a number of considerations appreciated by the skilled artisan including, but not limited to, the desired physiochemical characteristics of the treatment. Treatment may be provided on a daily, weekly, biweekly, or monthly basis, or any other regimen that delivers the appropriate amount of PCSK9-specific antagonist to the individual at the prescribed times such that the desired treatment is effected and maintained. The formulations may be administered in a single dose or in more than one dose at separate times.

Also contemplated are methods of using the disclosed antagonists in the manufacture of a medicament for treatment of a PCSK9-associated disease, disorder or condition or, alternatively, a disease, disorder or condition that could benefit from the effects of a PCSK9 antagonist. The medicament would be useful in a subject(s) exhibiting a condition associated with PCSK9 activity, or a condition where the functioning of PCSK9 is contraindicated for a particular subject. In select embodiments, the condition may be hypercholesterolemia, coronary heart disease, metabolic syndrome, acute coronary syndrome or related conditions.

PCSK9-specific antagonists disclosed herein may also be used as a method of diagnosis of PCSK9. In select embodiments, the present invention encompasses methods of identifying or quantifying the level of PCSK9 present in a sample (including but not limited to a biological sample, e.g., serum or blood) which comprises contacting the sample with a PCSK9-specific antagonist described herein and detecting or quantifying, respectively, binding to PCSK9. The PCSK9-specific antagonist may be used in various assay formats known to the skilled artisan and may form part of a kit (the general features of a kit of which are further described below).

The present invention further provides for the administration of disclosed anti-PCSK9 antagonists for purposes of gene therapy. Through such methods, cells of a subject are transformed with nucleic acid encoding a PCSK9-specific antagonist of the invention. Subjects comprising the nucleic acids then produce the PCSK9-specific antagonists endogenously. Previously, Alvarez, et al, *Clinical Cancer Research* 6:3081-3087, 2000, introduced single-chain anti-ErbB2 antibodies to subjects using a gene therapy approach. The methods disclosed by Alvarez, et al, supra, may be easily adapted for the introduction of nucleic acids encoding an anti-PCSK9 antibody of the invention to a subject.

Nucleic acids encoding any PCSK9-specific antagonist may be introduced to a subject.

The nucleic acids may be introduced to the cells of a subject by any means known in the art. In preferred embodiments, the nucleic acids are introduced as part of a viral vector. Examples of preferred viruses from which the vectors may be derived include lentiviruses, herpes viruses, adenoviruses, adeno-associated viruses, vaccinia virus, baculovirus, alphavirus, influenza virus, and other recombinant viruses with desirable cellular tropism.

Various companies produce viral vectors commercially, including, but by no means limited to, Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

Methods for constructing and using viral vectors are known in the art (see, e.g., Miller, et al, *BioTechniques* 7:980-990, 1992). Preferably, the viral vectors are replication defective, that is, they are unable to replicate autonomously, and thus are not infectious, in the target cell. Preferably, the replication defective virus is a minimal virus, i.e., it retains only the sequences of its genome which are necessary for encapsidating the genome to produce viral particles. Defective viruses, which entirely or almost entirely lack viral genes, are preferred. Use of defective viral vectors allows for administration to cells in a specific, localized area, without concern that the vector can infect other cells. Thus, a specific tissue can be specifically targeted.

Examples of vectors comprising attenuated or defective DNA virus sequences include, but are not limited to, a defective herpes virus vector (Karmo et al, *Cancer Gen. Ther.*

6:147-154, 1999; Kaplitt et al, *J. Neurosci. Meth.* 71:125-132, 1997 and Kaplitt et al, *J. Neuro Onc.* 19:137-147, 1994).

Adenoviruses are eukaryotic DNA viruses that can be modified to efficiently deliver a nucleic acid of the invention to a variety of cell types. Attenuated adenovirus vectors, such as the vector described by Strafford-Perricaudet et al, *J. Clin. Invest.* 90:626-630, 1992 are desirable in some instances. Various replication defective adenovirus and minimum adenovirus vectors have been described (PCT Publication Nos. WO94/26914, WO94/28938, WO94/28152, WO94/12649, WO95/02697 and WO96/22378). The replication defective recombinant adenoviruses according to the invention can be prepared by any technique known to a person skilled in the art (Levrero et al, *Gene* 101:195, 1991; EP 185573; Graham, *EMBO J.* 3:2917, 1984; Graham et al, *J. Gen. Virol.* 36:59, 1977).

The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The use of vectors derived from the AAVs for transferring genes in vitro and in vivo has been described (see Daly, et al, *Gene Ther.* 8:1343-1346, 2001, Larson et al, *Adv. Exp. Med. Bio.* 489:45-57, 2001; PCT Publication Nos. WO 91/18088 and WO 93/09239; U.S. Pat. Nos. 4,797,368 and 5,139,941 and EP 488528B1).

In another embodiment, the gene can be introduced in a retroviral vector, e.g., as described in U.S. Pat. Nos. 5,399,346, 4,650,764, 4,980,289, and 5,124,263; Mann et al, *Cell* 33:153, 1983; Markowitz et al, *J. Virol.,* 62:1120, 1988; EP 453242 and EP178220. The retroviruses are integrating viruses which infect dividing cells.

Lentiviral vectors can be used as agents for the direct delivery and sustained expression of nucleic acids encoding a PCSK9-specific antagonist of the invention in several tissue types, including brain, retina, muscle, liver and blood. The vectors can efficiently transduce dividing and nondividing cells in these tissues, and maintain long-term expression of the PCSK9-specific antagonist. For a review, see Zufferey et al, *J. Virol.* 72:9873-80, 1998 and Kafri et al, *Curr. Opin. Mol. Ther.* 3:316-326, 2001. Lentiviral packaging cell lines are available and known generally in the art. They facilitate the production of high-titer lentivirus vectors for gene therapy. An example is a tetracycline-inducible VSV-G pseudotyped lentivirus packaging cell line which can generate virus particles at titers greater than $10^6$ IU/ml for at least 3 to 4 days; see Kafri et al, *J. Virol.* 73:576-584, 1999. The vector produced by the inducible cell line can be concentrated as needed for efficiently transducing nondividing cells in vitro and in vivo.

Sindbis virus is a member of the alphavirus genus and has been studied extensively since its discovery in various parts of the world beginning in 1953. Gene transduction based on alphavirus, particularly Sindbis virus, has been well-studied in vitro (see Straus et al, *Microbiol. Rev.,* 58:491-562, 1994; Bredenbeek et al, *J. Virol.,* 67:6439-6446, 1993; Ijima et al, *Int. J. Cancer* 80:110-118, 1999 and Sawai et al, *Biochim. Biophyr. Res. Comm.* 248:315-323, 1998. Many properties of alphavirus vectors make them a desirable alternative to other virus-derived vector systems being developed, including rapid engineering of expression constructs, production of high-titered stocks of infectious particles, infection of nondividing cells, and high levels of expression (Strauss et al, 1994 supra). Use of Sindbis virus for gene therapy has been described. (Wahlfors et al, *Gene. Ther.* 7:472-480, 2000 and Lundstrom, *J. Recep. Sig. Transduct. Res.* 19(1-4):673-686, 1999.

In another embodiment, a vector can be introduced to cells by lipofection or with other transfection facilitating agents (peptides, polymers, etc.). Synthetic cationic lipids can be used to prepare liposomes for in vivo and in vitro transfection of a gene encoding a marker (Feigner et al, *Proc. Natl. Acad. Sci. USA* 84:7413-7417, 1987 and Wang et al, *Proc. Natl. Acad. Sci. USA* 84:7851-7855, 1987). Useful lipid compounds and compositions for transfer of nucleic acids are described in PCT Publication Nos. WO 95/18863 and WO 96/17823, and in U.S. Pat. No. 5,459,127.

It is also possible to introduce the vector in vivo as a naked DNA plasmid. Naked DNA vectors for gene therapy can be introduced into desired host cells by methods known in the art, e.g., electroporation, microinjection, cell fusion, DEAE dextran, calcium phosphate precipitation, use of a gene gun, or use of a DNA vector transporter (see, e.g., Wilson, et al, *J. Biol. Chem.* 267:963-967, 1992; Williams et al, *Proc. Natl. Acad. Sci. USA* 88:2726-2730, 1991). Other reagents commonly used for transfection of plasmids include, but are by no means limited to, FuGene, Lipofectin, and Lipofectamine. Receptor-mediated DNA delivery approaches can also be used (Wu et al, *J. Biol. Chem.* 263:14621-14624, 1988). U.S. Pat. Nos. 5,580,859 and 5,589,466 disclose delivery of exogenous DNA sequences, free of transfection facilitating agents, in a mammal. Recently, a relatively low voltage, high efficiency in vivo DNA transfer technique, termed electrotransfer, has been described (Vilquin et al, *Gene Ther.* 8:1097, 2001; Payen et al, *Exp. Hematol.* 29:295-300, 2001; Mir, *Bioelectrochemistry* 53:1-10, 2001; PCT Publication Nos. WO 99/01157, WO 99/01158 and WO 99/01175).

Pharmaceutical compositions suitable for such gene therapy approaches and comprising nucleic acids encoding an anti-PCSK9 antagonist of the present invention are included within the scope of the present invention.

In another aspect, the present invention provides a method for identifying, isolating, quantifying or antagonizing PCSK9 in a sample of interest using a PCSK9-specific antagonist of the present invention. The PCSK9-specific antagonists may be utilized as research tools in immunochemical assays, such as Western blots, ELISAs, radioimmunoassay, immunohistochemical assays, immunoprecipitations, or other immunochemical assays known in the art (see, e.g., Immunological Techniques Laboratory Manual, ed. Goers, J. 1993, Academic Press) or various purification protocols. The antagonists may have a label incorporated therein or affixed thereto to facilitate ready identification or measurement of the activities associated therewith. One skilled in the art is readily familiar with the various types of detectable labels (e.g., enzymes, dyes, or other suitable molecules which are either readily detectable or cause some activity/result that is readily detectable) which are or may be useful in the above protocols.

An additional aspect of the present invention are kits comprising PCSK9-specific antagonists or pharmaceutical compositions disclosed herein and instructions for use. Kits typically but need not include a label indicating the intended use of the contents of the kit. The term label includes any writing, or recorded material supplied on or with the kit, or which otherwise accompanies the kit. In specific embodiments wherein the pharmaceutical composition is provided lyophilized, the kit may include sterile water or saline for reconstitution of the formulation into liquid form. In specific embodiments, the amount of water or saline is from about 0.1 ml to 1.0 ml.

The following examples are provided to illustrate the present invention without limiting the same hereto:

EXAMPLE 1

Isolation of Recombinant Fab Display Phage

Recombinant Morphosys HuCAL Gold Fab phage display libraries (see, e.g., Knappik et al., 2000 *J. Mol. Biol.* 296:57-86) were panned against immobilized recombinant murine PCSK9 through a process which is briefly described as follows: Phage Fab display libraries were first divided into 3 pools: one pool of VH2+VH4+VH5, another of VH1+VH6, and a third pool of VH3. The phage pools and immobilized PCSK9 protein were blocked with nonfat dry milk.

For the first round of panning, each phage pool was bound independently to V5-, His-tagged PCSK9 protein immobilized in wells of Nunc Maxisorp plate. Immobilized phage-PCSK9 complexes were washed sequentially with (1) PBS/0.5% Tween™ 20 (Three quick washes); (2) PBS/0.5% Tween™ 20 (One 5 min. incubation with mild shaking); (3) PBS (Three quick washes); and (4) PBS (Two 5-min. incubations with mild shaking). Bound phages were eluted with 20 mM DTT and all three eluted phage suspensions were combined into one tube. *E. coli* TG1 were infected with eluted phages. Pooled culture of phagemid-bearing cells (chloramphenicol-resistant) were grown up, and frozen stock of phagemid-bearing culture were made. Phage were rescued from culture by co-infection with helper phage, and phage stock for next round of panning were made.

For the second round of panning, phages from Round 1 were bound to immobilized, blocked V5-, His-tagged PCSK9 protein. Immobilized phage-PCSK9 complexes were washed sequentially with (1) PBS/0.05% Tween™ 20 (One quick wash); (2) PBS/0.05% Tween™ 20 (Four 5 min. incubations with mild shaking); (3) PBS (One quick wash); and (4) PBS (Four 5-min. incubations with mild shaking). Bound phages were eluted, *E. coli* TG1 cells were infected, and phage were rescued as in Round 1.

For the third round of panning, phages from Round 2 were bound to immobilized, blocked V5-His-tagged PCSK9 protein. Immobilized phage-PCSK9 complexes were washed sequentially with (1) PBS/0.05% Tween™ 20 (Ten quick washes); (2) PBS/0.05% Tween™ 20 (Five 5 min. incubations with mild shaking); (3) PBS (Ten quick washes); and (4) PBS (Five 5-min. incubations with mild shaking). Bound phages were eluted and *E. coli* TG1 cells were infected as in Round 1. Phagemid-infected cells were grown overnight and phagemid DNA was prepared.

XbaI-EcoRI inserts from Round 3 phagemid DNA were subcloned into Morphosys Fab expression vector pMORPH_x9_MH to yield plasmid pMORPHx9 MH/mPCSK9 2 CX1 D05 (see, e.g., FIG. 1), and a library of Fab expression clones was generated in *E. coli* TG1 F−. Transformants were spread on LB+chloramphenicol+glucose plates and grown overnight to generate bacterial colonies. Individual transformant colonies were picked and placed into wells of two 96-well plates for growth and screening for Fab expression.

EXAMPLE 2

ELISA Screening of Bacterially Expressed Fabs

Cultures of individual transformants were IPTG-induced and grown overnight for Fab expression. Culture supernatants (candidate Fabs) were incubated with purified V5-, His-tagged PCSK9 protein immobilized in wells of 96-well Nunc Maxisorp plates, washed with 0.1% Tween™ 20 in PBS using a plate washer, incubated with HRP-coupled anti-Fab antibody, and washed again with PBS/Tween™ 20. Bound HRP was detected by addition of TMP substrate, and A450 values of wells were read with a plate reader.

Negative controls were included as follows:
Controls for nonspecific Fab binding on each plate were incubated with parallel expressed preparations of anti-EsB, an irrelevant Fab.
Growth medium only.

Positive controls for ELISA and Fab expression were included as follows:
EsB antigen was bound to three wells of the plate and subsequently incubated with anti-EsB Fab. To control for Fabs reacting with the V5 or His tags of the recombinant PCSK9 antigen, parallel ELISAs were performed using V5-, His-tagged secreted alkaline phosphatase protein (SEAP) expressed in the same cells as the original PCSK9 antigen and similarly purified. Putative PCSK9-reactive Fabs were identified as yielding >3× background values when incubated with PCSK9 antigen but negative when incubated with SEAP. Clones scoring as PCSK9-reactive in the first round of screening were consolidated onto a single plate, re-grown in triplicate, re-induced with IPTG, and re-assayed in parallel ELISAs vs. PCSK9 and SEAP. Positive and negative controls were included as described above. Clones scoring positive in at least 2 of 3 replicates were carried forward into subsequent characterizations. In cases of known or suspected mixed preliminary clones, cultures were re-purified by streaking for single colonies on 2×YT plates with chloramphenicol, and liquid cultures from three or more separate colonies were assayed again by ELISAs in triplicate as described above.

EXAMPLE 3

DNA Sequence Determination of PCSK9 ELISA-Positive Fab Clones

Bacterial culture for DNA preps was made by inoculating 1.2 ml 2×YT liquid media with chloramphenicol from master glycerol stocks of positive Fabs, and growing overnight. DNA was prepared from cell pellets centrifuged out of the overnight cultures using the Qiagen Turbo Mini preps performed on a BioRobot 9600. ABI Dye Terminator cycle sequencing was performed on the DNA with Morphosys defined sequencing primers and run on an ABI 3100 Genetic Analyzer, to obtain the DNA sequence of the Fab clones. DNA sequences were compared to each other to determine unique clone sequences and to determine light and heavy chain subtypes of the Fab clones.

EXAMPLE 4

Expression and Purification of Fabs from Unique PCSK9 ELISA-Positive Clone

Fabs from ELISA-positive clone m2CX1D05 and the EsB (negative control) Fab were expressed by IPTG-induction in *E. coli* TG1F− cells. Cultures were lysed and the His-tagged Fabs were purified by immobilized metal ion affinity chromatography (IMAC), and proteins were exchanged into 25 mM HEPES pH 7.3/150 mM NaCl by centrifugal diafiltration. Proteins were analyzed by electrophoresis on Caliper Lab-Chip 90 and by conventional SDS-PAGE, and quantified by Bradford protein assay. Purified Fab protein was re-assayed by ELISA in serial dilutions to confirm activity of purified Fab. Positive and Negative controls were run as before. Purified Fab preparations were then analyzed as described below.

EXAMPLE 5

Conversion of m2CX1D05 Fab to Full Length IgG

The DNA sequence encoding the m2CX1D05 light chain variable region was amplified by polymerase chain reaction from plasmid template pMORPHx9_MH/mPCSK9_2_CX1_D05, using primers: ACAGATGCCAGATGC-GATATCCAGATGACCCAGA (SEQ ID NO: 33) and TGCAGCCACCGTACGTTTAATTTCAACTTTCGTACC (SEQ ID NO: 34). The product of this amplification was cloned into plasmid pV1JNSA-GS-FB-LCK that had been previously digested with FspI and BmtI, using the InFusion cloning system (Clontech). The resulting plasmid was verified by DNA sequencing across the variable region. Endotoxin-free plasmid preparations were made using the Qiagen Endo-Free plasmid maxiprep kit.

The DNA sequence encoding the heavy chain variable region of pMORPHx9_MH/mPCSK9_2_CX1_D05 was amplified by polymerase chain reaction using primers: ACAGGTGTCCACTCGCAGGTGCAATTG-GTTCAGTCT (SEQ ID NO: 35) and GCCCTTGGTGGAT-GCTGAGCTAACCGTCACCAGGGT (SEQ ID NO: 36), and the amplified product was cloned into plasmid pV1JNSA-BF-HCG2M4 that had been previously digested with FspI and BmtI. The resulting plasmid was verified by DNA sequencing across the variable region. Endotoxin-free plasmid preparations were made using the Qiagen Endo-Free plasmid maxiprep kit.

Full-length IgG was obtained by co-transfection of HEK293 cells with the 1D05 light chain- and heavy-chain-encoding plasmids, following by Protein A purification of the expressed IgG.

EXAMPLE 6

Kinetic Evaluation of Fab:PCSK9 Interactions with Surface Plasmon Resonance ("SPR")

SPR measurements were performed using a Biacore™ (Pharmacia Biosensor AB, Uppsala, Sweden) 2000 system. Sensor chip CM5 and Amine Coupling Kit for immobilization were from Biacore™.

Anti-Fab IgG (Human specific) (Sigma, catalog #I5260) was covalently coupled to surfaces 1 and 2 of a Sensor Chip CM5 via primary amine groups, using the immobilization wizard with the "Aim for immobilization" option using Biacore™ Amine Coupling Kit (cat #BR-1000-50. A target immobilization of 5000 RU was specified. The wizard uses a 7 minute activation with a 1:1 mixture of 100 mM NHS (N-Hydroxysuccinimide) and 400 mM EDC (1-ethyl-3-(3-dimethylaminopropyl)-carbodiimide), injects the ligand in several pulses to achieve the desired level, then deactivates the remaining surface with a 7 minute pulse of ethanolamine.

Anti-PCSK9 Fabs were captured on capture surface 2, and surface 1 was used as a reference for kinetic studies of Fab:PCSK9 interactions. Each Fab was captured by flowing a 500 ng/ml solution at 5 or 10 µl/min for 1-1.5 minutes to reach a target $R_L$ for an $R_{max}$ of 100-150 RU for the reaction. 5-10 concentrations of hPCSK9v5His or mPCSK9v5His antigens were flowed across the surface at 30 µl/minute for 3-4 minutes. 15-60 minutes dissociation time was allowed before regeneration of the Anti-Fab surface with a 30 second pulse of 10 mM glycine pH 2.0.

BiaEvaluation Software was used to evaluate the sensograms from the multiple concentration of PCSK9 antigen analyzed with each Fab, to estimate the kinetics constants of the Fab:PCSK9 interactions.

The kinetic constants were determined as follows:

TABLE 2

| Fab | Antigen | $k_{on}$ (1/Ms × 10$^{-5}$) | $k_{off}$ (1/s × 10$^{4)}$ | $K_D$ (nM) | |
|---|---|---|---|---|---|
| m2CX1D05 Fab | Human PCSK9 | 0.22 ± 0.01 | 2.47 ± 0.05 | 11.5 ± 0.75 | mean (N = 3) |
| m2CX1D05 Fab | Murine PCSK9 | 0.86 ± 0.02 | 2.57 ± 0.19 | 3.35 ± 0.39 | mean (N = 3) |

EXAMPLE 7

Kinetic Evaluation of IgG:PCSK9 Interactions with Surface Plasmon Resonance ("SPR")

SPR measurements were performed using a Biacore™ (Pharmacia Biosensor AB, Uppsala, Sweden) 2000 system. Sensor chip CM5 and Amine Coupling Kit for immobilization were from Biacore™.

A goat Anti-Human IgG (Caltag, catalog #H10700) was covalently coupled to surfaces 1 and 2 of a Sensor Chip CM5 via primary amine groups, using the immobilization wizard with the "Aim for immobilization" option using Biacore™ Amine Coupling Kit (cat #BR-1000-50. A target immobilization of 5000 RU was specified. The wizard uses a 7 minute activation with a 1:1 mixture of 100 mM NHS (N-Hydroxysuccinimide) and 400 mM EDC (1-ethyl-3-(3-dimethylaminopropyl)-carbodiimide), injects the ligand in several pulses to achieve the desired level, then deactivates the remaining surface with a 7 minute pulse of ethanolamine.

Anti-PCSK9 IgGs were captured on capture surface 2, and surface 1 was used as a reference for kinetic studies of IgG:PCSK9 interactions. IgG was captured by flowing a 10 nM solution at 10 µl/min for 1-1.5 minutes to reach a target $R_L$ for an $R_{max}$ of 100-150 RU for the reaction. 5-10 concentrations of hPCSK9v5His or mPCSK9v5His antigens were flowed across the surface at 30 or 60 µl/minute for 4 minutes. 15-60 minutes dissociation time was allowed before regeneration of the Anti-IgG surface with a 60 second pulse of 10 mM Glycine pH 1.7.

BiaEvaluation Software was used to evaluate the sensograms from the multiple concentration of PCSK9 antigen analyzed with each IgG, to estimate the kinetics constants of the IgG:PCSK9 interactions.

The kinetic constants were determined as follows:

TABLE 3

| IgG | Antigen | $k_{on}$ (1/Ms × 10⁻⁵) | $k_{off}$ (1/s × 10⁻⁴) | $K_D$ (nM) | |
|---|---|---|---|---|---|
| 1D05 IgG2m4 | hPCSK9 | 0.88 ± 0.01 | 3.16 ± 0.27 | 3.6 ± 0.33 | mean (N = 2) |
| 1D05 IgG2m4 | mPCSK9 | 0.67 ± 0.06 | 2.15 ± 0.16 | 3.2 ± 0.06 | mean (N = 2) |

EXAMPLE 8

PCSK9-LDLR TR-Fret Assay for 1D05

This assay is a variant of the one described in Fisher et al., 2007 *J. Biol. Chem.* 282:20502-20512. AlexaFluor647-labeled PCSK9 (final concentration 10 nM) was combined with varying amounts of 1D05 and to this was added Eu(8044)-labeled LDLR ectodomain to a final concentration of ~1.5 nM (sufficient to give ~20,000 counts at $Fl_{620}$ nM on the Rubystar) in 10 mM HEPES (pH 7.4), 150 mM NaCl, 0.1 mM $CaCl_2$, 0.05% (w/v) BSA in a total volume of 50 µL using 96 well black Dynatech U bottom plates. After at least 90 minutes of equilibration, samples were read in a Rubystar reader (BMG Corp.) using 20 flashes per well, a 50 usec integration delay, and a 200 usec total integration time. Data were expressed as the ratio of ($Fl_{665}/Fl_{620}$×10000) and an $IC_{50}$ for 1D05 was determined from the inflection point of a sigmoidal dose-response curve using a standard four parameter fit.

Figure 2:
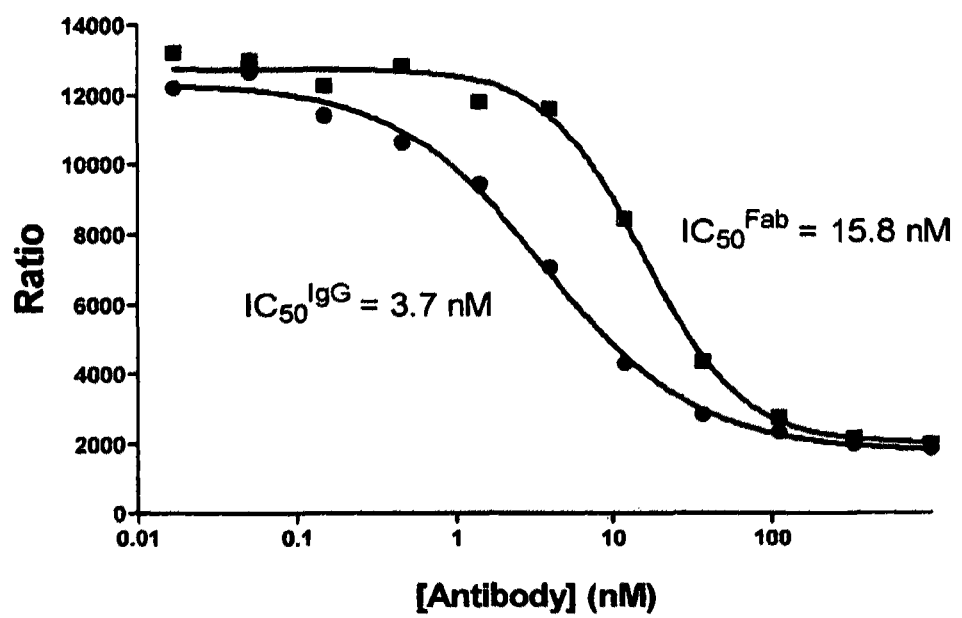
FIG. 2 illustrates the activity of 1D05 in a PCSK9-LDLR interaction TR-FRET assay. Both the Fab and IgG of 1D05 are potent and inhibit the interaction fully. For the experiment, [AF647-PCSK9]=10 nM, [Eu-sLDLR]~1.5 nM (20000 counts at $Fl_{620nm}$).

FIG. 2 illustrates the activity of 1D05 in the PCSK9-LDLR interaction TR-FRET assay. Both the Fab and IgG of 1D05 are potent and inhibit the PCSK9-LDLR interaction fully.

EXAMPLE 9

Exopolar Assay

Effects of Exogenous PCSK9 on Cellular LDL Uptake

On day 1, 30,000 HEK cells/well were plated in a 96 well polyD-lysine coated plate. On day 2, the media was switched to no-serum containing DMEM media. On day 3, the media was removed and the cells were washed with OptiMEM. Purified PCSK9 was added in 100 µl of DMEM media containing LPDS and dI-LDL. The plates were incubated at 37° C. for 6.5 hrs. The cells were washed quickly in TBS containing 2 mg/ml BSA; then washed in TBS-BSA for 2 minutes; and then washed twice (but quickly) with TBS. The cells were lysed in 100 µl RIPA buffer. Fluorescence was then measured in the plate using an Ex 520, Em 580 nm. The total cellular protein in each well was measured using a BCA Protein Assay and the fluorescence units were then normalized to total protein.

The Exopolar Assay is effective for characterizing variant effects on LDL uptake; see Table 4 below illustrating how the potencies of PCSK9 mutants correlate with plasma LDL-cholesterol in the Exopolar Assay.

TABLE 4

| Mutation | Gain/Loss | LDL-C (mg/dl) | EC-50 (nM) Exopolar |
|---|---|---|---|
| S127R | Gain | 277 | 14 |
| D374Y | Gain | 388 | 1.3 |
| Wild-type | | 140 | 51 |
| R46L | Loss | 116 | 78 |

Results:

m2CX1D05, both Fab and IgG, dose-dependently inhibited the effects of both human and murine PCSK9 on LDL uptake; an effect which was reproducibly observed. The amount of PCSK9 added to the cells was ~100-320 nM.

m2CX1D05 (Fab) comprises a light chain of SEQ ID NO: 1 (comprising a VL of SEQ ID NO: 27) and a Fd chain of SEQ ID NO: 9 inclusive of linkers and tags (comprising a VH of SEQ ID NO: 11).

M2CX1D05 (IgG) comprises a light chain of SEQ ID NO: 26, and a heavy chain comprising SEQ ID NO: 25.

Figure 3:
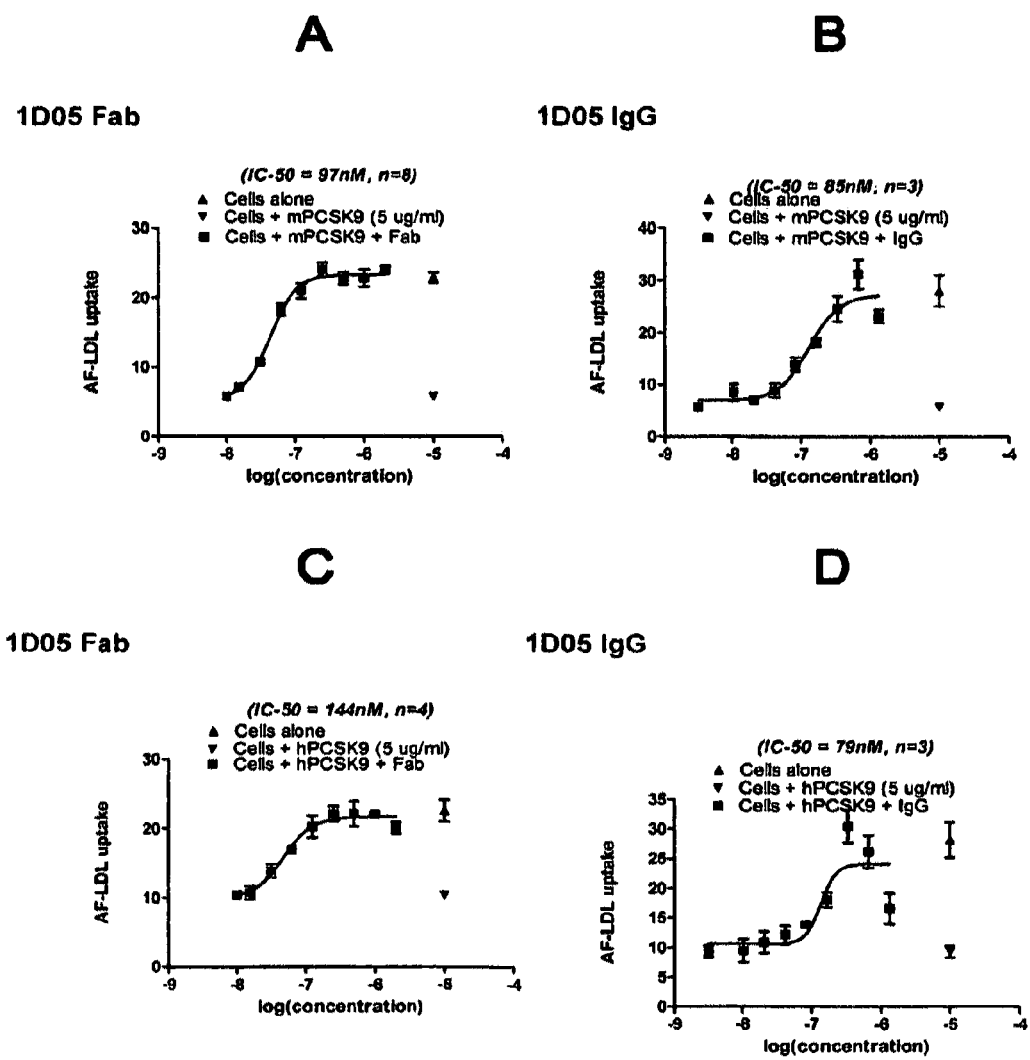
FIGS. 3A-3D illustrate (i) 1D05 (Fab)'s dose-dependent inhibition of murine PCSK9-dependent loss of cellular LDL-uptake (FIG. 3A); (ii) 1D05 (IgG)'s dose-dependent inhibition of murine PCSK9-dependent loss of cellular LDL-uptake (FIG. 3B); (iii) 1D05 (Fab)'s dose-dependent inhibition of human PCSK9-dependent loss of cellular LDL-uptake (FIG. 3C); and (iv) 1D05 (IgG)'s dose-dependent inhibition of human PSCK9-dependent loss of cellular LDL-uptake (FIG. 3D). 1D05 clearly cross-reacts with both human and mouse PCSK9.

FIGS. 3A-3D illustrate (i) 1D05 (Fab)'s dose-dependent inhibition of murine PCSK9-dependent loss of cellular LDL-uptake (FIG. 3A); (ii) 1D05 (IgG)'s dose-dependent inhibition of murine PCSK9-dependent loss of cellular LDL-uptake (FIG. 3B); (iii) 1D05 (Fab)'s dose-dependent inhibition of human PCSK9-dependent loss of cellular LDL-uptake (FIG. 3C); and (iv) 1D05 (IgG)'s dose-dependent inhibition of human PSCK9-dependent loss of cellular LDL-uptake (FIG. 3D).

1D05 clearly cross reacts with both human and mouse PCSK9. FIGS. 3A-3D have two controls: (i) a cell only control, showing the basal level of cellular LDL uptake, and (ii) a cell+PCSK9 (5 µg/ml) control which shows the level of PCSK9-dependent loss of LDL-uptake. The titration experiments which contain 1D05 and PCSK9 were done at a fixed concentration of PCSK9 (5 µg/ml) and increasing concentrations of 1D05 shown in the graphs.

1D05 can inhibit the effect of PCSK9 on cellular LDL uptake. $IC_{50}$s for 1D05 (Fab) are 97 and 144 nM for mouse and human PCSK9 protein, respectively. $IC_{50}$s for 1D05 (IgG) are 85 and 79 nM for mouse and human PCSK9 protein, respectively.

EXAMPLE 10

PCSK9 Cellular Uptake

The assay that follows was carried out according to the methods of Fisher et al., 2007 *J. Biol. Chem.* 282: 20502-12.

Cells treated with Alexa Fluor 647-labeled PCSK9 were imaged as follows. CHO cells were plated on poly-D-lysine-coated 96-well optical CVG sterile black plates (Nunc) at a density of 20,000 cells/well. Cells were plated in F-12K medium (nutrient mixture, Kaighn's modification (1×)) (Invitrogen) containing 100 units of penicillin and 100 µg/ml streptomycin sulfate and supplemented with 10% FBS. Plates were incubated overnight at 37° C. and 5% $CO_2$. The following morning, the medium was removed and replaced with 100 µl of F-12K medium containing 100 units of penicillin and 100 µg/ml streptomycin sulfate. After 18 h, the medium was removed. Purified PCSK9 protein was labeled with Alexa Fluor 647 as described under "Experimental Procedures." Alexa Fluor 647-labeled PCSK9 (1, 5, or 20 µg/ml) was added in 50 µl of F-12K medium containing 10% lipoprotein-deficient serum to the cells. The plates were incubated at 37° C. for 4 h, and the cells were washed quickly with Tris-buffered saline before imaging. To label cellular nuclei, Hoechst 33342 at a final concentration of 0.1 µg/ml was added to each well. The plates were run on an Opera imager (Evotec Technologies GmbH, Hamburg, Germany) with a x40 water immersion objective. Images were captured using excitation wavelengths of 405 nm for fluorescent nuclei and 635 nm for Alexa Fluor 647-labeled PCSK9. For each well, 11 individual fields containing >500 cells were captured for two emission wavelengths. The data were analyzed using a customized algorithm written using the Acapella language (Evotec Technologies GmbH). The algorithm identified and marked the nuclear and cytoplasmic areas of individual cells, followed by measurement of the total cytoplasmic intensity of the cell. The intensity was expressed in arbitrary fluorescent units.

For testing the 1D05 Ab, the identical procedure was used, but with either HEK293 or HepG2 cells. For HepG2 cells, the plates would not have been poly-D-lysine coated. 5 µg/ml of AF647-labeled WT PCSK9 was added along with a titration of Fab ranging from 50 µg/ml down. Using this procedure, we obtained $IC_{50}$ values of roughly 80 nM for the Fab in both cell types.

Results:

FIGS. 4A and 4B illustrate inhibition of PCSK9 internalization by the Fab 1D05 and IgG 1D05 and restoration of LDL uptake.

EXAMPLE 11

In Vivo Assay

Both Fab fragments and whole IgG of human 1D05 were tested in vivo in mice and changes in the level of LDL cholesterol were monitored. The mice used in these studies were (B6xB6-Tg(CETP) Ldlr$^{tm1}$)F1 mice which are hemizygous for the transgenic (Tg) expression of human CETP (which mice lack) as well as the disruption of the LDL receptor (tm1). These mice are particularly useful because of their human-like lipid profiles and LDL-rich nature.

Each mouse was bled twice, once at the beginning of the study to establish individual baseline levels of LDL cholesterol ("pre") and a second time 3 hours later ("post") to assess what changes took place in LDL levels after treatment. Each mouse received two IV doses of Dulbecco's PBS as a vehicle control, 1D05 IgG (0.5 mg), or 1D05 Fab fragments (0.5 mg) over the course of 3 hours. The 1D05 whole IgG was centrifuged at 230,000xg to remove aggregates immediately prior to injection.

Figure 5:
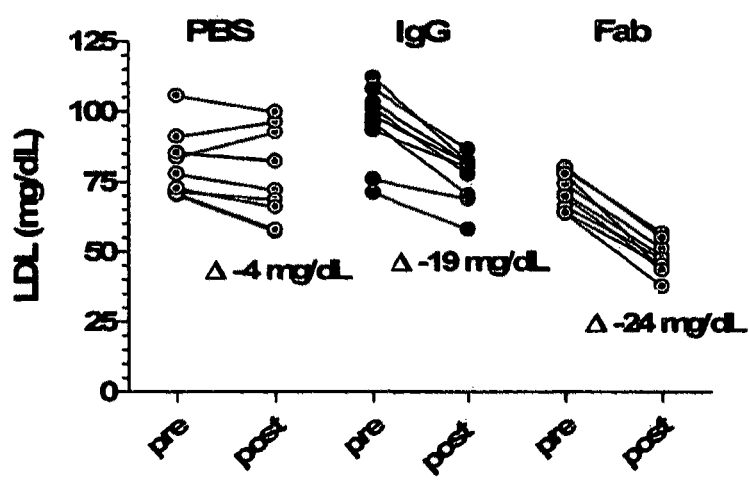
FIG. 5 illustrates the LDL levels for each mouse represented by a set of connected symbols; the change in LDL (postbleed-prebleed) being shown as an average for each treatment group (Δ mg/dL). Treatment with PBS had no effect on LDL measurements (−4 mg/dL, 5% reduction). In contrast, serum LDL was reduced 20% with 1D05 whole IgG (−19 mg/dL) and 34% with Fab fragments of 1D05 (−24 mg/dL).
Figure 8:
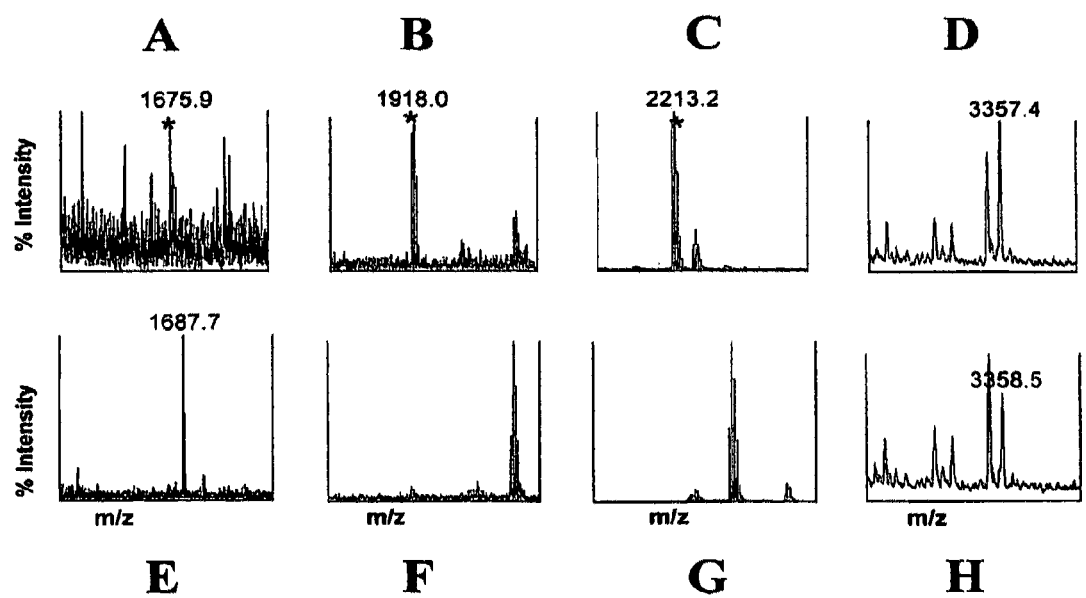
FIGS. 8A-8H illustrate peptide fragments originated by limited proteolysis of wt-PCSK9 (FIGS. 8A-8D) and 1D05/wt-PCSK9 complex (FIGS. 8E-8H) with GluC for 15 minutes.
Figure 9:
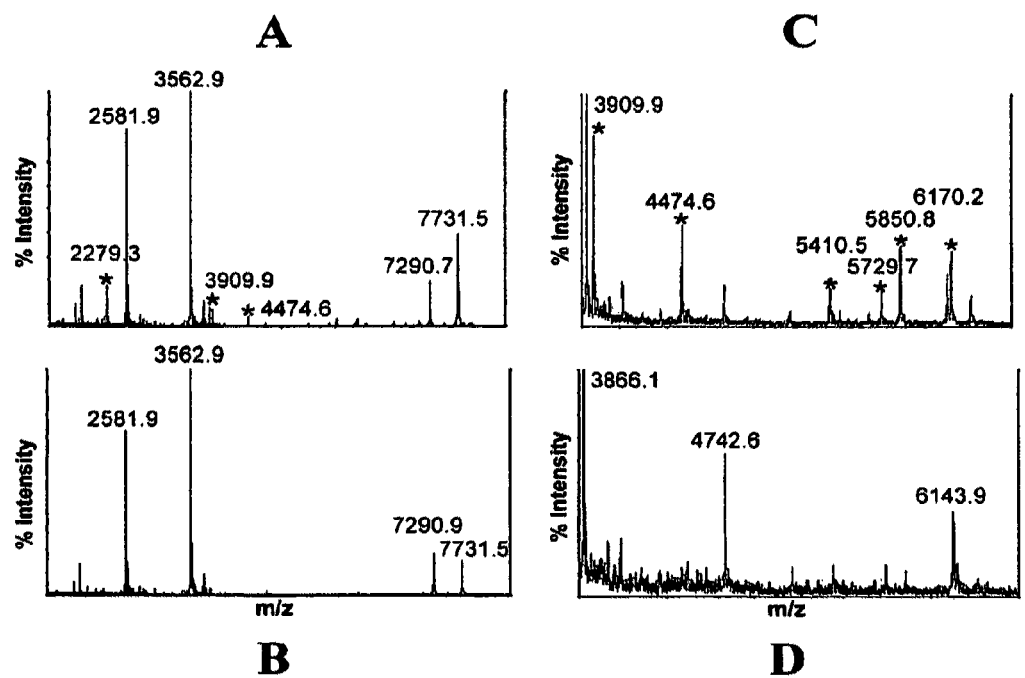
FIGS. 9A-9D illustrate peptide fragments originated by limited proteolysis with Trypsin of a) wt-PCSK9 and b) 1D05/wt-PCSK9 complex for 5 minutes.

In FIG. 5, the LDL levels for each mouse are represented by a set of connected symbols and the change in LDL (postbleed-prebleed) is shown as an average for each treatment group (Δ mg/dL). Treatment with PBS had no effect on LDL measurements (−4 mg/dL, 5% reduction). In contrast, serum LDL was reduced 20% with 1D05 whole IgG (−19 mg/dL) and 34% with Fab fragments of 1D05 (−24 mg/dL).

EXAMPLE 12

Limited Proteolysis

The limited proteolysis mass spectrometry strategy consists in the incubation of wt-hPCSK9 and 1D05/wt-hPCSK9 complex (substrates) with endoproteinase enzymes of different specificity in carefully controlled conditions (i.e., low enzymes concentration and short digestion time). Under these conditions, the endoproteases will cleave only the primary cleavage sites of the protein substrate (i.e., sites that are on the surface of the protein substrate and exposed to the solvent). The binding of 1D05 Fab to wt-hPCSK9 will mask some surface residues normally exposed to the solvent in both proteins. Therefore the primary sites cleaved in wt-hPCSK9 and not in the 1D05/wt-hPCSK9 complex correspond to residues of PCSK9 protected by 1D05 in the complex. Some of these residues are likely to be directly involved in 1D05 binding. The proteolytic peptides generated by wt-hPCSK9 and 1D05/wt-hPCSK9 limited proteolysis are identified and characterized by analysis of the digest by Matrix Assisted Laser Desorption/Ionization Mass Spectrometry (MALDI-MS). Finally, the use of endoproteases with different specificity helps to more accurately define the residues involved in binding.

The amount of proteolytic enzyme normally used in limited proteolysis experiments had to be considerably reduced to avoid excess hydrolysis of wt-hPCSK9 and loss of the primary binding sites (exposed residues). Incubation of wt-hPCSK9, 1D05 and 1D05/wt-hPCSK9 with endoproteases was done in 25 mM HEPES pH 7.5, 150 mM NaCl at room temperature. The endoproteases used were AspN added at a 2500/1 (w/w) excess of protein compared to proteolytic enzyme, and Trypsin and GluC added at a 1000/1 (w/w) protein to endoprotease ratio. At periods of time 5, 15 and 30 minutes after endoprotease addition, an aliquot of sample was deposited onto the MALDI target and subjected to direct MALDI-MS analysis in the presence of sinapinic acid (SA) as matrix. The fragment peptides originated from wt-PCSK9 after incubation with the proteolytic enzyme at various time were compared with those originated from wt-hPCSK9 in the 1D05/wt-hPCSK9 complex sample to identify the residues protected from proteolysis in the 1D05/wt-hPCSK9 interaction. The Figures and Tables provided herein report only the most relevant fragment peptides.

Limited Proteolysis with Endoprotease AspN:

The wt-hPCSK9 protein, 1D05/wt-hPCSK9 complex and 1D05 Fab were incubated for 5, 15 and 30 minutes in the presence of AspN, which cleaves N-terminally to Asp residues, at a 2500/1 (w/w) ratio between the protein and the proteolytic enzyme. MALDI-MS analysis of the digests revealed the primary wt-hPCSK9 and 1D05/wt-hPCSK9 complex cleavage sites (see FIGS. 7A and 7B and Table 5 below). Table 5 illustrates the wt-hPCSK9 fragment peptides obtained after AspN incubation for 5 minutes with wt-PCSK9 and 1D05/wt-hPCSK9 complex. In italics are peptides formed only when wt-hPCSK9 hydrolyzes.

TABLE 5

| Measured m/z | Expected MW | Peptide | Cleaved AA |
|---|---|---|---|
| *1969.1* | *1969.1* | *153-168* | *Asp169* |
| 2222.0 | 2222.0 | 31-49 | Asp49 |
| 4412.9 | 4411.2 | 698-737 | Asp698 |

The species at m/z 1969.1, originated from the cleavage at Asp169 and matching the theoretical mass of peptide 153-168 of the catalytic domain of wt-hPCSK9, was formed only in the wt-hPCSK9 sample indicating that this residue is protected from proteolysis by 1D05 Fab binding in the 1D05/wt-hPCSK9 complex. Several species were formed in both wt-hPCSK9 and 1D05/wt-hPCSK9 hydrolyses. In particular the ions at m/z 2222.0 and 4412.9 corresponding to peptides 31-49 of the prodomain and 698-737 of the catalytic domain of wt-hPCSK9 were originated from cleavage at Asp49 and Asp698.

At longer endoprotease AspN incubation time (i.e., 15, 30 minutes) the peptide profile shown in the MALDI-MS spectra did not change significantly compared to the one at 5 minutes shown in FIGS. 7A and 7B confirming that Asp169 is protected from hydrolysis in the 1D05/wt-PCSK9 interaction.

It is important to note that the observed degree of agreement between the expected and measured mass values is within the norm for this type of experiment, since mass calibration must be made with an external standard.

Limited Proteolysis with Endoprotease GluC:

Endoprotease GluC cleaves C-terminally Glu residues. Incubation of GluC with wt-hPCSK9, 1D05/wt-hPCSK9 complex and 1D05 was conducted at a 1000/1 and 100/1 (w/w) ratio between protein and proteolytic enzyme. To detect the primary cleavage sites, the MALDI-MS analysis of the samples was conducted after 5, 15 and 30 minutes of incubation. The wt-hPCSK9 residues cleaved in the wt-hPCSK9 protein and protected in the 1D05/wt-hPCSK9 complex, and the corresponding peptides detected in the MS spectrum, are shown in FIGS. 8A-H and Table 6 below. Table 6 illustrates peptide fragments obtained upon GluC incubation for 15 minutes with wt-PCSK9 and 1D05/wt-PCSK9 complex. In italics are the peptides originating from wt-PCSK9 and not from the complex.

TABLE 6

| Measured m/z | Expected MW | Peptide | Cleaved AA |
|---|---|---|---|
| *1675.9* | *1675.8* | *182-195* | *Glu181* |
|  |  |  | *Glu195* |
| *1918.0* | *1918.0* | *182-197* | *Glu181* |
|  |  |  | *Glu197* |
| 2213.2 | 2213.1 | 153-170 | Glu170 |
| 3357.4 | 3357.7 | 153-181 | Glu181 |

With endoprotease GluC, protection is shown in the wt-hPCSK9 surface area including residues Glu170, Glu197 and Glu195. The specie at m/z 3357.4, corresponding to peptide 153-181, and obtained in the incubation with GluC of both wt-hPCSK9 and 1D05/wt-hPCSK9, indicates that Glu181 is not protected by the Fab 1D05 binding to wt-hPCSK9.

Limited Proteolysis with Trypsin:

Trypsin cleaves C-terminally Arg and Lys residues. The enzyme was added at 1000 (w/w) ratio to wt-PCSK9, 1D05/wt-PCSK9 complex and 1D05 for 5, 15 and 30 minutes. MALDI-MS analysis of the wt-PCSK9 and 1D05/wt-PCSK9 complex is shown in FIGS. 9A-D and the most relevant peptide fragments are reported in Table 7. Table 7 illustrates peptide fragments obtained upon Trypsin incubation for 5 minutes with wt-PCSK9 and 1D05/wt-PCSK9 complex. In italics are the peptides originating from wt-PCSK9 and not from the complex.

TABLE 7

| Measured m/z | Expected MW | Peptide | Cleaved AA |
|---|---|---|---|
| 1877.9 | 1878.0 | 31-46 | Arg46 |
| 2279.3 | 2279.5 | 200-218 | Arg199 |
|  |  |  | Arg218 |
| 2581.9 | 2581.9 | 706-729 | Arg705 |
|  |  |  | Arg729 |
| 3562.9 | 3562.9 | 706-737 | Arg705 |
| *3909.9* | *3910.2* | *166-199* | *Arg165* |
|  |  |  | *Arg199* |
| *4474.6* | *4474.9* | *161-199* | *Arg160* |
|  |  |  | *Arg199* |
| *5410.5* | *5410.8* | *168-215* | *Arg167* |
|  |  |  | *Arg215* |
| *5729.7* | *5730.2* | *166-215* | *Arg165* |
|  |  |  | *Arg215* |
| *5850.8* | *5851.3* | *168-218* | *Arg167* |
|  |  |  | *Arg218* |

TABLE 7-continued

| Measured m/z | Expected MW | Peptide | Cleaved AA |
|---|---|---|---|
| *6170.2* | *6170.7* | *166-218* | *Arg165* |
|  |  |  | *Arg218* |
| 7290.7 | 7291.0 | 153-215 | Arg215 |
| 7731.5 | 7731.5 | 153-218 | Arg218 |

The primary cleavage sites at 5 minutes were Arg46 on the prodomain and Arg160, Arg165, Arg167, Arg199, Arg215, Arg218, Arg705 and Arg729 on the catalytic domain of wt-hPCSK9. The species at m/z 2279.3, 3909.9 and 4474.6 corresponding to peptides 200-218, 166-199 and 161-199 are detected only in the wt-hPCSK9 hydrolysis and indicate that residue Arg199 is protected by 1D05 binding. These peptide fragments together with the species at m/z 5410.5, 5729.7, 5850.8, 6170.2 correspond to peptides 168-215, 166-215, 168-218, 166-218, detected only in wt-PCSK9 thus indicating protection also on residues Arg165 and Arg167.

At 15 minutes of Trypsin incubation, protection on residue Arg199 is confirmed. In fact the species at m/z 2280.0, 3591.4, 3910.9 and 4475.6, all originated from cleavage at Arg199, are present only in the wt-PCSK9 hydrolysis and become more abundant. In addition, protection at Arg194 is detected (as shown by the presence of the specie at m/z 3325.7 in the wt-PCSK9 spectrum). The species originated from cleavage at Arg165 and Arg167 (m/z 5411.5, 5730.9, 5851.8 and 6171.6) are present in the wt-hPCSK9 hydrolysis and start to appear with much lower intensity also in the 1D05/wt-hPCSK9 complex proteolysis. This may indicate that the protection from proteolysis on such residues is due to steric hindrance of the Fab rather than to primary contacts between 1D05 and wt-PCSK9 residues.

Figure 11:
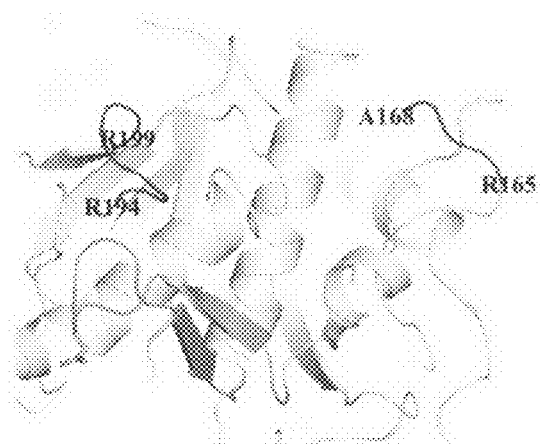
FIG. 11 illustrates peptides of the wt-PCSK9 catalytic domain involved in binding with 1D05 neutralizing Fab. The peptides of wt-PCSK9 protected in limited proteolysis experiments by 1D05 binding are depicted in the segments between R194 and R199, and A168 and R165 in the zoom view of the structure of wt-PCSK9.

Results:

With LP-MS using three enzymes of different specificity, we identified the surface area of wt-hPCSK9 protected by the 1D05 Fab in the 1D05-wt-hPCSK9. Arg165, Arg167, Asp169, Glu170, Arg194, Glu197 and Arg199 are the residues of wt-hPCSK9 protected upon binding to the 1D05 Fab (see FIG. 10). These residues belong to the catalytic domain of wt-hPCSK9 and are exposed on the surface of the molecule (see FIG. 11). In addition, the limited proteolysis with trypsin shows the possibility that residues 194-199 are directly involved in 1D05 binding whereas protection from proteolysis on residues Arg165 and Arg167 may be due to steric hindrance of the Fab instead of direct contacts between 1D05 and wt-PCSK9 residues.

Residues in peptides R194-R199 are conserved in human and mouse PCSK9. 1D05 Fab recognizes human and mouse protein. As illustrated by the sequence alignment between human and mouse PCSK9 (see FIG. 12), the residues included in the peptide 194-199 of wt-PCSK9 and protected by 1D05 are conserved in both human and mouse PCSK9 while residues in peptide 165-169 (also protected by 1D05 binding) are not. This would support a hypothesis that only residues 194-199 are directly interacting with 1D05 while the others (165-169) are protected from proteolysis by steric hindrance.

EXAMPLE 13

PCSK9/1D05 TR-Fret Assay

Anti-V5 antibody (QED Biosciences) was labeled and purified as described previously (see Fisher et al., 2007 *J. Biol. Chem.* 282 (28): 20502-20512) using 4 equivalents of AlexaFluor 647 (Invitrogen). 1D05 IgG was labeled in a similar manner using 5 equivalents of Eu(W8044)-DTA (Perkin-Elmer). Materials were protected from light and stored at 4° C. prior to use. V5/His-PCSK9 was generated as described previously (see Fisher et al., Id.).

TR-FRET assays were carried out in black Microfluor 2 96 well plates (Dynex Technologies) in 10 mM Hepes pH 7.4, 150 mM NaCl, 100 uM $CaCl_2$ and 0.05% BSA. To 25 μL of 20 nM each AF647 labeled anti-V5 antibody and V5/His-PCSK9 was added a serial dilution of the unlabeled candidate antibody (i.e., 1D05 and 1B20), either Fab or IgG. Reagents were equilibrated for ~15 minutes at room temperature and then Eu(W8044)-1D05 IgG was added to give a final concentration of 1.5 nM Eu labeled antibody (~18000 counts at $Fl_{620}$ nm; S/B=12) and a total volume of 50 uL. After, equilibration assays were read in a BMG LabTech Rubystar Reader as described previously (Fisher et al., Id.). Data are reported as $Fl_{665}/Fl_{620} \times 10000$. $IC_{50}$s were determined using data fitted to a sigmoidal dose response curve using non-linear regression analysis (Kaleidagraph 4.03, Synergy Software).

Figure 13:
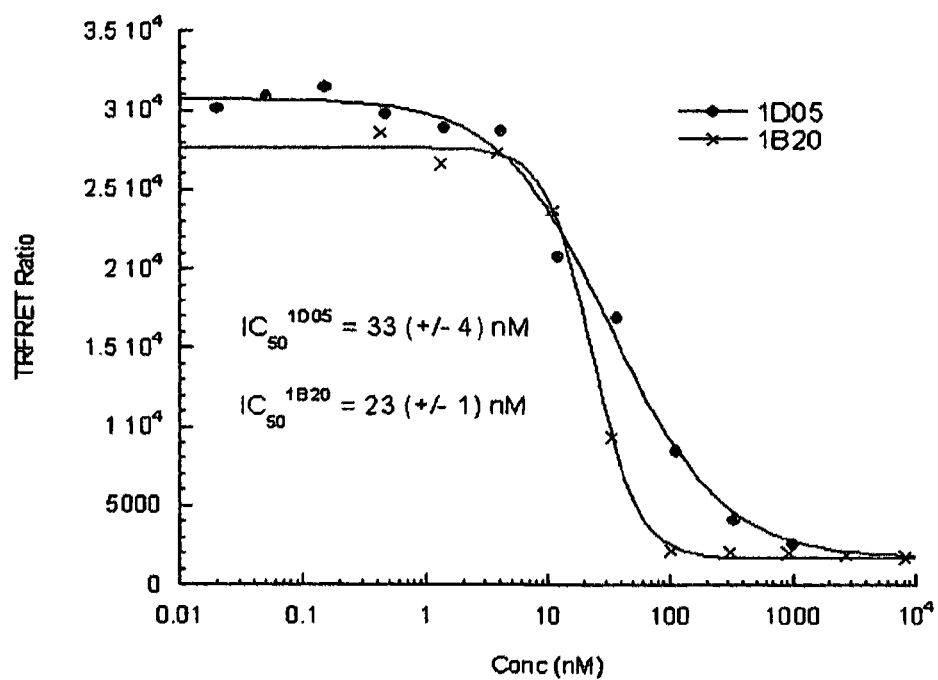
FIG. 13 illustrates an analysis of 1D05 and a distinct antibody 1B20 in a PCSK9-1D05 interaction TR-FRET assay. Both Fabs are potent and inhibit the interaction fully. For this experiment, [AF647-α-V5]=10 nM, [PCSK9]=10 nM, and [Eu(8044)-1D05(IgG)]~1.5 nM (~18000 counts at F1620 nm).

FIG. 13 illustrates an analysis of 1D05 and a distinct antibody 1B20 in a PCSK9-1D05 interaction TR-FRET assay. Both Fabs are potent and inhibit the interaction fully. FIGS. 14A-D illustrates 1B20's inhibition of PCSK9 in the Exopolar assay described, e.g., in Example 9. 1B20 Fab inhibited murine PCSK9 at an $IC_{50}$ of 152 nM (n=5); and human PCSK9 at an $IC_{50}$ of 145 nM (n=5). 1B20 IgG inhibited murine PCSK9 at an $IC_{50}$ of 13 nM; and human PCSK9 at an $IC_{50}$ of 22 nM. The binding particulars of 1B20 Fab are illustrated in the following Table.

TABLE 8

|  | hPCSK9v5His | mPCSK9v5His |
| --- | --- | --- |
| $k_a$ (1/Ms) | 6.6E+04 ± 6.1E+03 | 1.41E+05 ± 1.2E+04 |
| $k_d$ (1/s) | 4.8E−05 ± 7.4E−06 | 7.18E−05 ± 2.9E−06 |
| $K_A$ (1/M) | 1.5E+09 ± 3.0E+08 | 2.0E+09 ± 1.5E+08 |
| $K_D$ (M) | 7.4E−10 ± 1.6E−10 | 5.1E−10 ± 3.8E−11 |

EXAMPLE 14

1D05 Rhesus PK/PD Study

To characterize pharmacokinetics, pharmacodynamics and target engagement of 1D05, a single dose IV study was conducted in male Rhesus monkeys at 3 mg/kg (7.0-9.0 kg, n=3). All Rhesus monkeys used in the study were naïve to biologics.

Monkeys were given an IV bolus dose of 1D05 via the cephalic vein. Blood samples were collected from the saphenous/femoral vessel at designated time points post dosing and the resulting plasma/serum was stored at −70° C. until analysis.

The dosing solutions of 1D05 were prepared at 47.2 mg/mL in 100 mM Histidine, 100 mM Arginine, 6% sucrose, pH 6.0. The dosing solutions were stored at 4° C. and kept on wet ice during dosing.

The lipoprotein analysis of the serum samples were carried out as described below. An anti-human IgG ELISA using commercially available reagents was used to quantify 1D05 levels.

Figure 15:
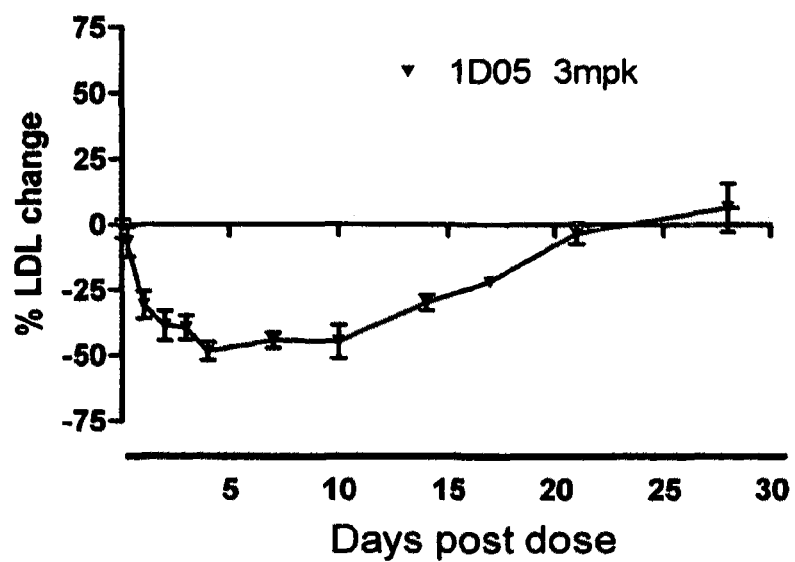
FIG. 15 illustrates 1D05 lowering LDL-C by ~50% in rhesus at 3 mpk. Plotted are % LDL changes in serum at the different time points tested, post a single IV dose of antibody treatment.
Figure 16:
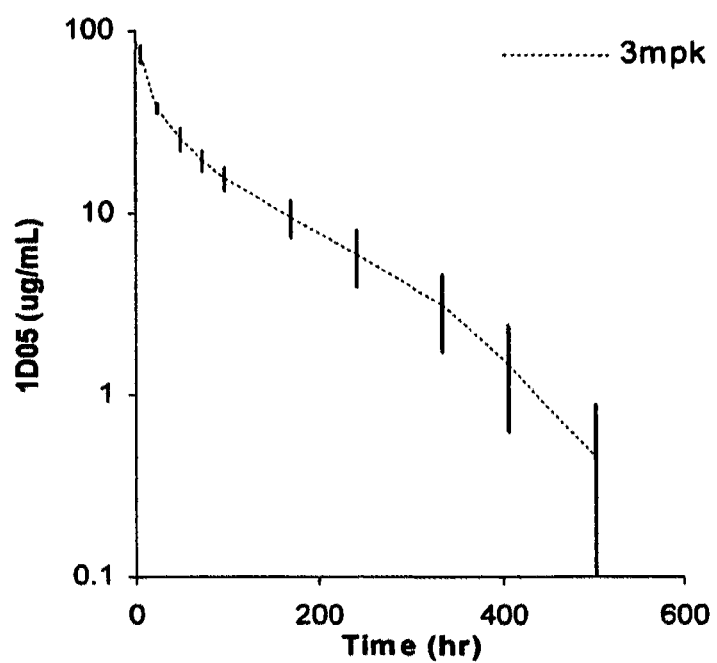
FIG. 16 illustrates the pharmacokinetic profile of 1D05 at the dose levels shown. Plotted are the serum drug (1D05) levels at time points tested following a single IV dose of antibody. The half-life of 1D05 is 77 hr.

As shown in FIG. 15, 1D05 lowered LDL-C by ~50% at 3 mpk and ≥25% LDL-C lowering was observed for ~16 days. The $t_{1/2}$ of 1D05 (FIG. 16) was 77 hr.

EXAMPLE 15

Lipoprotein Analysis of Plasma/Serum Samples from 1D05 Rhesus PK/Pd Study

To generate lipoprotein profiles, plasma or serum was fractionated by chromatography over Superose-6 size exclusion column (GE LifeSciences, Inc.). Total cholesterol levels in the column effluent were continuously measured via in-line mixture with a commercially available enzymatic colorimetric cholesterol detection reagent (Total Cholesterol E, Wako USA) followed by downstream spectrophotometric detection of the reaction products at 600 nm absorbance. The first peak of cholesterol eluted from the column was attributed to VLDL, the second peak to LDL and the third to HDL; the area under each peak was calculated using software provided with the HPLC. To calculate the cholesterol concentration for each lipoprotein fraction, the ratio of the corresponding peak area to total peak area was multiplied by the total cholesterol concentration measured in the sample.

EXAMPLE 16

Formulation

Monoclonal antibodies comprising a light chain comprising SEQ ID NO: 26 and a heavy chain comprising SEQ ID NO: 25) were dialyzed into the appropriate formulations and concentrated. Solutions were then dispensed into 3 mL glass vials for stability studies. Studies carried out in liquid form were immediately placed on stability at 2-8° C. or 25° C.

Analytical methods included Size Exclusion Chromatography (SEC-HPLC) to measure aggregation and fragmentation. Below is a table of Time 0 and 6M SEC data. The formulations containing 3/50/50 or 6/100/100 (sucrose/His/Arg) form fewer aggregates and fragments after storage for 6 months at 2-8° C. or 25° C. All formulations are at 6.0 except for the standard—that is frozen at 1 mg/mL in Phosphate buffered saline (pH ~7).

TABLE 9

| Sample Name | % High Order Aggregates | % Dimer | % Monomer | % Clipped |
| --- | --- | --- | --- | --- |
| 1D05 standard T0 | 0.32% | 1.59% | 98.09% | 0.00% |
| 10His/150 NaCl Time 0 | 0.26% | 1.59% | 98.15% | 0.00% |
| 3/50/50 Time 0 | 0.30% | 1.59% | 98.11% | 0.00% |
| 1D05 standard −70 C. 6 M | 0.60% | 2.79% | 96.61% | 0.00% |
| His/NaCl 4 C. 6 M | 0.98% | 3.18% | 95.83% | 0.01% |
| 6/100/100 4 C. 6 M | 0.95% | 2.90% | 96.13% | 0.02% |
| 3/50/50 4 C. 6 M | 0.92% | 3.00% | 96.07% | 0.01% |
| 100 mg/mL 4 C. 6 M | 0.97% | 3.13% | 95.85% | 0.05% |
| His/NaCl 25 C. 6 M | 1.71% | 4.45% | 93.45% | 0.40% |
| 6/100/100 25 C. 6 M | 1.16% | 3.69% | 94.74% | 0.39% |
| 3/50/50 25 C. 6 M | 1.31% | 3.70% | 94.62% | 0.37% |

EXAMPLE 17

Variants

Site-directed mutant variants of 1D05 were generated and are disclosed herein as SEQ ID NOs: 51-60. Kds of site-directed mutant variants of 1D05 Fabs were determined using a Bio-Rad ProteOn; with affinity being measured against human PCSK9-V5-His. The methodologies for measuring Fab affinities are essentially the same as previously described for Biacore®.

TABLE 10

| Ab ID | Chain Mutated | Comprising VH | KD (nM) |
|---|---|---|---|
| H32Y | HEAVY | SEQ ID NO: 51 | 2.01 |
| M48AQ | HEAVY | SEQ ID NO: 52 | 2.06 |
| M48L | HEAVY | SEQ ID NO: 53 | 1.52 |
| H99Y | HEAVY | SEQ ID NO: 54 | 1.45 |
| M48L/M109L/M115L | HEAVY | SEQ ID NO: 55 | 1.13 |
| M48V | HEAVY | SEQ ID NO: 56 | 1.95 |
| N50D | LIGHT | SEQ ID NO: 57 | 3.42 |
| N50Q | LIGHT | SEQ ID NO: 58 | 0.615 |
| N50T | LIGHT | SEQ ID NO: 59 | 2.13 |
| N50Y | LIGHT | SEQ ID NO: 60 | 2.58 |

* Amino acid numbering begins with the first residue of FR1, immediately following signal peptide.

What is claimed is:

1. An isolated cDNA encoding a PCSK9 specific antagonist antibody or antigen binding fragment thereof, wherein the antibody or antigen binding fragment comprises:
   a) a heavy chain variable region comprising a CDR1 domain having the amino acid sequence of SEQ ID NO: 13; a CDR2 domain having the amino acid sequence of SEQ ID NO: 15; and a CDR3 domain having the amino acid sequence of SEQ ID NO: 17; and/or
   b) a light chain variable region comprising a CDR1 domain having the amino acid sequence of SEQ ID NO: 3; a CDR2 domain having the amino acid sequence of SEQ ID NO: 5; and a CDR3 domain having the amino acid sequence of SEQ ID NO: 7;

wherein the PCSK-9 specific antagonist antibody or antigen binding fragment thereof antagonizes PCSK-9 mediated inhibition of cellular LDL uptake.

2. The cDNA of claim 1, wherein:
   a) CDR1, 2, and 3 of the heavy chain variable region are encoded by nucleic acid sequences of SEQ ID NO: 14, 16, and 18, respectively; and/or
   b) CDR1, 2, and 3 of the light chain variable region are encoded by nucleic acid sequences of SEQ ID NO: 4, 6, and 8, respectively.

3. The cDNA of claim 1, wherein:
   a) the heavy chain region is encoded by a nucleotide sequence of SEQ ID NO: 12; and/or
   b) the light chain region is encoded by a nucleotide sequence of SEQ ID NO: 28.

4. A vector comprising the cDNA of claim 1.

5. An isolated host cell or population of host cells in vitro or in situ comprising the cDNA of claim 1.

6. A method for producing a PCSK9 antagonist antibody or antigen binding fragment which comprises:
   a) culturing the cells of claim 5 under conditions appropriate for expression of the PCSK9 antagonist antibody or antigen binding fragment thereof; and
   b) isolating the expressed PCSK9 antagonist antibody or antigen binding fragment thereof.

* * * * *